United States Patent
Makarov et al.

(10) Patent No.: US 10,480,030 B2
(45) Date of Patent: Nov. 19, 2019

(54) POLYNUCLEOTIDE PRIMERS AND PROBES

(71) Applicant: SWIFT BIOSCIENCES, INC., Ann Arbor, MI (US)

(72) Inventors: Vladimir Makarov, Ann Arbor, MI (US); Sergey V. Chupreta, Ann Arbor, MI (US)

(73) Assignee: SWIFT BIOSCIENCES, INC., Ann Arbor, MI (US)

( * ) Notice: Subject to any disclaimer, the term of this patent is extended or adjusted under 35 U.S.C. 154(b) by 454 days.

(21) Appl. No.: 14/092,693

(22) Filed: Nov. 27, 2013

(65) Prior Publication Data

US 2014/0162263 A1 Jun. 12, 2014

Related U.S. Application Data

(63) Continuation of application No. 12/913,742, filed on Oct. 27, 2010, now abandoned.

(60) Provisional application No. 61/255,461, filed on Oct. 27, 2009.

(51) Int. Cl.
| | |
|---|---|
| *C12Q 1/68* | (2018.01) |
| *C12Q 1/6876* | (2018.01) |
| *C12Q 1/6818* | (2018.01) |
| *C12Q 1/6832* | (2018.01) |

(52) U.S. Cl.
CPC ......... *C12Q 1/6876* (2013.01); *C12Q 1/6818* (2013.01); *C12Q 1/6832* (2013.01)

(58) Field of Classification Search
None
See application file for complete search history.

(56) References Cited

U.S. PATENT DOCUMENTS

| | | |
|---|---|---|
| 3,687,808 A | 8/1972 | Merigan et al. |
| 4,469,863 A | 9/1984 | Ts'o et al. |
| 4,476,301 A | 10/1984 | Imbach et al. |
| 4,845,205 A | 7/1989 | Huynh Dinh et al. |
| 4,981,957 A | 1/1991 | Lebleu et al. |
| 5,023,243 A | 6/1991 | Tullis |
| 5,034,506 A | 7/1991 | Summerton et al. |
| 5,079,352 A | 1/1992 | Gelfand et al. |
| 5,118,800 A | 6/1992 | Smith et al. |
| 5,130,302 A | 7/1992 | Spielvogel et al. |
| 5,134,066 A | 7/1992 | Rogers et al. |
| 5,166,315 A | 11/1992 | Summerton et al. |
| 5,175,273 A | 12/1992 | Bischofberger et al. |
| 5,177,196 A | 1/1993 | Meyer, Jr. et al. |

(Continued)

FOREIGN PATENT DOCUMENTS

| | | |
|---|---|---|
| EP | 0745690 A2 | 12/1996 |
| EP | 1072679 A2 | 1/2001 |

(Continued)

OTHER PUBLICATIONS

Amicarelli et al. (Clin Chem, 2006, 52(10):1855-1863).*

(Continued)

*Primary Examiner* — Stephanie K Mummert
(74) *Attorney, Agent, or Firm* — Marshall, Gerstein & Borun LLP

(57) ABSTRACT

The present invention provides a novel technology that involves improved primer design. These primer pairs have a wide range of applications and provide high sensitivity and specificity.

26 Claims, 43 Drawing Sheets

Specification includes a Sequence Listing.

(56) References Cited

U.S. PATENT DOCUMENTS

| | | |
|---|---|---|
| 5,185,444 A | 2/1993 | Summerton et al. |
| 5,188,897 A | 2/1993 | Suhadolnik et al. |
| 5,194,599 A | 3/1993 | Froehler et al. |
| 5,210,015 A | 5/1993 | Gelfand et al. |
| 5,214,134 A | 5/1993 | Weis et al. |
| 5,216,141 A | 6/1993 | Benner |
| 5,235,033 A | 8/1993 | Summerton et al. |
| 5,264,423 A | 11/1993 | Cohen et al. |
| 5,264,562 A | 11/1993 | Matteucci |
| 5,264,564 A | 11/1993 | Matteucci |
| 5,276,019 A | 1/1994 | Cohen et al. |
| 5,278,302 A | 1/1994 | Caruthers et al. |
| 5,286,717 A | 2/1994 | Cohen et al. |
| 5,319,080 A | 6/1994 | Leumann |
| 5,321,131 A | 6/1994 | Agrawal et al. |
| 5,359,044 A | 10/1994 | Cook et al. |
| 5,367,066 A | 11/1994 | Urdea et al. |
| 5,393,878 A | 2/1995 | Leumann |
| 5,399,676 A | 3/1995 | Froehler |
| 5,405,938 A | 4/1995 | Summerton et al. |
| 5,405,939 A | 4/1995 | Suhadolnik et al. |
| 5,424,413 A | 6/1995 | Hogan et al. |
| 5,432,272 A | 7/1995 | Benner |
| 5,434,257 A | 7/1995 | Matteucci et al. |
| 5,446,137 A | 8/1995 | Maag et al. |
| 5,451,503 A | 9/1995 | Hogan et al. |
| 5,453,496 A | 9/1995 | Caruthers et al. |
| 5,455,233 A | 10/1995 | Spielvogel et al. |
| 5,457,187 A | 10/1995 | Gmeiner et al. |
| 5,459,255 A | 10/1995 | Cook et al. |
| 5,466,677 A | 11/1995 | Baxter et al. |
| 5,466,786 A | 11/1995 | Buhr et al. |
| 5,470,967 A | 11/1995 | Huie et al. |
| 5,476,925 A | 12/1995 | Letsinger et al. |
| 5,484,908 A | 1/1996 | Froehler et al. |
| 5,487,972 A | 1/1996 | Gelfand et al. |
| 5,489,677 A | 2/1996 | Sanghvi et al. |
| 5,502,177 A | 3/1996 | Matteucci et al. |
| 5,514,785 A | 5/1996 | Van Ness et al. |
| 5,519,126 A | 5/1996 | Hecht |
| 5,519,134 A | 5/1996 | Acevedo et al. |
| 5,525,711 A | 6/1996 | Hawkins et al. |
| 5,527,899 A | 6/1996 | Froehler |
| 5,536,821 A | 7/1996 | Agrawal et al. |
| 5,539,082 A | 7/1996 | Nielsen et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,552,540 A | 9/1996 | Haralambidis |
| 5,561,225 A | 10/1996 | Maddry et al. |
| 5,563,253 A | 10/1996 | Agrawal et al. |
| 5,565,555 A | 10/1996 | Froehler et al. |
| 5,567,811 A | 10/1996 | Misiura et al. |
| 5,571,799 A | 11/1996 | Tkachuk et al. |
| 5,576,427 A | 11/1996 | Cook et al. |
| 5,587,361 A | 12/1996 | Cook et al. |
| 5,587,469 A | 12/1996 | Cook et al. |
| 5,591,722 A | 1/1997 | Montgomery et al. |
| 5,594,121 A | 1/1997 | Froehler et al. |
| 5,595,890 A | 1/1997 | Newton et al. |
| 5,596,086 A | 1/1997 | Matteucci et al. |
| 5,596,091 A | 1/1997 | Switzer |
| 5,597,909 A | 1/1997 | Urdea et al. |
| 5,602,240 A | 2/1997 | De Mesmaeker et al. |
| 5,608,046 A | 3/1997 | Cook et al. |
| 5,610,289 A | 3/1997 | Cook et al. |
| 5,610,300 A | 3/1997 | Altmann et al. |
| 5,614,617 A | 3/1997 | Cook et al. |
| 5,618,704 A | 4/1997 | Sanghvi et al. |
| 5,618,711 A | 4/1997 | Gelfand et al. |
| 5,623,070 A | 4/1997 | Cook et al. |
| 5,625,050 A | 4/1997 | Beaton et al. |
| 5,627,032 A | 5/1997 | Ulanovsky |
| 5,627,053 A | 5/1997 | Usman et al. |
| 5,633,360 A | 5/1997 | Bischofberger et al. |
| 5,639,873 A | 6/1997 | Barascut et al. |
| 5,645,985 A | 7/1997 | Froehler et al. |
| 5,646,265 A | 7/1997 | McGee |
| 5,646,269 A | 7/1997 | Matteucci et al. |
| 5,658,873 A | 8/1997 | Bertsch-Frank et al. |
| 5,663,312 A | 9/1997 | Chaturvedula |
| 5,670,633 A | 9/1997 | Cook et al. |
| 5,672,697 A | 9/1997 | Buhr et al. |
| 5,677,437 A | 10/1997 | Teng et al. |
| 5,677,439 A | 10/1997 | Weis et al. |
| 5,679,512 A * | 10/1997 | Laney .................... C12Q 1/686 |
| | | 435/6.12 |
| 5,681,941 A | 10/1997 | Cook et al. |
| 5,700,920 A | 12/1997 | Altmann et al. |
| 5,714,331 A | 2/1998 | Buchardt et al. |
| 5,719,262 A | 2/1998 | Buchardt et al. |
| 5,721,218 A | 2/1998 | Froehler |
| 5,750,692 A | 5/1998 | Cook et al. |
| 5,763,588 A | 6/1998 | Matteucci et al. |
| 5,789,224 A | 8/1998 | Gelfand et al. |
| 5,792,608 A | 8/1998 | Swaminathan et al. |
| 5,792,747 A | 8/1998 | Schally et al. |
| 5,830,653 A | 11/1998 | Froehler et al. |
| 5,849,497 A | 12/1998 | Steinman |
| 5,925,517 A | 7/1999 | Tyagi et al. |
| 5,935,791 A | 8/1999 | Nadeau et al. |
| 6,005,096 A | 12/1999 | Matteucci et al. |
| 6,127,155 A | 10/2000 | Gelfand et al. |
| 6,130,047 A | 10/2000 | Nadeau et al. |
| 6,197,556 B1 | 3/2001 | Ulanovsky et al. |
| 6,235,889 B1 | 5/2001 | Ulanovsky |
| 6,248,526 B1 | 6/2001 | Weimer |
| 6,261,784 B1 | 7/2001 | Nadeau et al. |
| 6,268,490 B1 | 7/2001 | Imanishi et al. |
| 6,287,770 B1 | 9/2001 | Weston et al. |
| 6,316,198 B1 | 11/2001 | Skouv et al. |
| 6,326,145 B1 | 12/2001 | Whitcombe et al. |
| 6,887,662 B1 | 5/2005 | Alajem et al. |
| 7,413,854 B2 | 8/2008 | Pedersen et al. |
| 7,579,153 B2 | 8/2009 | Brenner et al. |
| 7,588,891 B2 | 9/2009 | Prudent et al. |
| 7,759,062 B2 | 7/2010 | Allawi et al. |
| 7,799,903 B2 | 9/2010 | Luo et al. |
| 8,932,831 B2 * | 1/2015 | Korfhage ............... C12N 15/10 |
| | | 435/91.2 |
| 2002/0119533 A1 | 8/2002 | Brown |
| 2003/0064370 A1 | 4/2003 | Weston et al. |
| 2004/0219565 A1 | 11/2004 | Kauppinen et al. |
| 2005/0164219 A1 | 7/2005 | Whitcombe et al. |
| 2005/0205434 A1 | 9/2005 | Sen et al. |
| 2006/0257873 A1 | 11/2006 | Lee et al. |
| 2008/0131870 A1 | 6/2008 | Allawi et al. |
| 2008/0293160 A1 | 11/2008 | Sen et al. |
| 2010/0221717 A1 | 9/2010 | Chen et al. |

FOREIGN PATENT DOCUMENTS

| | | |
|---|---|---|
| JP | 2007-130006 A | 5/2007 |
| WO | WO-1997/012896 A1 | 4/1997 |
| WO | WO-1998/039352 A1 | 9/1998 |
| WO | WO-1999/014226 A2 | 3/1999 |
| WO | WO-2001/020035 A2 | 3/2001 |
| WO | WO2001020035 * | 3/2001 ............... C12Q 1/68 |
| WO | WO-2009/19008 A1 | 2/2009 |

OTHER PUBLICATIONS

Patel et al. (PNAS, 1996, 93, p. 2969-2974).*

Amicarelli et al., Genotype-specific signal generation based on digestion of 3-way DNA junctions: Application to KRAS variation detection, Clin. Chem., 52:1855-63 (2006).

Communication relating to Invitation to Pay Additional Fees from corresponding International Application No. PCT/US2010/054362, dated Feb. 10, 2011.

De Mesmaeker et al., Backbone modifications in oligonucleotides and peptide nucleic acid systems, Curr. Opin. Struct. Biol., 5:343-55 (1995).

(56) References Cited

OTHER PUBLICATIONS

Eckstein (ed.), Oligonucleotides and Analogues, 1st ed., New York: Oxford University Press (1991).
Englisch et al., Chemically Modified Oligonucleotides as Probes and Inhibitors, Angewandte Chemie International Edition in English, 30: 613-29.
Freier et al., The ups and downs of nucleic acid duplex stability: structure-stability studies on chemically-modified DNA:RNA duplexes, *Nucleic Acids Res.*, 25:4429-43 (1997).
Kroschwitz (ed.), The Concise Encyclopedia of Polymer Science and Engineering (1990).
Martin et al., Helv. Chim. Acta, 78:486-504 (1995).
Morozova et al., Applications of next-generation sequencing technologies in functional genomics, Genomics, 92:255-64 (2008).
Nielsen et al., Sequence-selective recognition of DNA by strand displacement with a thymine-substituted polyamide, Science, 254:1497-500 (1991).
Sambrook et al., Molecular Cloning: A Laboratory Manual, 2nd ed. (1989).
Sanghvi, Heterocyclic base modifications in nucleic acids and their applications in antisense oligonucleotides, Chapter 15 in: Crooke et al. (eds.), Antisense Research and Applications, CRC Press (1993).
Wharam et al., Specific detection of DNA and RNA targets using a novel isothermal nucleic acid amplification assay based on the formation of a three-way junction structure, Nucleic Acids Res., 29:e54 (8pp., 2001).
International Search Report and Written Opinion for corresponding International application No. PCT/US2010/054362, dated Jun. 22, 2011.
Zhang et al., "A novel real-time quantitative PCR method using attached universal template probe," Nucleic Acids Research, 31(20), pp. 1-8 (2003).
Patel, et al. "Formation of chimeric DNA primer extension products by template switching onto an annealed downstream oligonucleotide," Proc. Natl. Acad. Sci., 93:2969-2974 (1996).

\* cited by examiner

A. Primer with a single 3-way junction
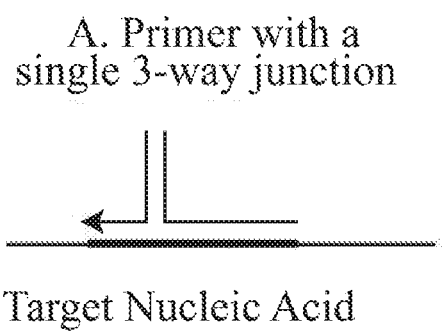
Target Nucleic Acid
B. Primer with two 3-way junctions
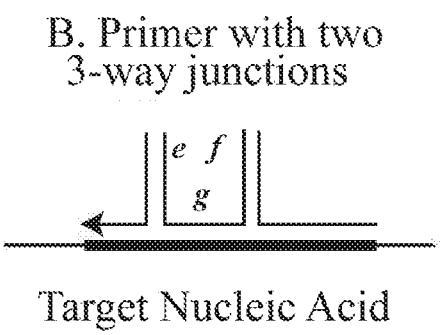
Target Nucleic Acid
FIG. 2

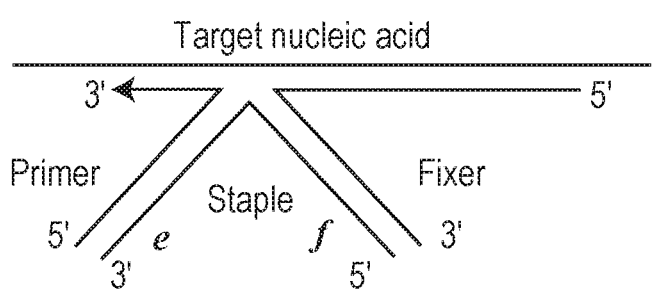
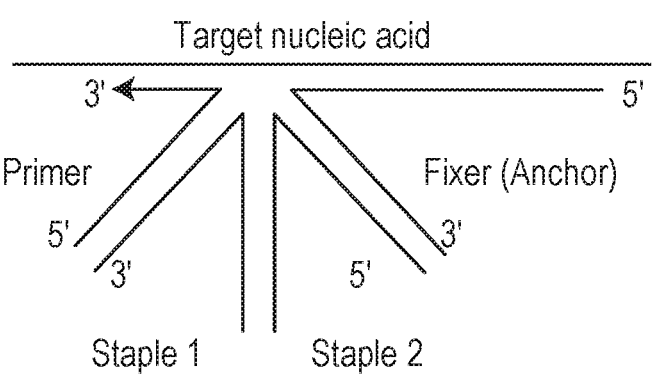
FIG. 3

A.
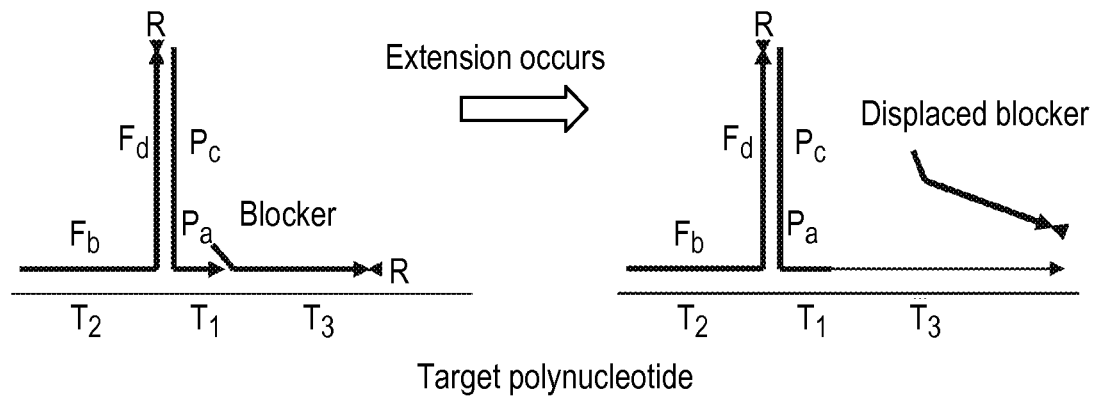
Target polynucleotide
B.
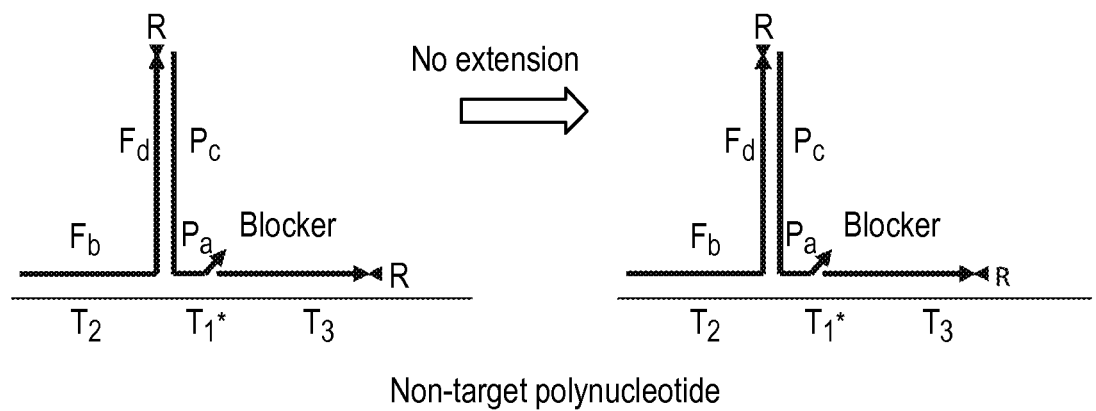
Non-target polynucleotide
*FIG. 4*

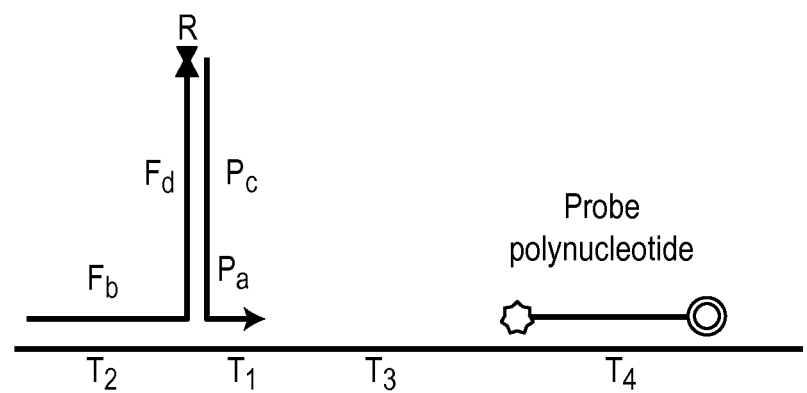
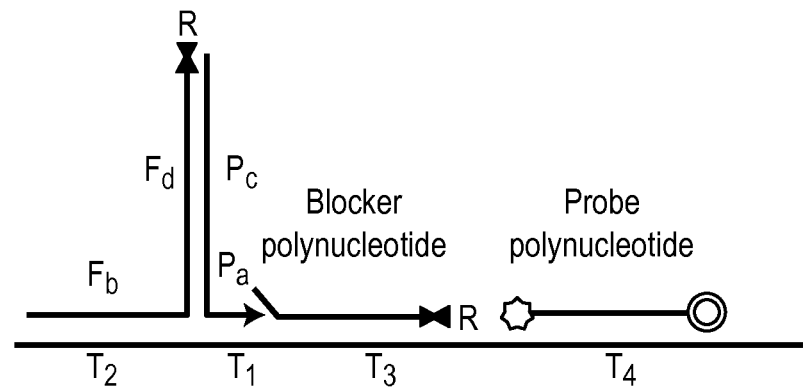
FIG. 5

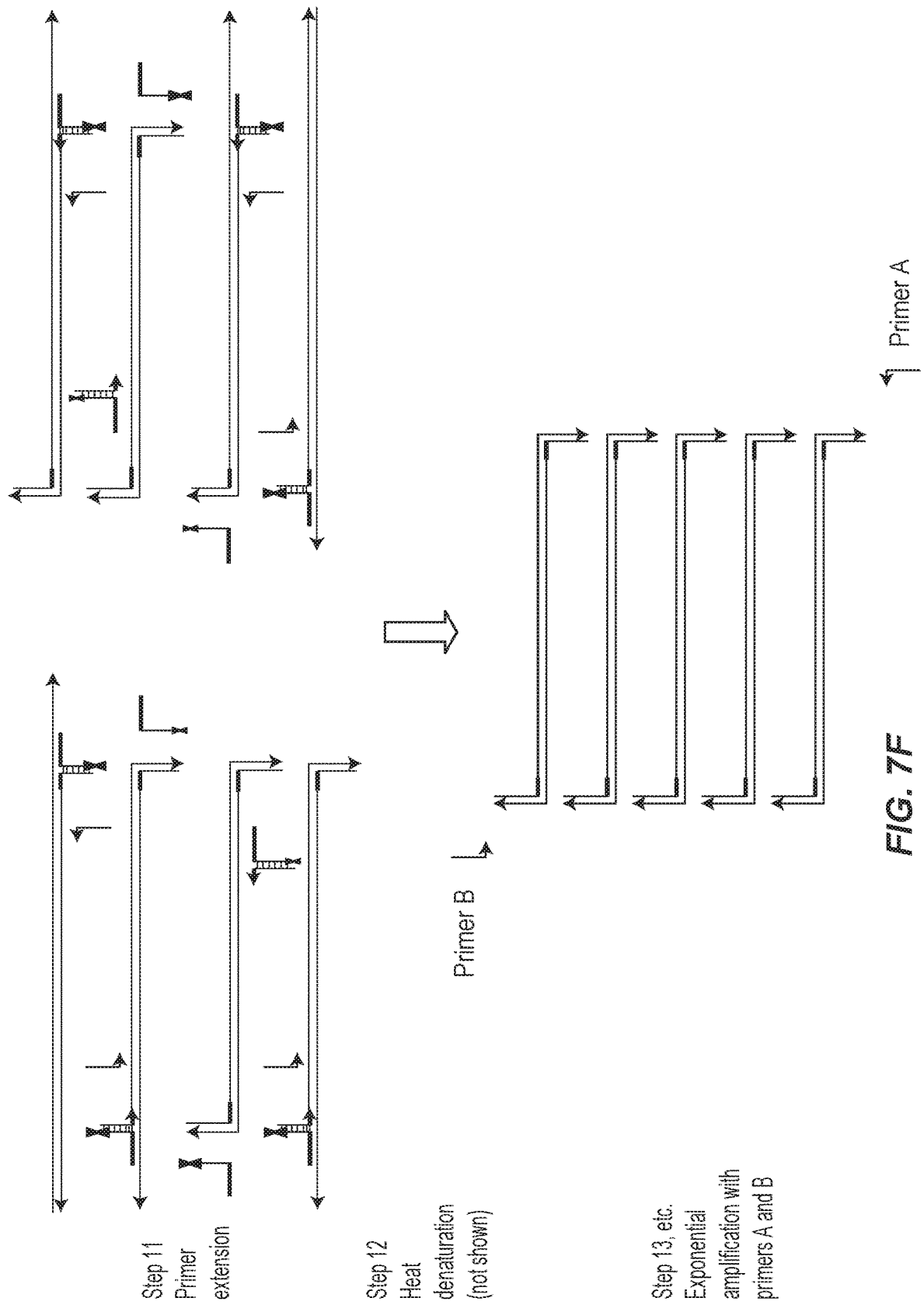

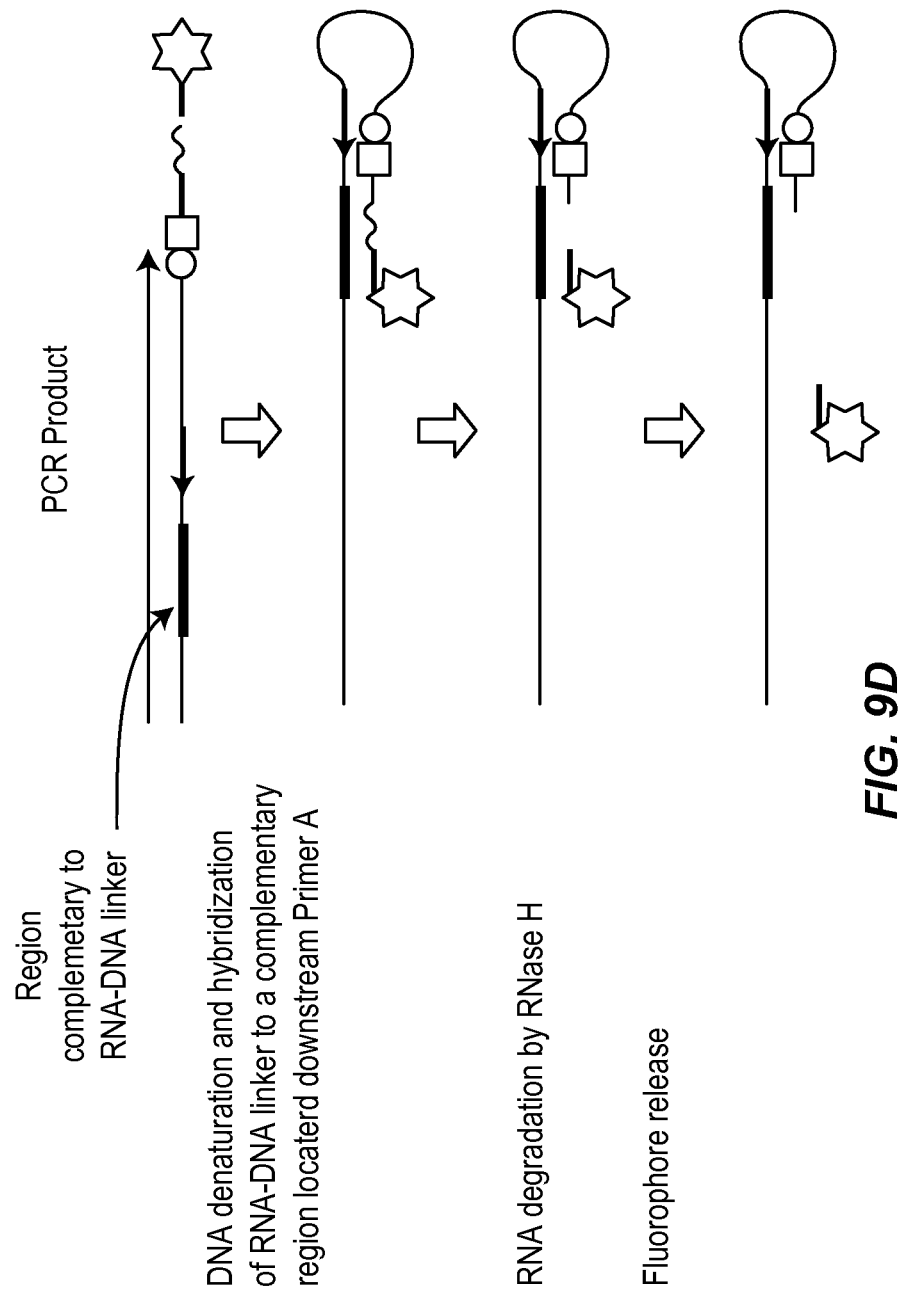

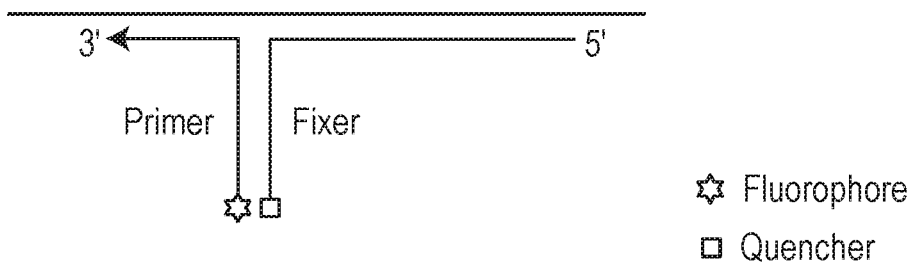
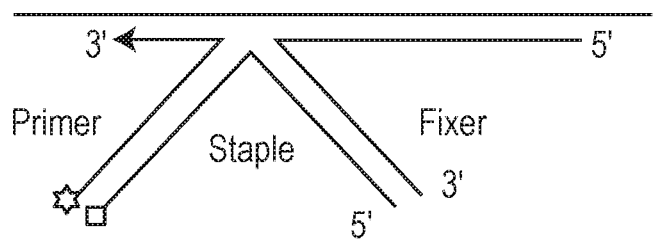
FIG. 10

Modified Primer P1 
Modified Primer MP-P1/AO 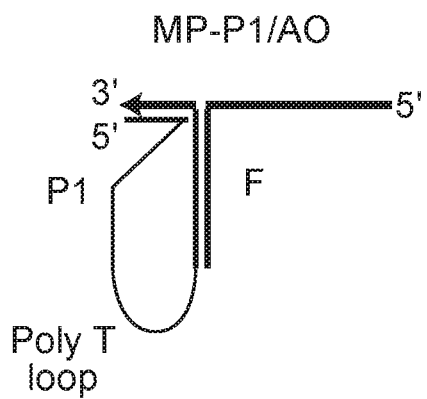
*FIG. 13A*

Step 1: Hybridize Fixer 1 and a mixture of 4 fluorescently labeled Polynucleotides, wash, read the signal (T-base)
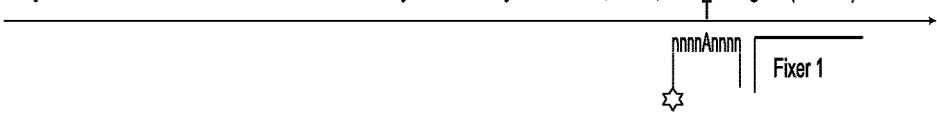

Step 2: Cleave the label, wash, Hybridize a mixture of 4 fluorescently labeled Polynucleotides, wash, read the signal (C)
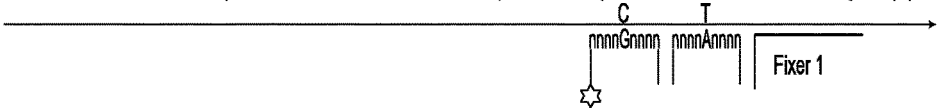

Step 3: Cleave the label, wash, Hybridize a mixture of 4 fluorescently labeled Polynucleotides, wash, read the signal (G)
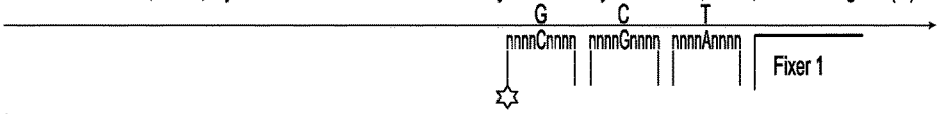

Step 4: Cleave the label, wash, Hybridize a mixture of 4 fluorescently labeled Polynucleotides, wash, read the signal (A)
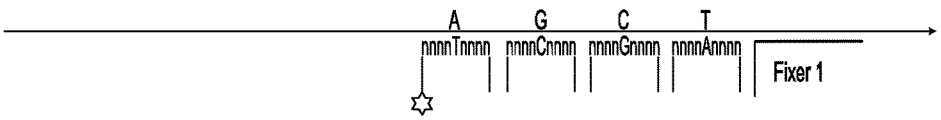

Step 9: Cleave the label, wash, Hybridize a mixture of 4 fluorescently labeled Polynucleotides, wash, read the signal (T)
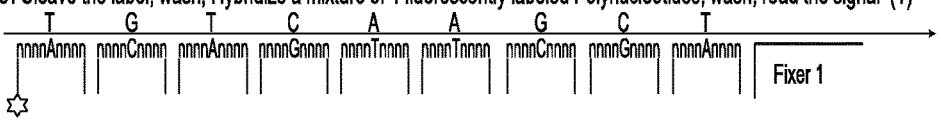

Step 10: Strip Fixer 1 and all hybridized Polynucleotides of the 1st sequencing cycle, then hybridize Fixer 2

Step 11: Hybridize a mixture of 4 fluorescently labeled Polynucleotides, wash, read the signal (C-base)
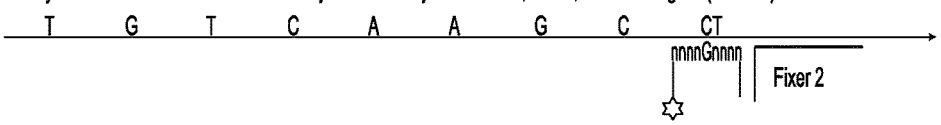

Step 12: Cleave the label, wash, Hybridize a mixture of 4 fluorescently labeled Polynucleotides, wash, read the signal (A)
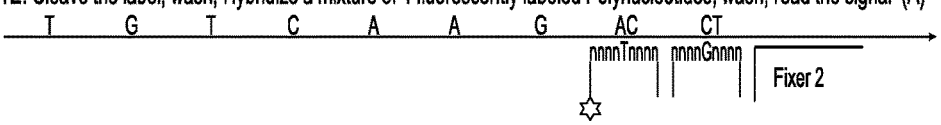

Step 13: Cleave the label, wash, Hybridize a mixture of 4 fluorescently labeled Polynucleotides, wash, read the signal (A)
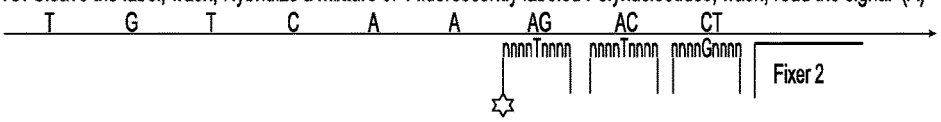

Step 14: Cleave the label, wash, Hybridize a mixture of 4 fluorescently labeled Polynucleotides, wash, read the signal (T)
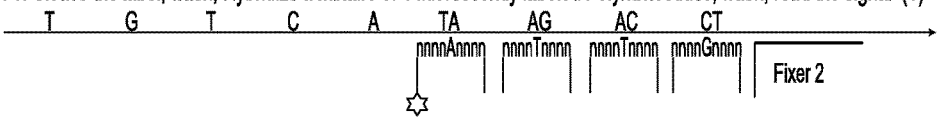

Step 19: Cleave the label, wash, Hybridize a mixture of 4 fluorescently labeled Polynucleotides, wash, read the signal (G)
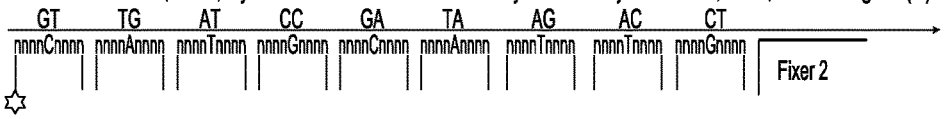

*FIG. 15*

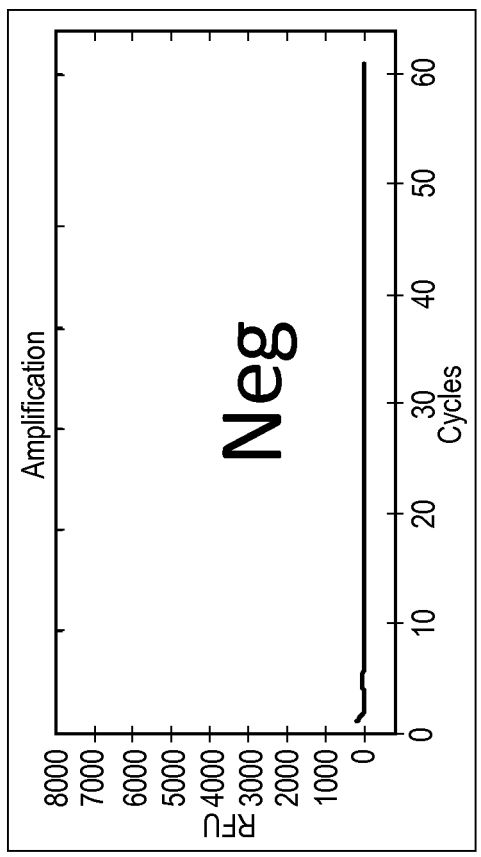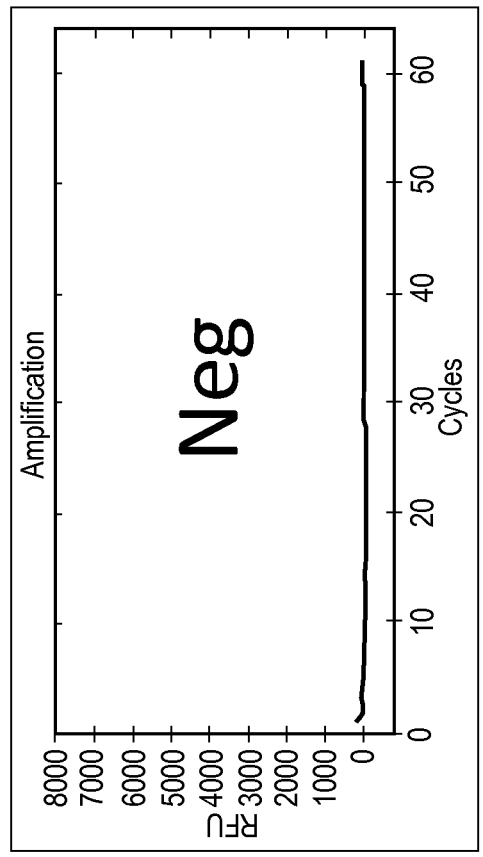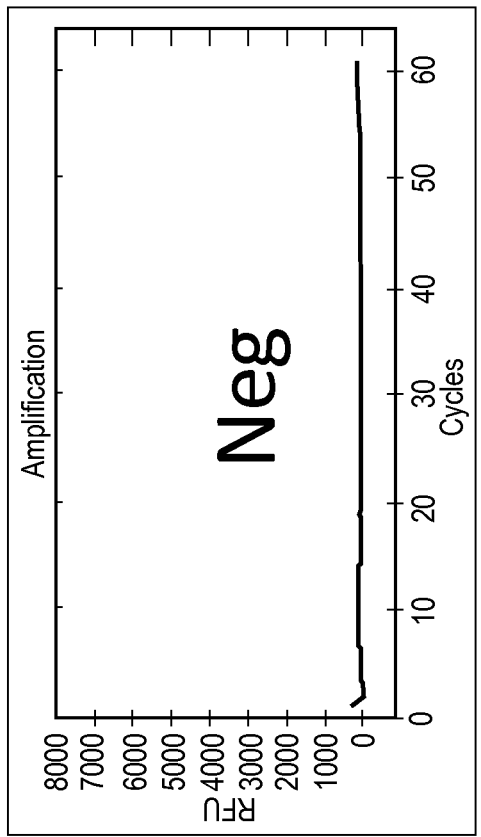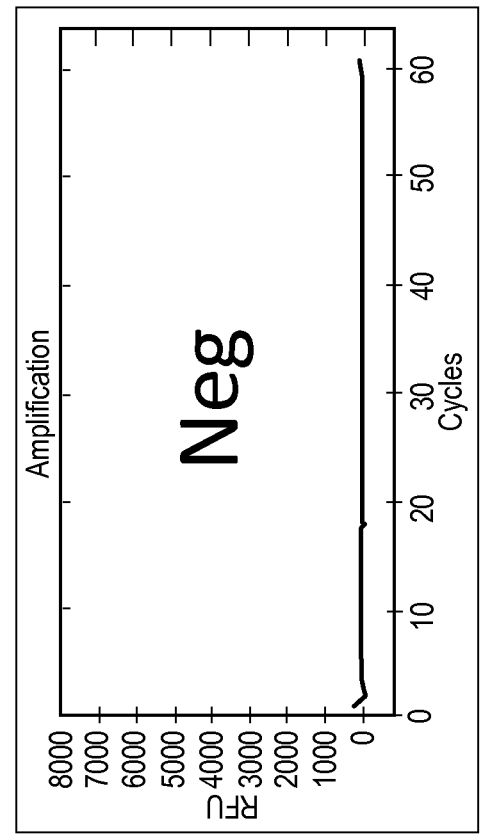
FIG. 24E

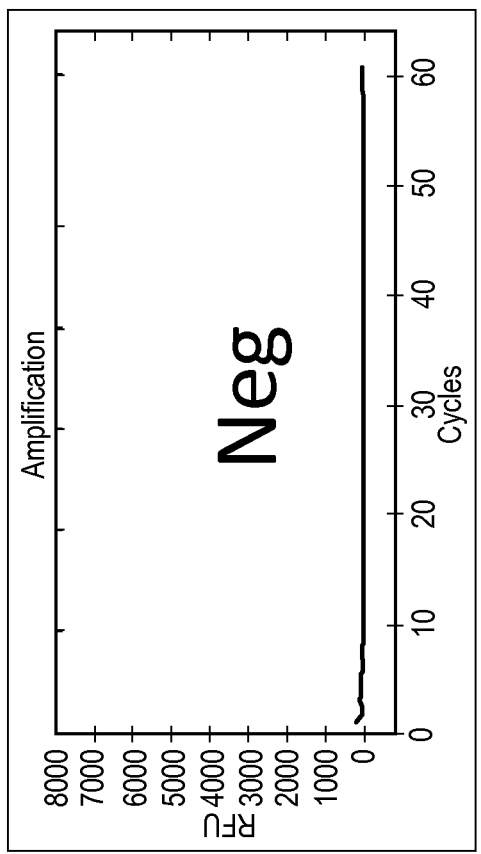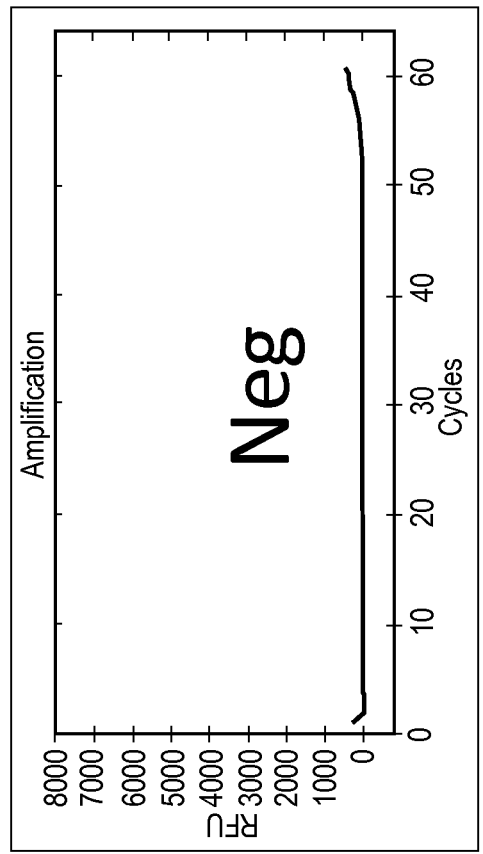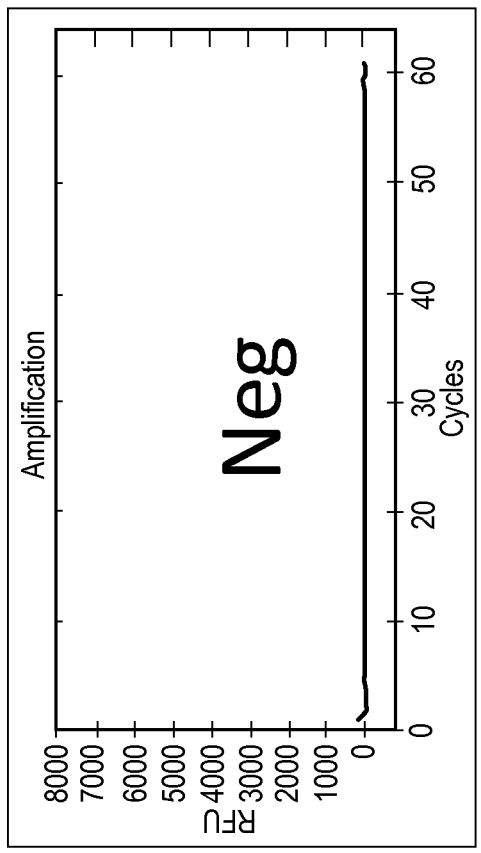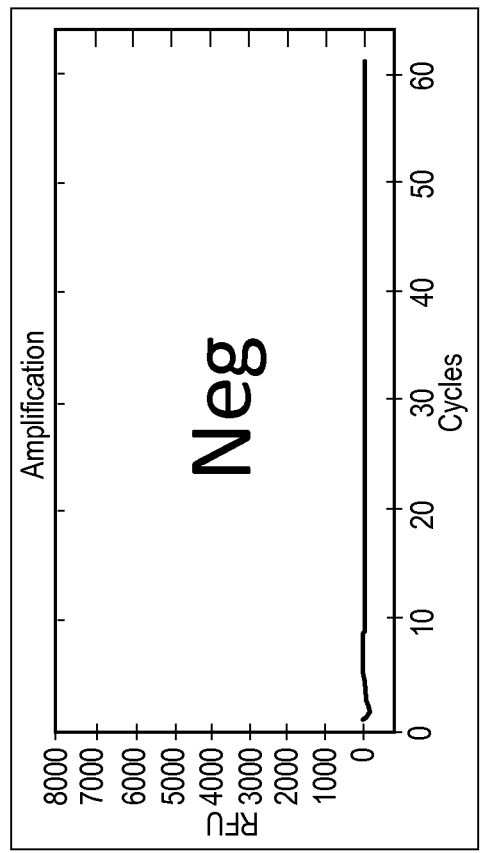
FIG. 24F

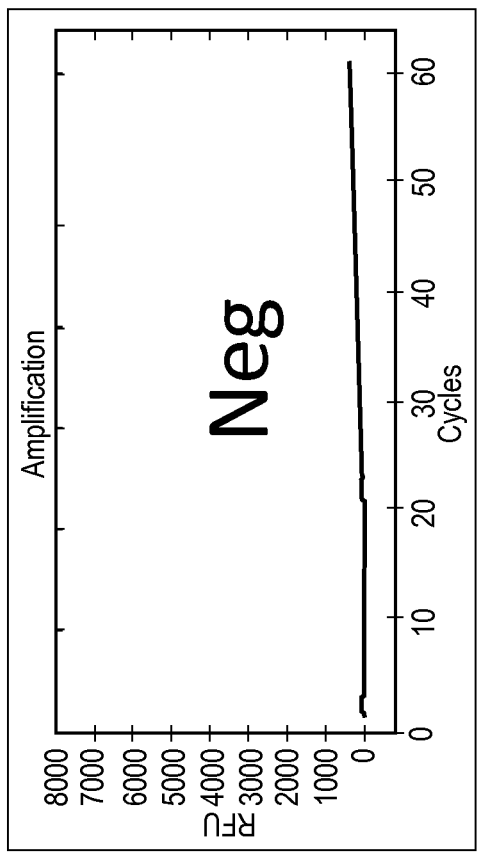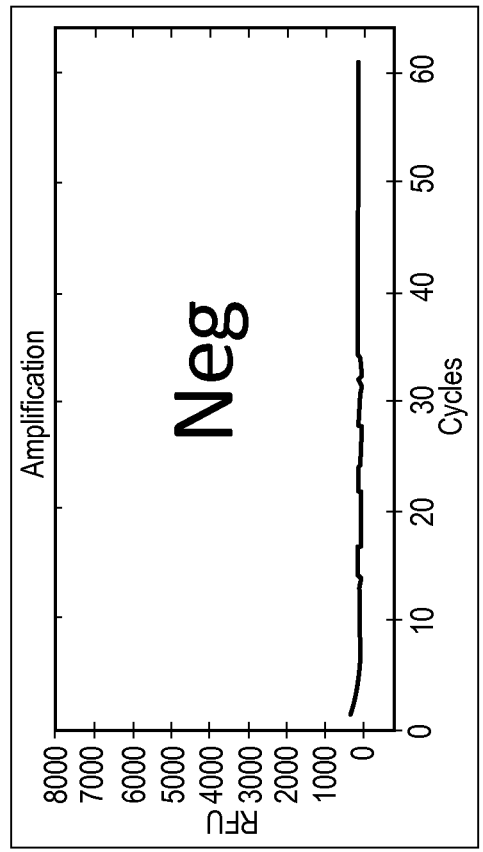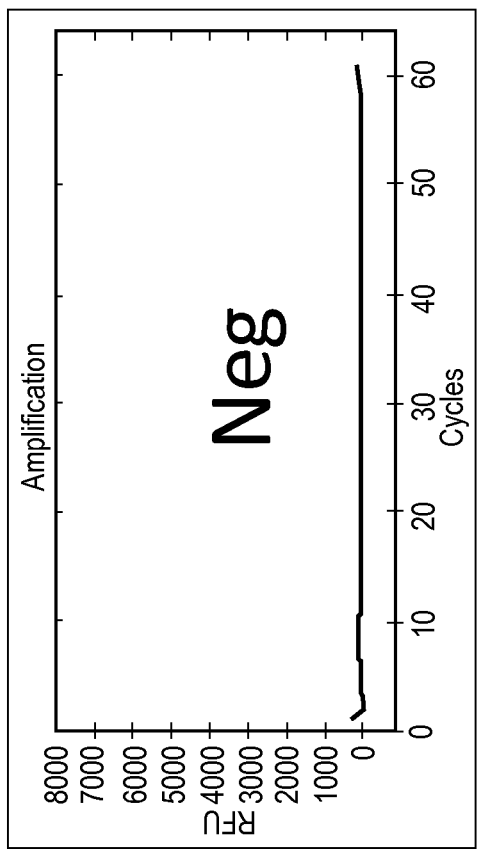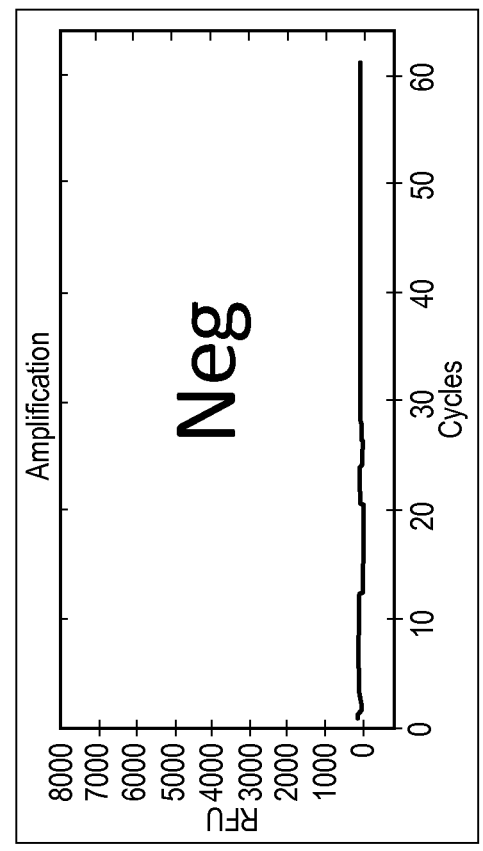
FIG. 24G

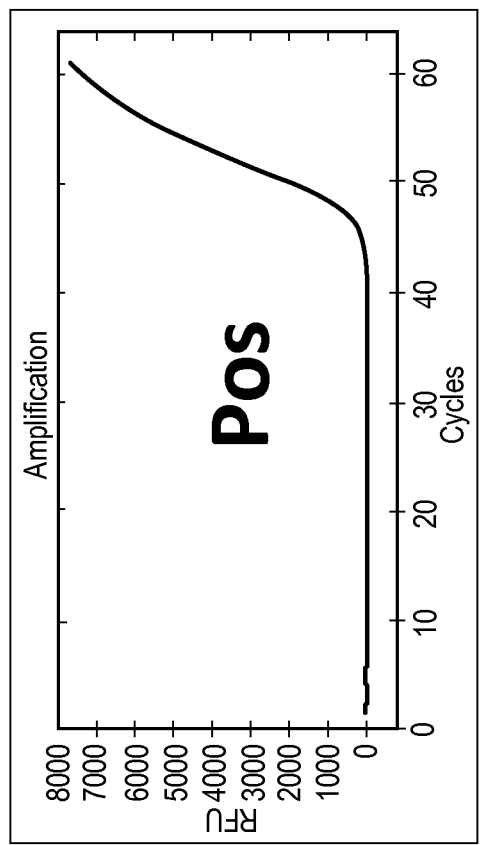
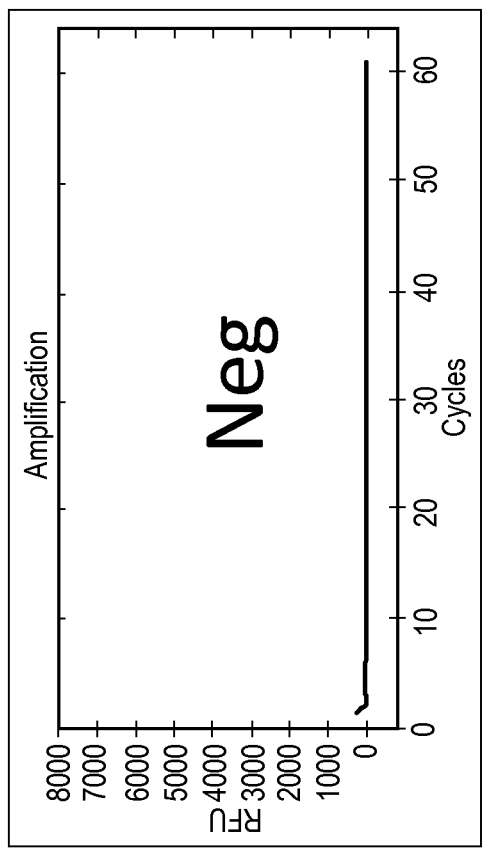
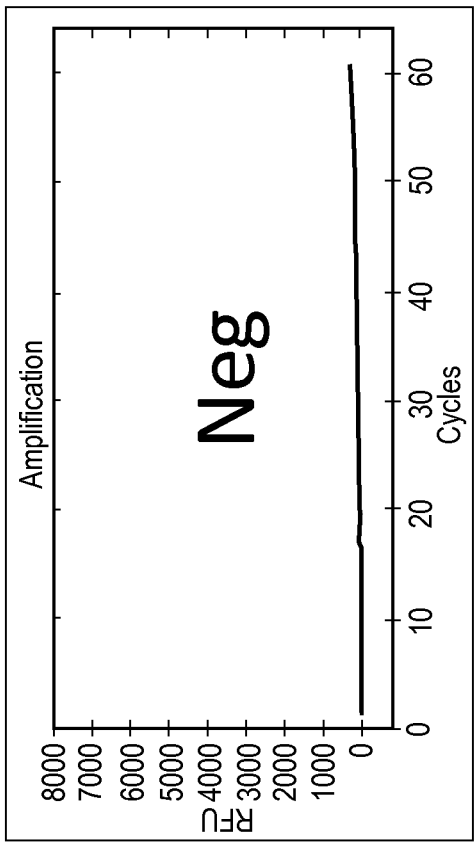
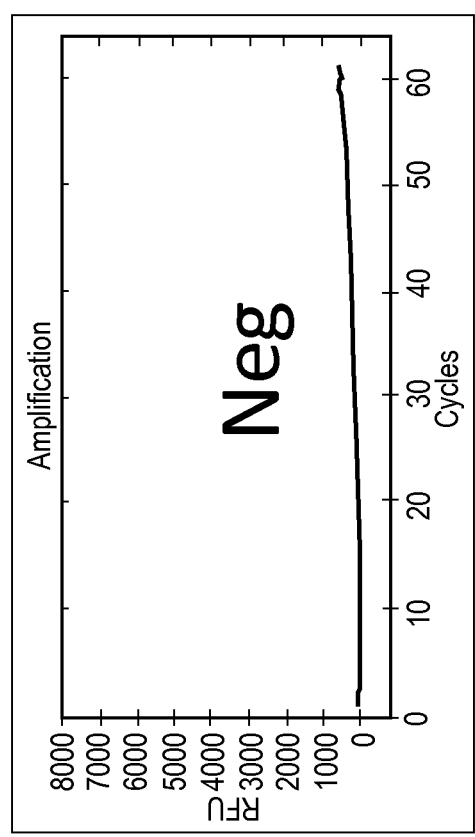
FIG. 24H

```
                       SEQUENCE LISTING

<160> NUMBER OF SEQ ID NOS: 23

<210> SEQ ID NO 1
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 1
ctacagcttc agcgccctga ag                                          22

<210> SEQ ID NO 2
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 2
aagcccttct gcgccgacg                                              19

<210> SEQ ID NO 3
<211> LENGTH: 49
<212> TYPE: DNA
<213> ORGANISM: Artificial Sequence
<220> FEATURE:
<223> OTHER INFORMATION: Synthetic Oligonucleotide

<400> SEQUENCE: 3
aagcccttct gcgccgacgc tgaacaccaa cccaacaacc acaccacaa             49

<210> SEQ ID NO 4
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 4
tggtgtggtt gttgggttgg tgatccacgg                                  30
```

```
<210> SEQ ID NO 5
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 5
caaggcactc ttgcctacgc caa                                              23

<210> SEQ ID NO 6
<211> LENGTH: 31
<212> TYPE: DNA
<213> ORGANISM: Artificial Sequence
<220> FEATURE:
<223> OTHER INFORMATION: Synthetic Oligonucleotide

<400> SEQUENCE: 6
gtgtgacatg ttctaatata gtcacatttt c                                     31

<210> SEQ ID NO 7
<211> LENGTH: 56
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (56)..(56)
<223> OTHER INFORMATION: 3' Phosphate group

<400> SEQUENCE: 7
gaattagctg tatcgtcaag gcactcttgc ccaccaaccc aacaaccaca ccacaa          56

<210> SEQ ID NO 8
<211> LENGTH: 30
<212> TYPE: DNA
<213> ORGANISM: Artificial Sequence
<220> FEATURE:
<223> OTHER INFORMATION: Synthetic Oligonucleotide

<400> SEQUENCE: 8
tggtgtggtt gttgggttgg tgtacgccaa                                       30

<210> SEQ ID NO 9
<211> LENGTH: 43
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (43)..(43)
<223> OTHER INFORMATION: 3' Iowa Black FQ quencher

<400> SEQUENCE: 9
aagcccttct gcgccgacgc tgaacaccaa cccaacaacc ata                        43

<210> SEQ ID NO 10
<211> LENGTH: 27
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5' Fluorescein
```

```
<400> SEQUENCE: 10
tatggttgtt gggttggtga tccacgg                                           27

<210> SEQ ID NO 11
<211> LENGTH: 66
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (66)..(66)
<223> OTHER INFORMATION: 3' Phosphate group

<400> SEQUENCE: 11
aagcccttct gcgccgacgc tgaacaccaa cccaacaacc acaccaactt atcacactac       60
actcac                                                                  66

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (20)..(20)
<223> OTHER INFORMATION: 3' Iowa Black FQ quencher

<400> SEQUENCE: 12
gtgagtgtag tgtgataagt                                                   20

<210> SEQ ID NO 13
<211> LENGTH: 30
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(1)
<223> OTHER INFORMATION: 5' Fluorescein
<220> FEATURE:
<221> NAME/KEY: misc_feature
<222> LOCATION: (1)..(2)
<223> OTHER INFORMATION: Phosphorothioate bond
<220> FEATURE:
<221> NAME/KEY: misc_feature
<222> LOCATION: (2)..(3)
<223> OTHER INFORMATION: Phosphorothioate bond
<220> FEATURE:
<221> NAME/KEY: misc_feature
<222> LOCATION: (3)..(4)
<223> OTHER INFORMATION: Phosphorothioate bond
<220> FEATURE:
<221> NAME/KEY: misc_feature
<222> LOCATION: (4)..(5)
<223> OTHER INFORMATION: Phosphorothioate bond
<220> FEATURE:
<221> NAME/KEY: misc_feature
<222> LOCATION: (5)..(6)
<223> OTHER INFORMATION: Phosphorothioate bond

<400> SEQUENCE: 13
tggtgtggtt gttgggttgg tgatccacgg                                        30

<210> SEQ ID NO 14
<211> LENGTH: 30
<212> TYPE: DNA
<213> ORGANISM: Artificial Sequence
```

```
<220> FEATURE:
<223> OTHER INFORMATION: Synthetic oligonucleotide

<400> SEQUENCE: 14
tggtgtggtt gctgggtatg tgtacgccaa                                        30

<210> SEQ ID NO 15
<211> LENGTH: 53
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (53)..(53)
<223> OTHER INFORMATION: 3' Phosphate group

<400> SEQUENCE: 15
gaattagctg tatcgtcaag gcactcttgc ccacataccc agcaaccaca cca             53

<210> SEQ ID NO 16
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 16
tcttaagcgt cgatggagga gtttg                                             25

<210> SEQ ID NO 17
<211> LENGTH: 58
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (58)..(58)
<223> OTHER INFORMATION: 3' Phosphate group

<400> SEQUENCE: 17
ctgctgaaaa tgactgaata taaacttgtg gtagttactt ctcatccctg cgtctctg        58

<210> SEQ ID NO 18
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 18
cagagacgca gggatgagaa gtggagctgt                                        30

<210> SEQ ID NO 19
<211> LENGTH: 26
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' Fluorescein
<220> FEATURE:
<221> NAME/KEY: misc_feature
<222> LOCATION: (9)..(10)
<223> OTHER INFORMATION: Internal Zen Quencher
<220> FEATURE:
```

```
<221> NAME/KEY: misc_feature
<222> LOCATION: (26)..(26)
<223> OTHER INFORMATION: 3' Iowa Black FQ Quencher

<400> SEQUENCE: 19
acgatacacg tctgcagtca actgga                                         26

<210> SEQ ID NO 20
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 20
ttgttggatc atattcgtcc acaaaatg                                       28

<210> SEQ ID NO 21
<211> LENGTH: 26
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(1)
<223> OTHER INFORMATION: 5' Fluorescein
<220> FEATURE:
<221> NAME/KEY: misc_feature
<222> LOCATION: (9)..(10)
<223> OTHER INFORMATION: Internal Zen Quencher
<220> FEATURE:
<221> NAME/KEY: misc_feature
<222> LOCATION: (26)..(26)
<223> OTHER INFORMATION: 3' Iowa Black Quencher

<400> SEQUENCE: 21
agctgtatcg tcaaggcact cttgcc                                         26

<210> SEQ ID NO 22
<211> LENGTH: 23
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (23)..(23)
<223> OTHER INFORMATION: 3' Phosphate group

<400> SEQUENCE: 22
gtggcgtagg caagagtgcc ttg                                            23

<210> SEQ ID NO 23
<211> LENGTH: 30
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (30)..(30)
<223> OTHER INFORMATION: LNA modified nucleotide

<400> SEQUENCE: 23
cagagacgca gggatgagaa gtggagctgt                                     30
```

POLYNUCLEOTIDE PRIMERS AND PROBES

CROSS REFERENCE TO RELATED APPLICATION

This application is a continuation of U.S. patent application Ser. No. 12/913,742, filed Oct. 27, 2010, which claims priority to U.S. Provisional Patent Application No. 61/255,461, filed Oct. 27, 2009, the disclosures of which are incorporated herein by reference in their entirety.

FIELD OF THE INVENTION

The invention relates to polynucleotide combinations and their use.

BACKGROUND

Detection and amplification of nucleic acids play important roles in genetic analysis, molecular diagnostics, and drug discovery. Many such applications require specific, sensitive and inexpensive quantitative detection of certain DNA or RNA molecules, gene expression, DNA mutations or DNA methylation present in a small fraction of total polynucleotides. Many current methods use polymerase chain reaction, or PCR, and specifically, real-time PCR (quantitative, or qPCR) to detect and quantify very small amounts of DNA or RNA from clinical samples.

While the performance of current PCR assays is constantly improving, their sensitivity, specificity and cost are still far away from becoming a widely acceptable diagnostic test. Indeed, many PCR methods currently used in the art suffer from technical limitations that make the methods inadequate for many practical applications. For example, in instances where the target molecule has secondary structure that inhibits or even completely prevents binding of one or both primers to the target, amplification can be reduced or even non-existent, which, for example, from a diagnostic standpoint could give rise to a false negative despite use of a highly specific primer with binding properties that would be expected to be sensitive. Other challenges include low sensitivity of current real-time PCR assays in detection and discrimination of rare DNA molecules with a single base mutation in situations when they mixed with thousands of non-mutated DNA molecules, and ability to combine multiple mutation detection assays into one multiplex diagnostic assay.

There thus remains a need in the art for a development of amplification primers that combines high binding specificity with low synthesis cost that retain the ability to overcome technical problems recognized in the art, including novel application of PCR for diagnostics using next generation sequencing platforms.

SUMMARY OF THE INVENTION

In one aspect, the disclosure provides a polynucleotide primer combination comprising a first polynucleotide and a second polynucleotide, wherein the first polynucleotide (P) comprises a first domain (Pa) having a sequence that is complementary to a first target polynucleotide region ($T_1$) and a second domain (Pc) comprises a unique polynucleotide sequence, and the second polynucleotide (F) comprises a first domain (Fb) having a sequence that is complementary to a second target polynucleotide region ($T_2$) and a second domain (Fd) comprising a polynucleotide sequence sufficiently complementary to Pc such that Pc and Fd will hybridize under appropriate conditions, and wherein the target polynucleotide has a secondary structure that is denatured by hybridization of Fb to the target polynucleotide. In one aspect, the secondary structure of the target polynucleotide inhibits polymerase extension of the target polynucleotide in the absence of F. The disclosure further contemplates an aspect wherein the polynucleotide primer combination P and/or F further comprise a modified nucleic acid.

The disclosure further provides a polynucleotide primer combination comprising a first polynucleotide and a second polynucleotide, wherein the first polynucleotide (P) comprises a first domain (Pa) having a sequence that is complementary to a first target polynucleotide region ($T_1$) and a second domain (Pc) comprising a unique polynucleotide sequence, and the second polynucleotide (F) comprises a first domain (Fb) having a sequence that is complementary to a second target polynucleotide region ($T_2$) and a second domain (Fd) comprising a polynucleotide sequence sufficiently complementary to Pc such that Pc and Fd will hybridize under appropriate conditions, and wherein P and/or F further comprise a modified nucleic acid.

A polynucleotide primer combination is also provided comprising a first polynucleotide, a second polynucleotide, and a blocker polynucleotide, the first polynucleotide (P) comprising a first domain (Pa) having a sequence that is complementary to a first target polynucleotide region ($T_1$) and a second domain (Pc) comprising a unique polynucleotide sequence, the second polynucleotide (F) comprising a first domain (Fb) having a sequence that is complementary to a second target polynucleotide region ($T_2$) and a second domain (Fd) comprising a polynucleotide sequence sufficiently complementary to Pc such that Pc and Fd will hybridize under appropriate conditions, and the blocker polynucleotide comprising a nucleotide sequence that is complementary to a third target polynucleotide region ($T_3$), wherein $T_3$ is located 5' of $T_1$ and $T_2$. In an aspect of the primer combination, a nucleotide at the 3' end of P and a nucleotide at the 5' end of the blocker polynucleotide overlap. In another aspect, the blocker polynucleotide has a sequence that overlaps Pa over the whole length of Pa. In still another aspect, the nucleotide at the 3' end of P and the nucleotide at the 5' end of the blocker polynucleotide are different. In each of these aspects, an embodiment is contemplated wherein P, F, and/or the blocker polynucleotide comprises a modified nucleic acid.

The disclosure further provides a polynucleotide primer combination comprising a first polynucleotide, a second polynucleotide, and a probe polynucleotide, the first polynucleotide comprising a first domain (Pa) that is complementary to a first target polynucleotide region ($T_1$) and a second domain (Pc) comprising a unique polynucleotide sequence, the second polynucleotide (F) comprising a first domain (Fb) that is complementary to a second target polynucleotide region ($T_2$) and a second domain (Fd) comprising a polynucleotide sequence sufficiently complementary to Pc such that Pc and Fd will hybridize under appropriate conditions, and the probe polynucleotide comprising a nucleotide sequence that is complementary to a third target polynucleotide region ($T_4$), wherein $T_4$ is located 5' of $T_1$ and $T_2$. In certain aspects, the probe polynucleotide comprises a label and a quencher. In other aspects, P, F and/or the probe polynucleotide comprise a modified nucleic acid. An embodiment is also provide wherein the polynucleotide primer combination further comprises a blocker polynucleotide, wherein the blocker polynucleotide comprises a nucleotide sequence that is complementary to a fourth target polynucleotide region (T$_3$), and wherein T$_3$ is located 5' of T$_1$ and T$_2$ and 3' of T$_4$. In one aspect, the blocker comprises a modified nucleic acid.

Also provided is a polynucleotide primer combination comprising a first polynucleotide, a second polynucleotide, and a universal quencher polynucleotide, the first polynucleotide (P) comprising a first domain (Pa) that is complementary to a first target polynucleotide region (T$_1$), a second domain (Pc) comprising a unique polynucleotide sequence, and a label at its 5' end, the second polynucleotide (F) comprising a first domain (Fb) that is complementary to a second target polynucleotide region (T$_2$) and a second domain (Fd) comprising two polynucleotide sequences, a 5' polynucleotide sequence that is sufficiently complementary to the 5' sequence of Pc such that the 5' polynucleotide sequence of Pc and Fd will hybridize under appropriate conditions, and a 3' polynucleotide sequence that is sufficiently complementary to the universal quencher polynucleotide such that the 3' polynucleotide sequence of Fd and the universal quencher will hybridize under appropriate conditions, and the universal quencher polynucleotide comprising a quencher and a nucleotide sequence that is sufficiently complementary to the 3' polynucleotide sequence of Fd such that the universal quencher polynucleotide and the 3' polynucleotide sequence of Fd will hybridize under appropriate conditions. In one aspect, P, F and/or the universal quencher polynucleotide comprise a modified nucleic acid. In another aspect, the polynucleotide primer combination further comprises a reverse primer, wherein the reverse primer comprises a polynucleotide sequence complementary to a polynucleotide strand comprising a sequence that hybridizes to T$_1$.

In various aspects of any of the primer combinations provided herein, P comprises a modified nucleic acid. In other aspects, F further comprises a modified nucleic acid, and in certain of these aspects, the modified nucleic acid is in Pa, and/or the modified nucleic acid is in Fb.

In each polynucleotide primer combination of the disclosure, as aspect is provided wherein P comprises a plurality of modified nucleic acids in Pa, and/or wherein F comprises a plurality of modified nucleic acids in Fb. When P comprises a modified nucleic acid, as aspect is provided wherein the modified nucleic acid is the nucleotide at a 3' end of P.

In each primer combination disclosed, a aspects are provided wherein Fd is at least 70% complementary to Pc, wherein Pc is at least 70% complementary to Fd, wherein Pc and Fd hybridize to each other in the absence of the template polynucleotide, wherein P is DNA, modified DNA, RNA, modified RNA, peptide nucleic acid (PNA), or combinations thereof, and/or wherein F is DNA, modified DNA, RNA, modified RNA, peptide nucleic acid (PNA), or combinations thereof.

In each primer pair combination, an aspect is provided wherein the polynucleotide primer combination further comprises a blocking group attached to F at its 3' end which blocks extension from a DNA polymerase. In this aspect, an embodiment is provided wherein the blocking group is selected from the group consisting of a 3' phosphate group, a 3' amino group, a dideoxy nucleotide, and an inverted deoxythymidine (dT).

In another aspect of each primer pair combinations, certain embodiments are provided wherein Pa is from about 5 bases in length to about 30 bases in length, about 5 bases in length to about 20 bases in length, about 5 bases in length to about 15 bases in length, about 5 bases in length to about 10 bases in length, about 5 bases in length to about 8 bases in length. In other aspects, Pc is from about 5 bases in length to about 200 bases in length, about 5 bases in length to about 150 bases in length, about 5 bases in length to about 100 bases in length, about 5 bases in length to about 50 bases in length, about 5 bases in length to about 45 bases in length, about 5 bases in length to about 40 bases in length, about 5 bases in length to about 35 bases in length, about 5 bases in length to about 30 bases in length, about 5 bases in length to about 25 bases in length, about 5 bases in length to about 20 bases in length, about 5 bases in length to about 15 bases in length, about 10 to about 50 bases in length, about 10 bases in length to about 45 bases in length, about 10 bases in length to about 40 bases in length, about 10 bases in length to about 35 bases in length, about 10 bases in length to about 30 bases in length, about 10 bases in length to about 25 bases in length, about 10 bases in length to about 20 bases in length, or about 10 bases in length to about 15 bases in length. In still other aspects, Fb is from about 10 bases in length to about 5000 bases in length, about 10 bases in length to about 4000 bases in length, about 10 bases in length to about 3000 bases in length, about 10 bases in length to about 2000 bases in length, about 10 bases in length to about 1000 bases in length, about 10 bases in length to about 500 bases in length, about 10 bases in length to about 250 bases in length, about 10 bases in length to about 200 bases in length, about 10 bases in length to about 150 bases in length, about 10 bases in length to about 100 bases in length, about 10 bases in length to about 95 bases in length, about 10 bases in length to about 90 bases in length, about 10 bases in length to about 85 bases in length, about 10 bases in length to about 80 bases in length, about 10 bases in length to about 75 bases in length, about 10 bases in length to about 70 bases in length, about 10 bases in length to about 65 bases in length, about 10 bases in length to about 60 bases in length, about 10 bases in length to about 55 bases in length, about 10 bases in length to about 50 bases in length, about 10 bases in length to about 45 bases in length, about 10 bases in length to about 40 bases in length, about 10 bases in length to about 35 bases in length, about 10 bases in length to about 30 bases in length, or about 10 bases in length to about 100 bases in length. In yet other aspects, Fd is from about 5 bases in length to about 200 bases in length, about 5 bases in length to about 150 bases in length, about 5 bases in length to about 100 bases in length, about 5 bases in length to about 50 bases in length, about 5 bases in length to about 45 bases in length, about 5 bases in length to about 40 bases in length, about 5 bases in length to about 35 bases in length, about 5 bases in length to about 30 bases in length, about 5 bases in length to about 25 bases in length, about 5 bases in length to about 20 bases in length, about 5 bases in length to about 15 bases in length, about 10 to about 50 bases in length, about 10 bases in length to about 45 bases in length, about 10 bases in length to about 40 bases in length, about 10 bases in length to about 35 bases in length, about 10 bases in length to about 30 bases in length, about 10 bases in length to about 25 bases in length, about 10 bases in length to about 20 bases in length, or about 10 bases in length to about 15 bases in length.

In each aspect of the primer pair combination provide, an embodiment includes that wherein P comprises a label. In some aspects, the label is located in P at its 5' end and/or the label is quenchable. In some aspects of these embodiments, F comprises a quencher and/or the quencher is located in F at its 3' end. In specific embodiments, the quencher is selected from the group consisting of Black Hole Quencher 1, Black Hole Quencher-2, Iowa Black FQ, Iowa Black RQ, and Dabcyl. G-base.

In certain primer pair combinations comprising a modified nucleic acid, the modified nucleic acid in the blocker polynucleotide is the nucleotide at the 5' end of the blocker polynucleotide, the modified nucleic acid is the nucleotide at the 3' end of P, and/or the modified nucleic acid is a locked nucleic acid.

The disclosure further provides a method of detecting the presence of a target polynucleotide in a sample with a primer combination, the primer combination comprising a first polynucleotide and a second polynucleotide, the first polynucleotide (P) comprising a first domain (Pa) having a sequence that is fully complementary to a first target polynucleotide region ($T_1$) and a second domain (Pc) comprising a unique polynucleotide sequence, Pa having a sequence that is not fully complementary to a non-target polynucleotide in the sample and the second polynucleotide (F) comprising a first domain (Fb) that is complementary to a second target polynucleotide region ($T_2$) and a second domain (Fd) comprising a polynucleotide sequence sufficiently complementary to Pc such that Pc and Fd will hybridize under appropriate conditions, the method comprising the steps of: contacting the sample with the primer combination and a polymerase under conditions that allow extension of a sequence from Pa which is complementary to the target polynucleotide when the target polynucleotide is present in the sample and detecting the sequence extended from Pa indicating the presence of the target polynucleotide in the sample. In certain aspects, the method provides a change in sequence detection from a sample with a non-target polynucleotide compared to sequence detection from a sample with a target polynucleotide.

Also provided is a method of detecting the presence of a target polynucleotide in a sample with a primer combination as disclosed herein wherein P comprises a first domain that is fully complementary to $T_1$ and wherein Pa is not fully complementary to a non-target polynucleotide in the sample, the method comprising the steps of: contacting the sample with the primer combination and a polymerase under conditions that allow extension of a sequence from Pa which is complementary to the target polynucleotide when the target polynucleotide is present in the sample and detecting the sequence extended from Pa, wherein detection indicates the presence of the target polynucleotide in the sample. In some aspects, the method provides a change in sequence detection from a sample with a non-target polynucleotide compared to sequence detection from a sample with a target polynucleotide.

In each of these methods, an embodiment is provided wherein the detecting step is carried out using polymerase chain reaction. In these embodiments, aspects are provided wherein the polymerase chain reaction utilizes P of the primer combination and a reverse primer, the reverse primer having a sequence complementary to the sequence extended from Pa and/or the polymerase chain reaction utilizes a reverse primer complementary to the sequence extended from Pa and a forward primer having a sequence complementary to the strand of the target polynucleotide to which Pa hybridizes.

On another aspect of these methods, detection is carried out in real time.

The disclosure further provides a method of initiating polymerase extension on a target polynucleotide in a sample using a primer combination, the primer combination comprising a first polynucleotide and a second polynucleotide, the first polynucleotide (P) comprising a first domain (Pa) having a sequence that is fully complementary to a first target polynucleotide region ($T_1$) and a second domain (Pc) comprising a unique polynucleotide sequence, Pa having a sequence that is not fully complementary to a non-target polynucleotide in the sample and the second polynucleotide (F) comprising a first domain (Fb) that is complementary to a second target polynucleotide region ($T_2$) and a second domain (Fd) comprising a polynucleotide sequence sufficiently complementary to Pc such that Pc and Fd will hybridize under appropriate conditions, wherein the sample comprises a mixture of (i) a target polynucleotide that has a sequence ($T_1$) in a first region that is fully complementary to the sequence in Pa and (ii) a non-target polynucleotide that has a sequence ($T_1^*$) in a first region that is not fully complementary to Pa, the method comprising the step of contacting the sample with the primer combination and a polymerase under conditions that allow extension of a sequence from Pa and complementary to the target polynucleotide strand when Pa contacts $T_1$. In certain aspects of the method, the sequence in the first region ($T_1$) in the target polynucleotide differs from the sequence in the first region ($T_1^*$) in the non-target polynucleotide at one base. In other aspect, the method further comprises the step of detecting the sequence extended from Pa, wherein detection indicates the presence of the target polynucleotide in the sample.

The disclosure also provides a method of initiating polymerase extension on a target polynucleotide in a sample using a primer combination as disclosed herein, wherein P comprises a first domain (Pa) that is fully complementary to a first target polynucleotide region ($T_1$) and wherein Pa is not fully complementary to a non-target polynucleotide in the sample, the method comprising the steps of: contacting the sample with the primer combination and a polymerase under conditions that allow extension of a sequence from Pa which is complementary to the target polynucleotide when the target polynucleotide is present in the sample. In some aspects, the method further comprises the step of detecting the sequence extended from Pa, indicating the presence of the target polynucleotide in the sample. In various embodiments, the detecting step is carried out using polymerase chain reaction, and in certain aspects of this embodiment, the polymerase chain reaction utilizes P of the primer combination and a reverse primer, the reverse primer having a sequence complementary to the sequence extended from Pa, and/or the polymerase chain reaction utilizes a reverse primer complementary to the sequence extended from Pa and a forward primer having a sequence complementary to the strand of the target polynucleotide to which Pa hybridizes. In each embodiment of the method, an aspect is provided wherein detecting is carried out in real time.

Also provided is a method of amplifying a target polynucleotide in a sample using a polynucleotide primer combination, the primer combination comprising a first polynucleotide and a second polynucleotide, the first polynucleotide (P) comprising a first domain (Pa) having a sequence that is fully complementary to a first target polynucleotide region ($T_1$) and a second domain (Pc) comprising a unique polynucleotide sequence, Pa having a sequence that is not fully complementary to a non-target polynucleotide in the sample and the second polynucleotide (F) comprising a first domain (Fb) that is complementary to a second target polynucleotide region ($T_2$) and a second domain (Fd) comprising a polynucleotide sequence sufficiently complementary to Pc such that Pc and Fd will hybridize under appropriate conditions, wherein the sample comprises a mixture of (i) a target polynucleotide that has a sequence in a first region ($T_1$) that is fully complementary to the sequence in Pa and (ii) one or more non-target polynucleotides that are not fully complementary to Pa; the method comprising the steps of: (a) contacting the sample with the primer combination and a polymerase under conditions that allow extension of a sequence from Pa which is complementary to the target polynucleotide when the target polynucleotide is present in the sample, (b) denaturing the sequence extended from Pa from the target polynucleotide, and (c) repeating step (a) in the presence of a reverse primer having a sequence complementary to a region in the sequence extended from Pa in step (b) to amplify the target polynucleotide, wherein extension and amplification of the target polynucleotide occurs when Pa is fully complementary to the sequence in the Pa but is less efficient or does not occur when the first region in the target polynucleotide is not fully complementary to the sequence in Pa.

The disclosure also provides a method of amplifying a target polynucleotide in a sample using a polynucleotide primer combination as disclosed herein, wherein the first polynucleotide (P) comprises a first domain (Pa) that is fully complementary to a first target polynucleotide region ($T_1$) and wherein Pa is not fully complementary to a non-target polynucleotide in the sample, the method comprising the steps of: (a) contacting the sample with the primer combination and a polymerase under conditions that allow extension of a sequence from Pa which is complementary to the target polynucleotide when the target polynucleotide is present in the sample, (b) denaturing the sequence extended from Pa from the target polynucleotide, and (c) repeating step (a) in the presence of a reverse primer having a sequence complementary to a region in the sequence extended from Pa in step (b) to amplify the target polynucleotide, wherein extension and amplification of the target polynucleotide occurs when $T_1$ is fully complementary to the sequence in Pa but is less efficient or does not occur when the first region in the target polynucleotide is not fully complementary to the sequence in Pa. In some aspects of the methods, the reverse primer has a sequence that is fully complementary to a region in the sequence extended from Pa. In other aspects, the reverse primer is a primer combination comprising a first polynucleotide and a second polynucleotide, the first polynucleotide (PP) comprising a first domain (PPa) having a sequence that is fully complementary to a first region ($TT_1$) in the sequence extended from Pa in step (a) and a second domain (PPc) comprising a unique polynucleotide sequence, and the second polynucleotide (FF) comprising a first domain (FFb) that is complementary to a second region ($TT_2$) in the sequence extended from Pa in step (a) and a second domain (FFd) comprising a polynucleotide sequence sufficiently complementary to PPc such that PPc and FFd will hybridize under appropriate conditions. In certain aspects, the methods further comprise the step of detecting a product amplified in the method, and in other aspects, detection is carried out using polymerase chain reaction, and/or detection is carried out in real time.

In each method of the disclosure, an aspect is provided wherein the reverse primer is a primer combination as disclosed herein.

BRIEF DESCRIPTION OF THE DRAWINGS

FIG. 2 depicts a primer combination comprising two three-way junctions with three target binding domains a, g, and b.

FIG. 3 depicts polynucleotide combinations with stable four-way (A) and five-way (B) junctions with two target binding domains.

FIG. 4 depicts a primer combination with a blocker polynucleotide. As depicted in FIG. 4A, the 5' base of the blocker polynucleotide overlaps with, and is different than, the 3' base of the first polynucleotide. The 5' base of the blocker polynucleotide is not complementary to the target polynucleotide and is displaced upon extension of the first polynucleotide by a polymerase. As depicted in FIG. 4B, the 5' base of the blocker polynucleotide overlaps with, and is different than, the 3' base of the first polynucleotide. The 5' base of the blocker polynucleotide is 100% complementary to the non-target polynucleotide while the 3' base of the first polynucleotide is not complementary to the non-target polynucleotide. In this configuration, the blocker polynucleotide blocks extension of the first polynucleotide by a polymerase.

FIG. 5 depicts a primer combination with a probe polynucleotide. As depicted in FIG. 5A, the probe polynucleotide comprises a label at its 5' end and a quencher at its 3' end. FIG. 5B depicts the structural relationship of a probe polynucleotide in combination with a first/second polynucleotide pair and a blocker polynucleotide.

FIGS. 7A-7F are schematics illustrating the polynucleotide combinations as used in the polymerase chain reaction (PCR).

In FIG. 8A, the reverse primer is a single polynucleotide. In FIG. 8B, the reverse primer is a second set of first and second polynucleotides.

FIG. 9D illustrates the use of the combination depicted in FIG. 9C in PCR. When the PCR product comprising Primer A is denatured, the RNA-DNA linker hybridizes to a region downstream of Primer A, RNase H cleaves the RNA-DNA hybrid and releases the fluorophore and a sequence-specific fluorescent signal is detected.

FIG. 10 depicts primer combinations with three-way or four-way junctions for use in real-time PCR. With three-way junction primers, the primer polynucleotide (i.e., first polynucleotide) is labeled with a fluorophore on its 5' end, and the fixer polynucleotide (i.e., second polynucleotide) is labeled with a quencher on its 3' end. With four-way junction primers, the primer polynucleotide is labeled with a fluorophore on its 5' end, and the staple is labeled with a quencher on its 3' end. The fixer polynucleotide is unlabeled. Since the second domain regions of both the primer and fixer polynucleotides are unique, the staple polynucleotide can be used as a "universal" quencher polynucleotide.

FIGS. 13A-13C depict polynucleotide combinations constructed with a modified primer polynucleotide ("P1") and a basic fixer polynucleotide ("F"). In FIG. 13, the modified primer polynucleotide is shown on the left, with the complete polynucleotide combination (modified primer polynucleotide and basic fixer polynucleotide) shown on the right.

FIG. 15 depicts the use of a polynucleotide combination (i.e., first polynucleotide and second polynucleotide) to perform next generation sequencing (NGS).

FIGS. 24E-24H illustrate the results of a qPCR assay to detect mutant KRAS G12V in a mixture with no copies of KRAS G12V DNA using a first polynucleotide modified with LNA at its 3' end, a Fixer (i.e., second polynucleotide), a Probe Polynucleotide (i.e., TaqMan), and a blocker polynucleotide. 94% of WT DNA samples (15 out of 16) showed no signal, indicating a very high selectivity of single mutant DNA detection by the improved KRAS G12V qPCR mutation assay.

DETAILED DESCRIPTION OF THE INVENTION

Figure 1:
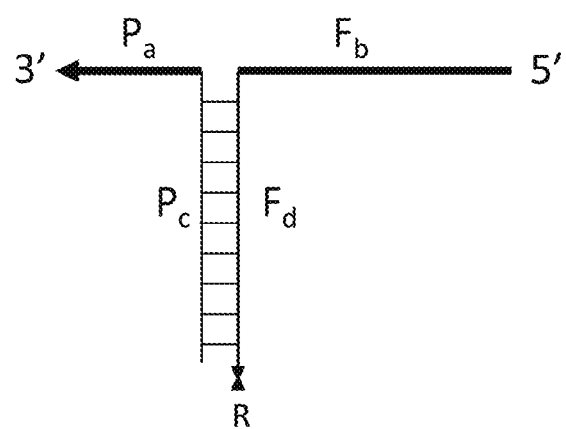
FIG. 1 depicts the structural relationship of the basic polynucleotide combination (i.e., first polynucleotide and second polynucleotide) disclosed herein.

The invention is based on the discovery of a discontinuous polynucleotide design that overcomes problems encountered during the hybridization of polynucleotides, and in particular, amplification primer hybridization to a target polynucleotide. These problems include but are not limited to surmounting difficult secondary structure in the target polynucleotide and a low specificity to single-base changes in a target polynucleotide.

Polynucleotide combinations described herein offer an advantage over both standard PCR primers and long PCR primers when using polynucleotide templates that are difficult to amplify efficiently. Such templates include, for example, those that contain a degree of secondary structure formed through internal self-hybridization giving rise to, for example, loops, hairpins and the like, that preclude, cause to be less efficient or inhibit hybridization to a complementary sequence. Template secondary structure can prevent priming with a standard PCR primer which is unable to destabilize the internal hybridization and thus is unable to hybridize to the primer complement. Using polynucleotide combinations of the invention, template secondary structure is dehybridized (or melted) and hybridization with the complementary template regions occurs under appropriate conditions. As used herein, a "standard PCR primer" length can be about 10 to about 100 bases.

A long PCR primer is able to resolve secondary structure in a target polynucleotide, but is not able to simultaneously provide either the specificity or sensitivity near the 3' (priming) end of the primer. This is because for a long PCR primer a large portion is hybridized to the target polynucleotide and a mismatch near the 3' end of the primer relative to the target polynucleotide will not be sufficient to reduce priming efficiency. As a result, a PCR product will still be synthesized despite the mismatch(es).

The polynucleotide combinations of the invention offer other advantages. For example, short PCR primers alone are useful for precise sequence hybridization to the target polynucleotide, but in order to achieve the high specificity of primer binding to a target polynucleotide that is desired for PCR, the highest possible annealing temperature is typically chosen. This annealing temperature is chosen based on the melting temperature of a given primer, and for a short primer that annealing temperature will be relatively low. A low annealing temperature, however, has the disadvantage of allowing for non-specific hybridization of the short primer to the target polynucleotide, resulting in non-specific PCR product formation. Based on the relatively low annealing temperature that must be used to allow a short PCR primer to anneal to its target polynucleotide, short primers form duplexes with a target polynucleotide that are typically unstable even when they are 100% complementary to the target polynucleotide region. Moreover, these duplexes are even more unstable when the primer is less than 100% complementary (i.e., at least one mismatch between the primer and the target polynucleotide region). The polynucleotide combination of the invention helps to overcome the instability problem associated with using a short PCR primer and permit highly specific binding to a desired target. For example, combinations of the disclosure are able to discriminate between target sequences that differ by as little as a single base.

For example, the discontinuous polynucleotide combination design (see FIG. 1) allows for use of a short PCR primer region [Pa] through hybridization of the first domain [Fa] of the fixer polynucleotide (i.e., "second polynucleotide") to the temple polynucleotide and hybridization of the second domain [Pc] of the primer polynucleotide (i.e., "first polynucleotide") to the second domain [Fd] of the fixer polynucleotide, thereby giving the effective result of an apparent "longer" primer sequence. This longer and discontinuous hybridization in effect stabilizes binding between the first region [Pa] of the primer polynucleotide even if this region is as small as eight bases, thereby increasing the efficiency of PCR.

In another embodiment, the regions of the template polynucleotide that are complementary to the first domain of the primer polynucleotide and fixer polynucleotide need not be directly adjacent. The present invention contemplates embodiments wherein the complementary regions are separated (i.e., discontinuous) by up to 10 nucleotides or more, and that upon fixer hybridization to the template polynucleotide, the intervening sequence is looped-out to bring the target template region to be amplified into proximity with the primer polynucleotide. In this aspect then, the primer combination actually induces secondary structure in the template polynucleotide, with or without internal self-hybridization of the looped out structure.

I. Polynucleotide Primer Combinations

In an embodiment, a polynucleotide combination is provided comprising a first polynucleotide and a second polynucleotide, the first polynucleotide comprising a first domain [Pa] that is complementary to a first target polynucleotide region and a second domain [Pc] comprising a unique polynucleotide sequence, and the second polynucleotide comprising a first domain [Fb] that is complementary to a second target polynucleotide region and a second domain [Fd] comprising a polynucleotide sequence sufficiently complementary to the second domain of the first polynucleotide such that the second domain of the first polynucleotide and the second domain of the second polynucleotide will hybridize under appropriate conditions. The structural relationship of the basic polynucleotide combination is shown in FIG. 1.

A. Three-Way Junction

In a three-way junction polynucleotide combination, the primer polynucleotide and the fixer polynucleotide are associated through interaction between the second domain of the first polynucleotide (Pc in Scheme 1) and the second domain of the second polynucleotide (Fd in Scheme 1), and the first domain of the primer oligonucleotide (Pa in FIG. 1) and the first domain of the fixer polynucleotide (Fb in FIG. 1) are hybridized to respective complementary regions in the target polynucleotide as shown in FIG. 2 (Scheme 2A).

B. More than Three-Way Junctions

The invention also contemplates an alternative embodiment wherein the primer combination comprises two three-way junctions (see FIG. 2; Scheme 2B). In some of these embodiments, domain "e" is complementary to domain [Pc], domain "f" is complementary to domain [Fd], and domain "g" is complementary to a third target polynucleotide region.

The present invention further contemplates a polynucleotide combination that comprises a four-way junction. In a four-way junction polynucleotide combination the primer polynucleotide and fixer polynucleotide are associated through a "staple" polynucleotide (Scheme 3A, below). The staple polynucleotide is able to hybridize with the second domains of both the primer polynucleotide and the fixer polynucleotide. The structure of the staple polynucleotide comprises a first domain [e] that is sufficiently complementary to the second domain [Pc] of the primer polynucleotide so that it the regions can hybridize under appropriate conditions, and a second domain [f] that is sufficiently complementary to the second domain [Fd] of the fixer polynucleotide can hybridize such that the regions can hybridize under appropriate conditions. In some aspects of this embodiment, the second domain Pc of the primer polynucleotide need not be sufficiently complementary to the second domain Fd in the fixer polynucleotide so as to allow for hybridization between the Pc domain and the Fd domain under typical conditions. In this aspect, with the first domain [e] in the staple being sufficiently complementary to the second domain Pc of the primer polynucleotide, and the second domain [f] of the staple being sufficiently complementary to the second domain [Fd] of the fixer domain, allows for formation of the stable four way junction shown in FIG. 3 (Scheme 3A).

Additional "staple" polynucleotides in the polynucleotide combinations are also contemplated as described herein, thereby generating multiple-way junctions depending on the number of staple polynucleotides in the polynucleotide combination. Scheme 3B shows a five way junction and the person of skill in the art will readily appreciate how junctions larger than five will be constructed.

Further, the "staple" polynucleotide may comprise a modified nucleotide as described herein. In additional aspects, the "staple" polynucleotide may comprise a label and/or a quencher. In these aspects, the label or quencher may be on either the 5' or 3' end of the "staple" polynucleotide.

C. Primer Combinations Comprising a Blocker Polynucleotide

The invention also contemplates embodiments wherein a blocker polynucleotide is included with a polynucleotide combinations. A blocker polynucleotide has a sequence that is complementary to a target polynucleotide region located immediately 5' of the first target polynucleotide region. This is depicted in FIG. 4. In some embodiments, the blocker polynucleotide overlaps with the first domain of the first polynucleotide. In other words, the nucleotide(s) at the 3' end of the first polynucleotide and the nucleotide(s) at the 5' end of the blocker polynucleotide would be complementary to the same nucleotide(s) of the target polynucleotide. In various embodiments, the overlap of the first polynucleotide and the blocker polynucleotide is 1 nucleotide, 2 nucleotides, 3 nucleotides, 4 nucleotides, 5 nucleotides, 6 nucleotides, 7 nucleotides, 8 nucleotides, 9 nucleotides, 10 nucleotides, 11 nucleotides, 12 nucleotides, 13 nucleotides, 14 nucleotides, or 15 nucleotides. In related embodiments, the nucleotide(s) at the 3' end of the first polynucleotide and the nucleotide(s) at the 5' end of the blocker polynucleotide are different. In these embodiments, the nucleotide(s) at the 3' end of the first polynucleotide would hybridize to the target polynucleotide when they are complementary to the target polynucleotides at the appropriate position, thus allowing for extension of the first polynucleotide under the appropriate conditions (see FIG. 4a). In related embodiments, the nucleotide(s) at the 5' end of the blocker polynucleotide would hybridize to the target polynucleotide when they are complementary to the non-target polynucleotide at the appropriate position, thus blocking extension of the first polynucleotide (see FIG. 4b). In various embodiments, the nucleotide at the 3' end of the blocker polynucleotide is modified to prevent extension by a polymerase.

In some embodiments, the overlapping sequences of the blocker polynucleotide and the first domain of the first polynucleotide (Pa) differ by at least 2 bases, at least 3 bases, at least 4 bases, at least 5 bases, at least 6 bases, at least 7 bases, at least 8 bases, at 9 two bases, or by at least 10 bases. The differing bases can be at any position in the overlapping portions.

D. Primer Combinations Comprising a Probe Polynucleotide

The invention also contemplates embodiments wherein a probe polynucleotide is included with the above polynucleotide combinations. A probe polynucleotide has a sequence that is complementary to a target polynucleotide region located 5' of the first target polynucleotide region (see FIG. 5a). In other embodiments, a probe polynucleotide has a sequence that is complementary to the extension product of the first polynucleotide (see FIG. 5b). As is apparent, this probe polynucleotide would be complementary to the complementary strand of the target polynucleotide. In embodiments wherein a blocker polynucleotide is included in the primer combination with the probe polynucleotide, the probe polynucleotide is complementary to a target polynucleotide region located 5' of the target polynucleotide region complementary to the blocker polynucleotide. In various embodiments, the probe polynucleotide comprises a label at its 5' end. In related embodiments, the probe polynucleotide further comprises a quencher at its 3' end. In still further embodiments, the probe polynucleotide further comprises an internal quencher, such as, and without limitation, the Zen quencher.

E. Primer Combinations Comprising a Universal Quencher

Figure 6:
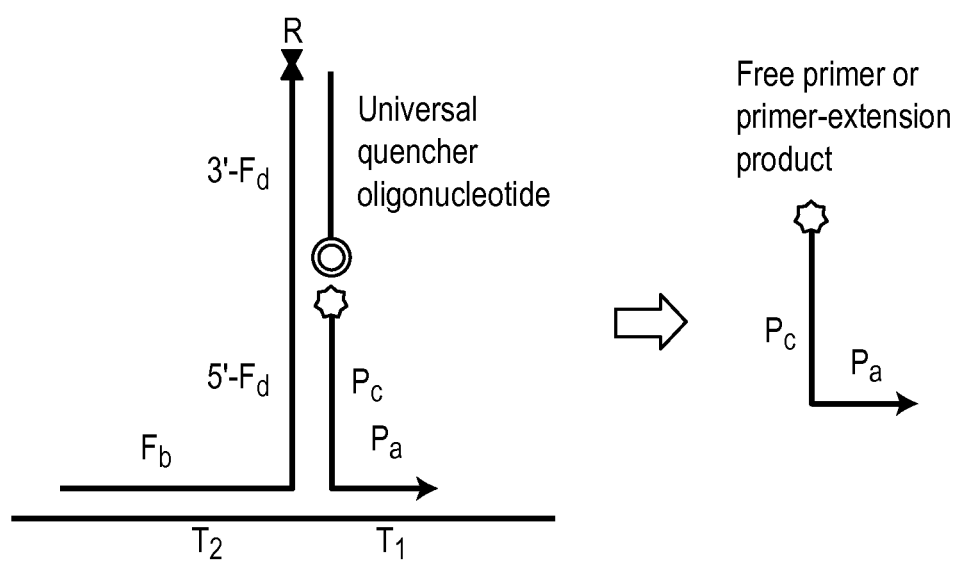
FIG. 6 depicts the structural relationship of the basic polynucleotide combination with a universal quencher polynucleotide. As depicted, the universal quencher polynucleotide is complementary to the second domain of the second polynucleotide and comprises a quencher at its 3' end while the first polynucleotide comprises a label at its 5' end.

In various embodiments, the primer polynucleotide combination includes a universal quencher polynucleotide. The universal quencher polynucleotide is complementary to the second domain of the second polynucleotide such that it hybridizes to the second domain of the second polynucleotide. In these embodiments, the universal quencher polynucleotide hybridizes to a region of the second polynucleotide located 3' of the region to which the second domain of the second polynucleotide hybridizes (see FIG. 6). The universal quencher polynucleotide is labeled at its 3' end with a quencher.

F. Primer Combinations Comprising a Reverse Primer

Figure 8A:
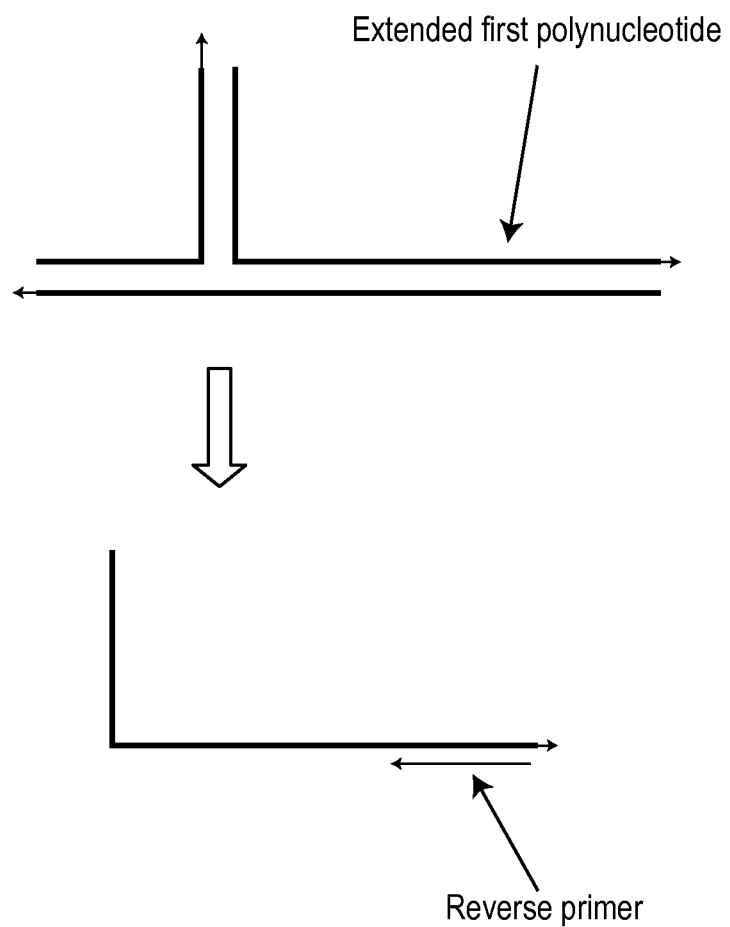
FIGS. 8A and 8B depict the structural relationship of the basic polynucleotide combination and a reverse primer.
Figure 8B:
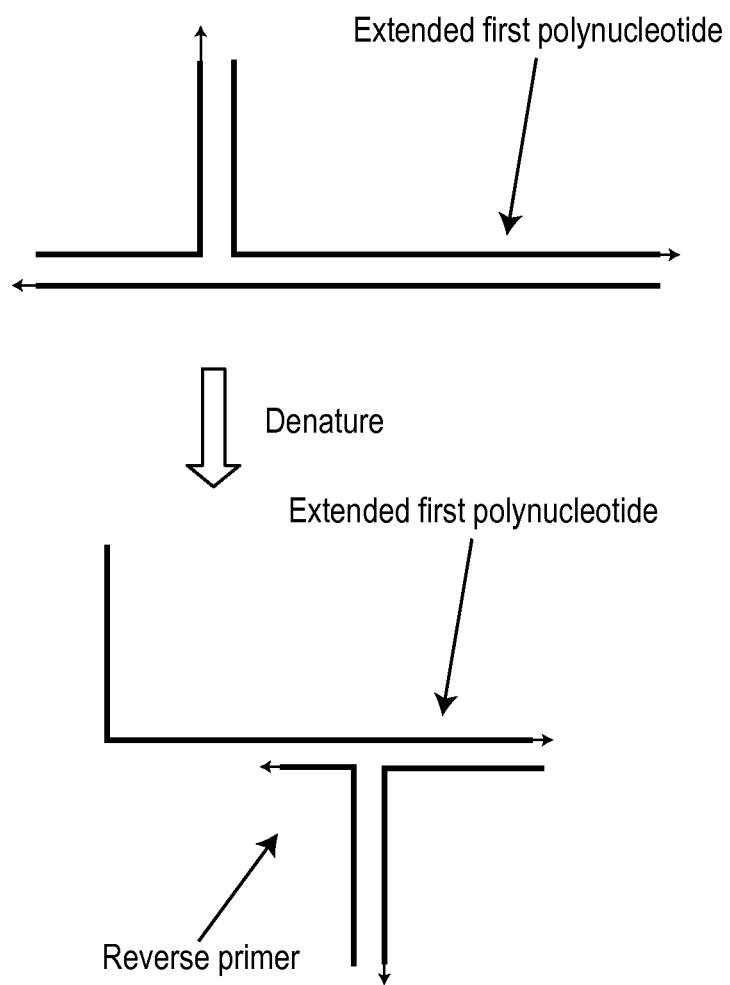

The invention also contemplates embodiments wherein a reverse primer polynucleotide is included with the above polynucleotide combinations. The reverse primer is complementary to a region in the polynucleotide created by extension of the first polynucleotide (see FIG. 8a). As is apparent, in some embodiments the reverse primer is also complementary to the complementary strand of the target polynucleotide when the target polynucleotide is one strand of a double-stranded polynucleotide. In some embodiments, the reverse primer is a combination first polynucleotide/second polynucleotide, as described above (see FIG. 8b).

II. Polynucleotides

As used herein, the term "polynucleotide," either as a component of a polynucleotide pair combination, including blocker polynucleotides and probes, or as a target molecule, is used interchangeably with the term oligonucleotide.

The term "nucleotide" or its plural as used herein is interchangeable with modified forms as discussed herein and otherwise known in the art. In certain instances, the art uses the term "nucleobase" which embraces naturally-occurring nucleotides as well as modifications of nucleotides that can be polymerized.

Methods of making polynucleotides of a predetermined sequence are well-known in the art. See, e.g., Sambrook et al., Molecular Cloning: A Laboratory Manual (2nd ed. 1989) and F. Eckstein (ed.) Oligonucleotides and Analogues, 1st Ed. (Oxford University Press, New York, 1991). Solid-phase synthesis methods are preferred for both oligoribonucleotides and oligodeoxyribonucleotides (the well-known methods of synthesizing DNA are also useful for synthesizing RNA). Oligoribonucleotides and oligodeoxyribonucleotides can also be prepared enzymatically.

In various aspects, methods provided include use of polynucleotides which are DNA oligonucleotides, RNA oligonucleotides, or combinations of the two types. Modified forms of oligonucleotides are also contemplated which include those having at least one modified internucleotide linkage. Modified polynucleotides or oligonucleotides are described in detail herein below.

III. Modified Polynucleotide

Specific examples of oligonucleotides include those containing modified backbones or non-natural internucleoside linkages. Oligonucleotides having modified backbones include those that retain a phosphorus atom in the backbone and those that do not have a phosphorus atom in the backbone. Modified oligonucleotides that do not have a phosphorus atom in their internucleoside backbone are considered to be within the meaning of "oligonucleotide." In specific embodiments, the first polynucleotide comprises phosphorothioate linkages.

Modified oligonucleotide backbones containing a phosphorus atom include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Also contemplated are oligonucleotides having inverted polarity comprising a single 3' to 3' linkage at the 3'-most internucleotide linkage, i.e. a single inverted nucleoside residue which may be abasic (the nucleotide is missing or has a hydroxyl group in place thereof). Salts, mixed salts and free acid forms are also contemplated. Representative United States patents that teach the preparation of the above phosphorus-containing linkages include, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, the disclosures of which are incorporated by reference herein.

Modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages; siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. See, for example, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, the disclosures of which are incorporated herein by reference in their entireties.

In still other embodiments, oligonucleotide mimetics wherein both one or more sugar and/or one or more internucleotide linkage of the nucleotide units are replaced with "non-naturally occurring" groups. In one aspect, this embodiment contemplates a peptide nucleic acid (PNA). In PNA compounds, the sugar-backbone of an oligonucleotide is replaced with an amide containing backbone. See, for example U.S. Pat. Nos. 5,539,082; 5,714,331; and 5,719, 262, and Nielsen et al., 1991, *Science*, 254: 1497-1500, the disclosures of which are herein incorporated by reference.

In still other embodiments, oligonucleotides are provided with phosphorothioate backbones and oligonucleosides with heteroatom backbones, and including —$CH_2$—NH—O—$CH_2$—, —$CH_2$—N($CH_3$)—O—$CH_2$—, —$CH_2$—O—N($CH_3$)—$CH_2$—, —$CH_2$—N($CH_3$)—N($CH_3$)—$CH_2$— and —O—N($CH_3$)—$CH_2$—$CH_2$— described in U.S. Pat. Nos. 5,489,677, and 5,602,240. Also contemplated are oligonucleotides with morpholino backbone structures described in U.S. Pat. No. 5,034,506.

In various forms, the linkage between two successive monomers in the oligo consists of 2 to 4, desirably 3, groups/atoms selected from —$CH_2$—, —O—, —S—, —$NR^H$—, >C=O, >C=$NR^H$, >C=S, —Si(R")$_2$—, —SO—, —S(O)$_2$—, —P(O)$_2$—, —PO(BH$_3$)—, —P(O,S)—, —P(S)$_2$—, —POR(")—, —PO(OCH$_3$)—, and —PO(NHR$^H$)—, where RH is selected from hydrogen and $C_{1-4}$-alkyl, and R" is selected from $C_{1-6}$-alkyl and phenyl. Illustrative examples of such linkages are —$CH_2$—$CH_2$—$CH_2$—, —$CH_2$—CO—$CH_2$—, —$CH_2$—CHOH—$CH_2$—, —O—$CH_2$—O—, —O—$CH_2$—$CH_2$—, —O—$CH_2$—CH= (including $R^5$ when used as a linkage to a succeeding monomer), —$CH_2$—$CH_2$—O—, —$NR^H$$CH_2$—$CH_2$—, —$CH_2$—$CH_2$—$NR^H$, —$CH_2$—$NR^H$—$CH_2$—, —O—$CH_2$—$CH_2$—$NR^H$—, —$NR^H$—CO—O—, —$NR^H$—CO—$NR^H$—, —$NR^H$—CS—$NR^H$—, —$NR^H$—C(=$NR^H$)—$NR^H$—, —$NR^H$—CO—$CH_2$—$NR^H$—O—CO—O—, —O—CO—$CH_2$—O—, —O—$CH_2$—CO—O—, —$CH_2$—CO—$NR^H$—, —O—CO—$NR^H$—, —$NR^H$—CO—$CH_2$—, —O—$CH_2$—CO—$NR^H$—, —O—$CH_2$—$CH_2$—$NR^H$—, —CH=N—O—, —$CH_2$—$NR^H$—O—, —$CH_2$—O—N= (including $R^5$ when used as a linkage to a succeeding monomer), —$CH_2$—O—$NR^H$—, —CO—$NR^H$—$CH_2$—, —$CH_2$—$NR^H$—O—, $CH_2$—$NR^H$—CO—, —O—$NR^H$—$CH_2$—, —O—$NR^H$, —O—$CH_2$—S—, —S—$CH_2$—O—, —$CH_2$—$CH_2$—S—, —O—$CH_2$—$CH_2$—S—, —S—$CH_2$—CH= (including $R^5$ when used as a linkage to a succeeding monomer), —S—$CH_2$—$CH_2$—, —S—$CH_2$—$CH_2$—O—, —S—$CH_2$—$CH_2$—S—, —$CH_2$—S—$CH_2$—, —$CH_2$—SO—$CH_2$—, —$CH_2$—SO$_2$—$CH_2$—, —O—SO—O—, —O—S(O)$_2$—O—, —O—S(O)$_2$—$CH_2$—, —O—S(O)$_2$—$NR^H$—, —$NR^H$—S(O)$_2$—$CH_2$—; —O—S(O)$_2$—$CH_2$—, —O—P(O)$_2$—O—, —O—P(O,S)—O—, —O—P(S)$_2$—O—, —S—P(O)$_2$—O—, —S—P(O,S)—O—, —S—P(S)$_2$—O—, —O—P(O)$_2$—S—, —O—P(O,S)—S—, —O—P(S)$_2$—S—, —S—P(O)$_2$—S—, —S—P(O,S)—S—, —S—P(S)$_2$—S—, —O—PO(R")—O—, —O—PO(OCH$_3$)—O—, —O—PO(OCH$_2$CH$_3$)—O—, —O—PO(OCH$_2$CH$_2$S—R)—O—, —O—PO(BH$_3$)—O—, —O—PO(NHR$^N$)—O—, —O—P(O)$_2$—$NR^H$H—, —$NR^H$—P(O)$_2$—O—, —O—P(O,$NR^H$)—O—, —$CH_2$—P(O)$_2$—O—, —O—P(O)$_2$—$CH_2$—, and —O—Si(R")$_2$—O—; among which —$CH_2$—CO—$NR^H$—, —$CH_2$—$NR^H$—O—, —S—$CH_2$—O—, —O—P(O)$_2$—O—O—P(—,O,S)—O—, —O—P(S)$_2$—O—, —$NR^H$ P(O)$_2$—O—, —O—P(O,$NR^H$)—O—, —O—PO(R")—O—, —O—PO(CH$_3$)—O—, and —O—PO(NHR$^N$)—O—, where RH is selected form hydrogen and $C_{1-4}$-alkyl, and R" is selected from $C_{1-6}$-alkyl and phenyl, are contemplated. Further illustrative examples are given in Mesmaeker et. al., 1995, *Current Opinion in Structural Biology*, 5: 343-355 and Susan M. Freier and Karl-Heinz Altmann, 1997, *Nucleic Acids Research*, vol 25: pp 4429-4443.

Still other modified forms of oligonucleotides are described in detail in U.S. patent application NO. 20040219565, the disclosure of which is incorporated by reference herein in its entirety.

Modified oligonucleotides may also contain one or more substituted sugar moieties. In certain aspects, oligonucleotides comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Other embodiments include O[($CH_2$)$_n$O]$_m$CH$_3$, O($CH_2$)$_n$OCH$_3$, O($CH_2$)$_n$OH$_2$, O($CH_2$)$_n$CH$_3$, O($CH_2$)$_n$ONH$_2$, and O($CH_2$)$_n$ON[($CH_2$)$_n$CH$_3$]$_2$, where n and m are from 1 to about 10. Other oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH2, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. In one aspect, a modification includes 2'-methoxyethoxy (2'-O—CH$_2$CH$_2$OCH$_3$, also known as 2'-O-(2-methoxyethyl) or 2'-MOE) (Martin et al., 1995, *Helv. Chim. Acta*, 78: 486-504) i.e., an alkoxyalkoxy group. Other modifications include 2'-dimethylaminooxyethoxy, i.e., a O(CH$_2$)$_2$ON(CH$_3$)$_2$ group, also known as 2'-DMAOE, as described in examples herein below, and 2'-dimethylaminoethoxyethoxy (also known in the art as 2'-O-dimethyl-amino-ethoxy-ethyl or 2'-DMAEOE), i.e., 2'-O—CH$_2$—O—CH$_2$—N(CH$_3$)$_2$, also described in examples herein below.

Still other modifications include 2'-methoxy (2'-O—CH$_3$), 2'-aminopropoxy (2'-OCH$_2$CH$_2$CH$_2$NH$_2$), 2'-allyl (2'-CH$_2$—CH=CH$_2$), 2'-O-allyl (2'-O—CH$_2$—CH=CH$_2$) and 2'-fluoro (2'-F). The 2'-modification may be in the arabino (up) position or ribo (down) position. In one aspect, a 2'-arabino modification is 2'-F. Similar modifications may also be made at other positions on the oligonucleotide, for example, at the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. See, for example, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, the disclosures of which are incorporated by reference in their entireties herein.

In various aspects, a modification of the sugar includes Locked Nucleic Acids (LNAs) in which the 2'-hydroxyl group is linked to the 3' or 4' carbon atom of the sugar ring, thereby forming a bicyclic sugar moiety. The linkage in certain aspects is a methylene ($-CH_2-$)$_n$ group bridging the 2' oxygen atom and the 4' carbon atom wherein n is 1 or 2. LNAs and preparation thereof are described in WO 98/39352 and WO 99/14226, the disclosures of which are incorporated by reference in their entireties herein. In various embodiments, the first polynucleotide comprises a locked nucleic acid. In some embodiments, the first polynucleotide comprises a plurality of locked nucleic acids. In specific embodiments, the first domain of the first polynucleotide comprises a plurality of locked nucleic acids. In more specific embodiments, the nucleotide at the 3' end of the first polynucleotide comprises a locked nucleic acid. In various embodiments, the blocker polynucleotide comprises a locked nucleic acid. In other embodiments, the blocker polynucleotide comprises a plurality of locked nucleic acids. In specific embodiments, the nucleotide at the 5' end of the blocker polynucleotide comprises a locked nucleic acid.

Polynucleotides may also include base modifications or substitutions. As used herein, "unmodified" or "natural" bases include the purine bases adenine (A) and guanine (G), and the pyrimidine bases thymine (T), cytosine (C) and uracil (U). Modified bases include other synthetic and natural bases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified bases include tricyclic pyrimidines such as phenoxazine cytidine (1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzox-azin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified bases may also include those in which the purine or pyrimidine base is replaced with other heterocycles, for example 7-deaza-adenine, 7-deazaguanosine, 2-aminopyridine and 2-pyridone. Further bases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., 1991, *Angewandte Chemie*, International Edition, 30: 613, and those disclosed by Sanghvi, Y. S., Chapter 15, Antisense Research and Applications, pages 289-302, Crooke, S. T. and Lebleu, B., ed., CRC Press, 1993. Certain of these bases are useful for increasing the binding affinity and include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are, in certain aspects combined with 2'-O-methoxyethyl sugar modifications. See, U.S. Pat. Nos. 3,687,808, 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; 5,750,692 and 5,681,941, the disclosures of which are incorporated herein by reference.

A "modified base" or other similar term refers to a composition which can pair with a natural base (e.g., adenine, guanine, cytosine, uracil, and/or thymine) and/or can pair with a non-naturally occurring base. In certain aspects, the modified base provides a $T_m$ differential of 15, 12, 10, 8, 6, 4, or 2° C. or less. Exemplary modified bases are described in EP 1 072 679 and WO 97/12896.

By "nucleobase" is meant the naturally occurring nucleobases adenine (A), guanine (G), cytosine (C), thymine (T) and uracil (U) as well as non-naturally occurring nucleobases such as xanthine, diaminopurine, 8-oxo-$N^6$-methyladenine, 7-deazaxanthine, 7-deazaguanine, $N^4,N^4$-ethanocytosin, N',N'-ethano-2,6-diaminopurine, 5-methylcytosine (mC), 5-($C^3$-$C^6$)-alkynyl-cytosine, 5-fluorouracil, 5-bromouracil, pseudoisocytosine, 2-hydroxy-5-methyl-4-triazolopyridin, isocytosine, isoguanine, inosine and the "non-naturally occurring" nucleobases described in Benner et al., U.S. Pat. No. 5,432,272 and Susan M. Freier and Karl-Heinz Altmann, 1997, *Nucleic Acids Research*, vol. 25: pp 4429-4443. The term "nucleobase" thus includes not only the known purine and pyrimidine heterocycles, but also heterocyclic analogues and tautomers thereof. Further naturally and non-naturally occurring nucleobases include those disclosed in U.S. Pat. No. 3,687,808 (Merigan, et al.), in Chapter 15 by Sanghvi, in Antisense Research and Application, Ed. S. T. Crooke and B. Lebleu, CRC Press, 1993, in Englisch et al., 1991, *Angewandte Chemie*, International Edition, 30: 613-722 (see especially pages 622 and 623, and in the Concise Encyclopedia of Polymer Science and Engineering, J. I. Kroschwitz Ed., John Wiley & Sons, 1990, pages 858-859, Cook, Anti-Cancer Drug Design 1991, 6, 585-607, each of which are hereby incorporated by reference in their entirety). The term "nucleosidic base" or "base unit" is further intended to include compounds such as heterocyclic compounds that can serve like nucleobases including certain "universal bases" that are not nucleosidic bases in the most classical sense but serve as nucleosidic bases. Especially mentioned as universal bases are 3-nitropyrrole, optionally substituted indoles (e.g., 5-nitroindole), and optionally substituted hypoxanthine. Other desirable universal bases include, pyrrole, diazole or triazole derivatives, including those universal bases known in the art.

IV. Polynucleotide Structure—Length

In one aspect, the first domain of the first polynucleotide is 5 nucleotides that is complementary to a target polynucleotide region. In various aspects, the first domain of the first polynucleotide is at least 6 nucleotides, at least 7 nucleotides, at least 8 nucleotides, at least 9 nucleotides, at least 10 nucleotides, at least 11 nucleotides, at least 12 nucleotides, at least 13 nucleotides, at least 14 nucleotides, at least 15 nucleotides, at least 16 nucleotides, at least 17 nucleotides, at least 18 nucleotides, at least 19 nucleotides, at least 20 nucleotides, at least 21 nucleotides, at least 22 nucleotides, at least 23 nucleotides, at least 24 nucleotides, at least 25 nucleotides, at least 26 nucleotides, at least 27 nucleotides, at least 28 nucleotides, at least 29 nucleotides, at least 30 nucleotides or more that is complementary to a target polynucleotide region. In a related aspect, the second domain of the first polynucleotide comprises 10 or more nucleotides in a unique DNA sequence that is sufficiently complementary to the second domain of the second polynucleotide so as to allow hybridization between these two complementary sequences under appropriate conditions. In various aspects, the second domain of the first polynucleotide comprises at least 11, at least 12, at least 13, at least 14, at least 15, at least 16, at least 17, at least 18, at least 19, at least 20, at least 21, at least 22, at least 23, at least 24 nucleotides, at least 25, at least about 30, at least about 35, at least about 40, at least about 45, at least about 50, at least about 60, at least about 70, at least about 80, at least about 90, at least about 100, at least about 120, at least about 140, at least about 160, at least about 180, at least about 200, at least about 220, at least about 240, at least about 260, at least about 280, at least about 300, at least about 320, at least about 340, at least about 360, at least about 380, at least about 400, at least about 420, at least about 440, at least about 460, at least about 480, at least about 500 or more nucleotides of a unique DNA sequence that is sufficiently complementary to the second domain of the second polynucleotide so as to allow hybridization between the two complementary sequences under appropriate conditions.

In another embodiment, the second polynucleotide comprises a first domain containing about 10 nucleotides, this first domain of the second polynucleotide being complementary to a target DNA region that is different from the target region recognized by the first domain of the first polynucleotide. In various aspects, the second polynucleotide comprises a first domain containing at least 11, at least 12, at least 13, at least 14, at least 15, at least 16, at least 17, at least 18, 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least about 100, at least about 150, at least about 200, at least about 250, at least about 300, at least about 350, at least about 400, at least about 450, at least about 500, at least about 550, at least about 600, at least about 650, at least about 700, at least about 750, at least about 800, at least about 850, at least about 900, at least about 950, at least about 1000, at least about 1100, at least about 1200, at least about 1300, at least about 1400, at least about 1500, at least about 1600, at least about 1700, at least about 1800, at least about 1900, at least about 2000, at least about 2100, at least about 2200, at least about 2300, at least about 2400, at least about 2500, at least about 2600, at least about 2700, at least about 2800, at least about 2900, at least about 3000, at least about 3100, at least about 3200, at least about 3300, at least about 3400, at least about 3500, at least about 3600, at least about 3700, at least about 3800, at least about 3900, at least about 4000, at least about 4100, at least about 4200, at least about 4300, at least about 4400, at least about 4500, at least about 4600, at least about 4700, at least about 4800, at least about 4900, at least about 5000 or more nucleotides, the first domain of this second polynucleotide being complementary, or sufficiently complementary, so as to recognize and bind to a target DNA region that is different from the target region recognized by the first domain of the first polynucleotide.

In a related aspect, the second domain of the second polynucleotide comprises 10 nucleotides of a unique DNA sequence that is sufficiently complementary to the second domain of the first polynucleotide so as to allow hybridization under appropriate conditions. In various aspects, the second domain of the second polynucleotide comprises at least 11, at least 12, at least 13, at least 14, at least 15, at least 16, at least 17, at least 18, at least 19, at least 20, at least 21, at least 22, at least 23, at least 24, at least 25, at least about 30, at least about 35, at least 40, at least about 45, at least about 50, at least about 60, at least about 70, at least about 80, at least about 90, at least about 100, at least about 120, at least about 140, at least about 160, at least about 180, at least about 200, at least about 220, at least about 240, at least about 260, at least about 280, at least about 300, at least about 320, at least about 340, at least about 360, at least about 380, at least about 400, or least about 420, or least about 440, at least about 460, at least about 480, at least about 500 or more nucleotides of a unique DNA sequence that is sufficiently complementary to the second domain of the first polynucleotide so as to allow hybridization between the two sufficiently complementary sequences under appropriate conditions.

In some embodiments, compositions and methods described herein include a second set of polynucleotides with the characteristics described above for first and second polynucleotides. In some embodiments, a plurality of sets is contemplated. These additional sets of first and second polynucleotides can have any of the characteristics described for first and second polynucleotides.

The "staple" polynucleotides, as depicted in FIG. 3 (Scheme 3A and 3B), are contemplated in one aspect to comprise at least 20 nucleotides. In other aspects, the "staple" polynucleotides can comprise at least 21 nucleotides, or at least 22 nucleotides, or at least 23 nucleotides, or at least 24 nucleotides, or at least 25 nucleotides, or at least 26 nucleotides, or at least 27 nucleotides, or at least 28 nucleotides, or at least 29 nucleotides, or at least 30 nucleotides, or at least about 35 nucleotides, or at least about 40 nucleotides, or at least about 45 nucleotides, or at least about 50 nucleotides, or at least about 55 nucleotides, or at least about 60 nucleotides, or at least about 65 nucleotides, or at least about 70 nucleotides, or at least about 75 nucleotides, or at least about 80 nucleotides, or at least about 85 nucleotides, or at least about 90 nucleotides, or at least about 95 nucleotides, or at least about 100 nucleotides, or at least about 150 nucleotides, or at least about 200 nucleotides, or at least about 250 nucleotides, or at least about 300 nucleotides, or at least about 350 nucleotides, or at least about 400 nucleotides, or at least about 450 nucleotides, or at least 500 nucleotides or more.

In some embodiments, the universal quencher polynucleotide is from about 5 nucleotides in length to about 100 bases in length. In various aspects, the universal quencher polynucleotide comprises at least 5 nucleotides, or at least 6 nucleotides, or at least 7 nucleotides, or at least 8 nucleotides, or at least 9 nucleotides, or at least 10 nucleotides, or at least 11 nucleotides, or at least 12 nucleotides, or at least 13 nucleotides, or at least 14 nucleotides, or at least 15 nucleotides, or at least 16 nucleotides, or at least 17 nucleotides, or at least 18 nucleotides, or at least 19 nucleotides, or at least 20 nucleotides, or at least 21 nucleotides, or at least 22 nucleotides, or at least 23 nucleotides, or at least 24 nucleotides, or at least 25 nucleotides, or at least 26 nucleotides, or at least 27 nucleotides, or at least 28 nucleotides, or at least 29 nucleotides, or at least 30 nucleotides, or at least about 35 nucleotides, or at least about 40 nucleotides, or at least about 45 nucleotides, or at least about 50 nucleotides, or at least about 55 nucleotides, or at least about 60 nucleotides, or at least about 65 nucleotides, or at least about 70 nucleotides, or at least about 75 nucleotides, or at least about 80 nucleotides, or at least about 85 nucleotides, or at least about 90 nucleotides, or at least about 95 nucleotides, or at least about 100 nucleotides of a unique DNA sequence that is sufficiently complementary to the second domain of the second polynucleotide so as to allow hybridization under appropriate conditions.

In some embodiments, the probe polynucleotide is from about 5 nucleotides in length to about 100 bases in length. In various aspects, the probe polynucleotide comprises at least 5 nucleotides, or at least 6 nucleotides, or at least 7 nucleotides, or at least 8 nucleotides, or at least 9 nucleotides, or at least 10 nucleotides, or at least 11 nucleotides, or at least 12 nucleotides, or at least 13 nucleotides, or at least 14 nucleotides, or at least 15 nucleotides, or at least 16 nucleotides, or at least 17 nucleotides, or at least 18 nucleotides, or at least 19 nucleotides, or at least 20 nucleotides, or at least 21 nucleotides, or at least 22 nucleotides, or at least 23 nucleotides, or at least 24 nucleotides, or at least 25 nucleotides, or at least 26 nucleotides, or at least 27 nucleotides, or at least 28 nucleotides, or at least 29 nucleotides, or at least 30 nucleotides, or at least 31 nucleotides, or at least 32 nucleotides, or at least 33 nucleotides, or at least 34 nucleotides, or at least 35 nucleotides, or at least 36 nucleotides, or at least 37 nucleotides, or at least 38 nucleotides, or at least 39 nucleotides, or at least 40 nucleotides, or at least about 45 nucleotides, or at least about 50 nucleotides, or at least about 55 nucleotides, or at least about 60 nucleotides, or at least about 65 nucleotides, or at least about 70 nucleotides, or at least about 75 nucleotides, or at least about 80 nucleotides, or at least about 85 nucleotides, or at least about 90 nucleotides, or at least about 95 nucleotides, or at least about 100 nucleotides of a DNA sequence that is sufficiently complementary to a target polynucleotide region so as to allow hybridization under appropriate conditions.

In some embodiments, the blocker polynucleotide is from about 5 nucleotides in length to about 100 bases in length. In various aspects, the blocker polynucleotide comprises at least 5 nucleotides, or at least 6 nucleotides, or at least 7 nucleotides, or at least 8 nucleotides, or at least 9 nucleotides, or at least 10 nucleotides, or at least 11 nucleotides, or at least 12 nucleotides, or at least 13 nucleotides, or at least 14 nucleotides, or at least 15 nucleotides, or at least 16 nucleotides, or at least 17 nucleotides, or at least 18 nucleotides, or at least 19 nucleotides, or at least 20 nucleotides, or at least 21 nucleotides, or at least 22 nucleotides, or at least 23 nucleotides, or at least 24 nucleotides, or at least 25 nucleotides, or at least 26 nucleotides, or at least 27 nucleotides, or at least 28 nucleotides, or at least 29 nucleotides, or at least 30 nucleotides, or at least 31 nucleotides, or at least 32 nucleotides, or at least 33 nucleotides, or at least 34 nucleotides, or at least 35 nucleotides, or at least 36 nucleotides, or at least 37 nucleotides, or at least 38 nucleotides, or at least 39 nucleotides, or at least 40 nucleotides, or at least about 45 nucleotides, or at least about 50 nucleotides, or at least about 55 nucleotides, or at least about 60 nucleotides, or at least about 65 nucleotides, or at least about 70 nucleotides, or at least about 75 nucleotides, or at least about 80 nucleotides, or at least about 85 nucleotides, or at least about 90 nucleotides, or at least about 95 nucleotides, or at least about 100 nucleotides of a polynucleotide sequence that is sufficiently complementary to a target polynucleotide region so as to allow hybridization under appropriate conditions. In various embodiments, the blocker polynucleotide further comprises a modified nucleic acid as the nucleotide at its 5' end. In various embodiments, the modified nucleic acid is a locked nucleic acid. In some embodiments, the blocker polynucleotide further comprises a blocking group at the 3' end to prevent extension by a polymerase.

In some embodiments, the reverse primer polynucleotide is from about 5 nucleotides in length to about 100 bases in length. In various aspects, the reverse primer polynucleotide comprises at least 5 nucleotides, or at least 6 nucleotides, or at least 7 nucleotides, or at least 8 nucleotides, or at least 9 nucleotides, or at least 10 nucleotides, or at least 11 nucleotides, or at least 12 nucleotides, or at least 13 nucleotides, or at least 14 nucleotides, or at least 15 nucleotides, or at least 16 nucleotides, or at least 17 nucleotides, or at least 18 nucleotides, or at least 19 nucleotides, or at least 20 nucleotides, or at least 21 nucleotides, or at least 22 nucleotides, or at least 23 nucleotides, or at least 24 nucleotides, or at least 25 nucleotides, or at least 26 nucleotides, or at least 27 nucleotides, or at least 28 nucleotides, or at least 29 nucleotides, or at least 30 nucleotides, or at least 31 nucleotides, or at least 32 nucleotides, or at least 33 nucleotides, or at least 34 nucleotides, or at least 35 nucleotides, or at least 36 nucleotides, or at least 37 nucleotides, or at least 38 nucleotides, or at least 39 nucleotides, or at least 40 nucleotides, or at least about 45 nucleotides, or at least about 50 nucleotides, or at least about 55 nucleotides, or at least about 60 nucleotides, or at least about 65 nucleotides, or at least about 70 nucleotides, or at least about 75 nucleotides, or at least about 80 nucleotides, or at least about 85 nucleotides, or at least about 90 nucleotides, or at least about 95 nucleotides, or at least about 100 nucleotides of a polynucleotide sequence that is sufficiently complementary to a region of a polymerase-extended first polynucleotide so as to allow hybridization under appropriate conditions. In some embodiments, when the target polynucleotide is a double-stranded polynucleotide, the reverse primer is complementary to a complementary strand of the target polynucleotide. In some embodiments, the reverse primer is a combination of first and second polynucleotides, as defined herein.

V. Polynucleotide Base Structure

In some embodiments, the first polynucleotide is comprised of DNA, modified DNA, RNA, modified RNA, PNA, or combinations thereof. In other embodiments, the second polynucleotide is comprised of DNA, modified DNA, RNA, modified RNA, PNA, or combinations thereof.

VI. Polynucleotide Structure—Blocking Groups

Blocking groups are incorporated as needed when polymerase extension from a 3' region of a polynucleotide is undesirable. For example, the second domain of the second polynucleotide, in another aspect, further comprises a blocking group ("R" in FIG. 1) at the 3' end of the second domain to prevent extension by an enzyme that is capable of synthesizing a nucleic acid. In additional aspects, the universal quencher comprises a blocking group at its 3' end. In further aspects, the blocker polynucleotide comprises a blocking group at its 3' end. Blocking groups useful in the practice of the methods include but are not limited to a 3' phosphate group, a 3' amino group, a dideoxy nucleotide, a six carbon glycol spacer (and in one aspect the six carbon glycol spacer is hexanediol) and inverted deoxythymidine (dT).

VII. Polynucleotide Structure—Complementarity

In some aspects, the second domain of the second polynucleotide is at least about 70% complementary to the second domain of the first polynucleotide. In related aspects, the second domain of the second polynucleotide is at least about 75%, at least about 80%, at least about 85%, at least about 90%, at least about 95%, or about 100% complementary to the second domain of the first polynucleotide.

In one aspect, the second domain of the third polynucleotide is at least about 70% complementary to the second domain of the fourth polynucleotide. In related aspects, the second domain of the third polynucleotide is at least about 75%, or at least about 80%, or at least about 85%, or at least about 90%, or at least about 95%, or about 100% complementary to the second domain of the fourth polynucleotide.

In another aspect, the blocker polynucleotide is at least about 75%, at least about 80%, at least about 85%, at least about 90%, at least about 95%, or about 100% complementary to a sequence in the target polynucleotide, and in yet another aspect, the probe polynucleotide is at least about 75%, at least about 80%, at least about 85%, at least about 90%, at least about 95%, or about 100% complementary to a sequence in the target polynucleotide, VIII. Hybridization Conditions In some embodiments, the first and second polynucleotide hybridize to each other under stringent conditions in the absence of a template polynucleotide. In some embodiments, the first and second polynucleotides do not hybridize to each other under stringent conditions in the absence of a template polynucleotide. "Stringent conditions" as used herein can be determined empirically by the worker of ordinary skill in the art and will vary based on, e.g., the length of the primer, complementarity of the primer, concentration of the primer, the salt concentration (i.e., ionic strength) in the hybridization buffer, the temperature at which the hybridization is carried out, length of time that hybridization is carried out, and presence of factors that affect surface charge of the polynucleotides. In general, stringent conditions are those in which the polynucleotide is able to bind to its complementary sequence preferentially and with higher affinity relative to any other region on the target. Exemplary stringent conditions for hybridization to its complement of a polynucleotide sequence having 20 bases include without limitation about 50% G+C content, 50 mM salt (Na$^+$), and an annealing temperature of 60° C. For a longer sequence, specific hybridization is achieved at higher temperature. In general, stringent conditions are such that annealing is carried out about 5° C. below the melting temperature of the polynucleotide. The "melting temperature" is the temperature at which 50% of polynucleotides that are complementary to a target polynucleotide in equilibrium at definite ion strength, pH and polynucleotide concentration.

IX. Methods of Use

A. PCR

In target polynucleotide amplification methods described herein, a third polynucleotide and a fourth polynucleotide are contemplated for use in combination with the polynucleotide combination described above, the third polynucleotide comprising a first domain [Pa] that is complementary to a complementary strand of the target polynucleotide [relative to the strand to which the first domain of the first polynucleotide is complementary] at a first target complement polynucleotide region and a second domain [Pc] comprising a unique polynucleotide sequence, and the fourth polynucleotide comprising a first domain [Fb] that is complementary to the complementary strand of the target polynucleotide [relative to the strand to which the second polynucleotide is complementary] at a second complement target polynucleotide region and a second domain [Fd] comprising a polynucleotide sequence sufficiently complementary to the second domain of the third polynucleotide such that the second domain of the third polynucleotide and the second domain of the fourth polynucleotide will hybridize under appropriate conditions. In some of these aspects, the method further comprises contacting the target polynucleotide and a complement of the target polynucleotide with the first polynucleotide and second polynucleotide and the third polynucleotide and fourth polynucleotide under conditions sufficient to allow hybridization of the first domain of the first polynucleotide to the first target polynucleotide region of the target polynucleotide, the first domain of the second polynucleotide to the second target polynucleotide region of the target polynucleotide, the first domain of the third polynucleotide to the first target domain of the complementary strand of the target polynucleotide and the first domain of the fourth polynucleotide to the second complement target polynucleotide region and extending the first domains (i.e., priming domains) of the first and fourth polynucleotides with a DNA polymerase under conditions which permit extension of the first polynucleotide and the third polynucleotide.

In some aspects, a blocking group as described herein above is attached to the second polynucleotide and/or the fourth polynucleotide at their 3' ends which blocks extension by an enzyme that is capable of synthesizing a nucleic acid. Blocking groups useful in the practice of the methods include but are not limited to a 3' phosphate group, a 3' amino group, a dideoxy nucleotide, and inverted deoxythymidine (dT).

In various embodiments, the target polynucleotide, the complement of the target polynucleotide or both has a secondary structure that is denatured by hybridization of the first domain of the second polynucleotide and/or the first domain of the fourth polynucleotide to a target polynucleotide.

Figure 7A:
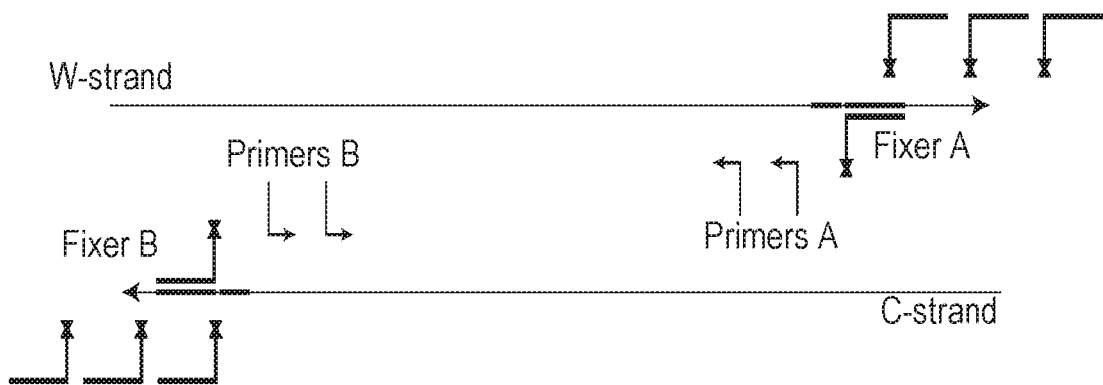
Figure 7B:
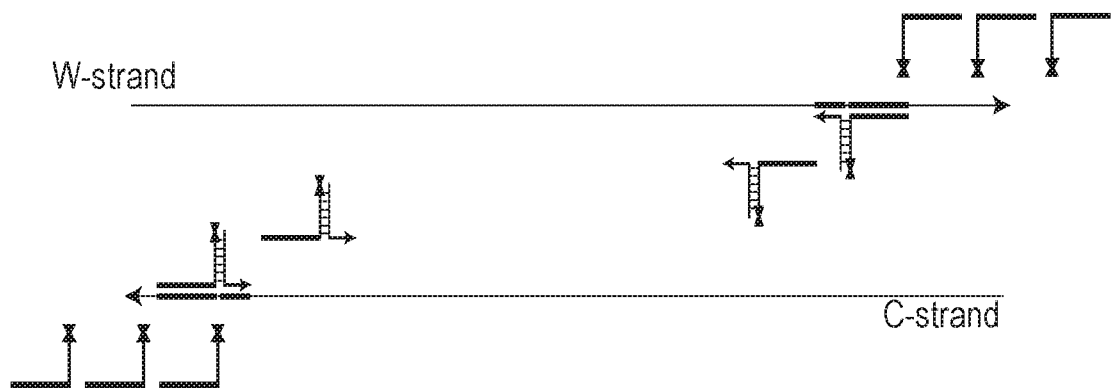
Figure 7C:
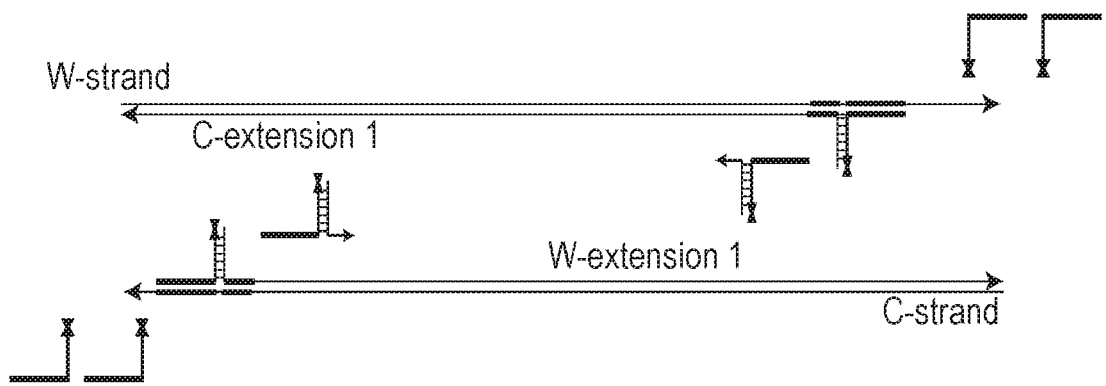
Figure 7D:
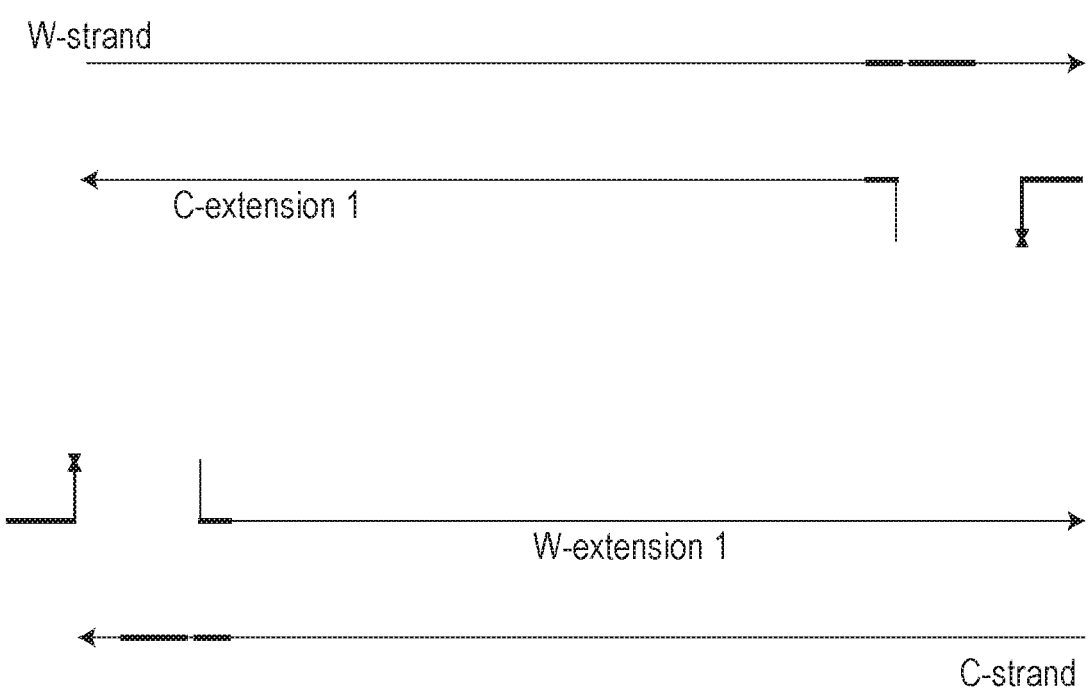
Figure 7E:
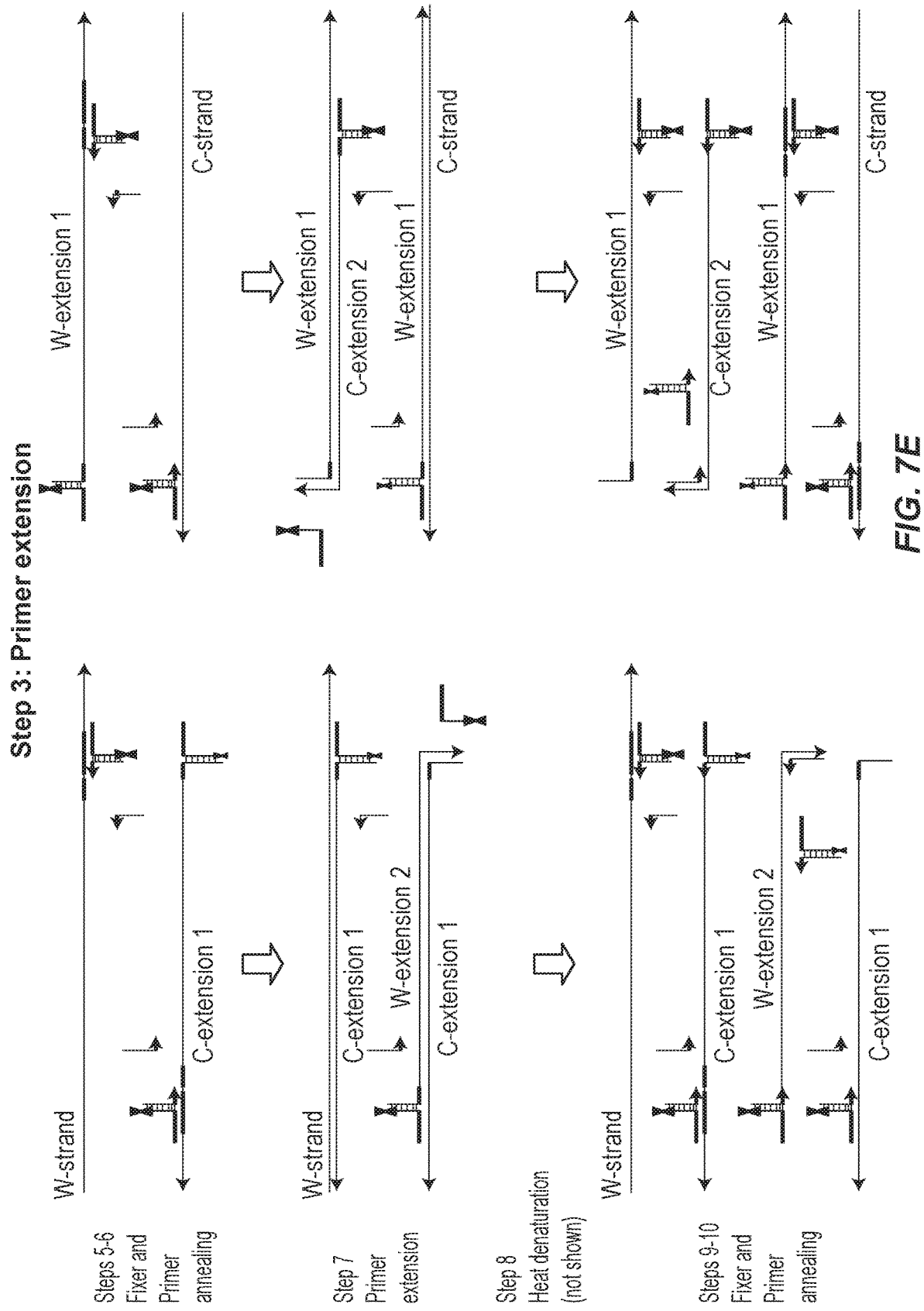

In an embodiment, the polynucleotide combinations are contemplated for use in PCR as depicted in FIG. 7a-f (Schemes 4-9). In Scheme 4, Primers A (i.e., the first polynucleotide as described herein) and B (i.e., the third polynucleotide as described herein) are used on opposite strands of the target polynucleotide, which are depicted as the W—(Watson) and C—(Crick) strands. As is shown in FIG. 7f (Scheme 9), following step 12 only the Primers A and B are required for amplification of the target polynucleotide.

One of ordinary skill in the art will recognize that the polynucleotide combinations of the present invention can be used to prime either one or both ends of a given PCR amplicon. As used herein, an "amplicon" is understood to mean a portion of a polynucleotide that has been synthesized using amplification techniques. It is contemplated that any of the methods of the present invention that comprise more than one polynucleotide combination may utilize any combination of standard primer and polynucleotide combination, provided at least one of the primers is a polynucleotide combination as described herein.

B. Simple Second Strand Synthesis

In another embodiment, a method of amplifying a target polynucleotide is provided using the first and second polynucleotides comprising contacting the target polynucleotide with the first and second polynucleotides disclosed herein under conditions sufficient to allow hybridization of the first domain of the first polynucleotide to the first target polynucleotide region of the target polynucleotide and the first domain of the second polynucleotide to the second target polynucleotide region of the target polynucleotide, and extending the first domain (i.e., priming domain) of the first polynucleotide with a DNA polymerase under conditions which permit extension of the first domain of the first polynucleotide. In some aspects, the first polynucleotide (with associated polynucleotide product extended therefrom) and second polynucleotide are then denatured from the target polynucleotide and another set of first and second polynucleotides are allowed to hybridize to a target polynucleotide.

In one aspect, the first polynucleotide and the second polynucleotide hybridize sequentially to the target polynucleotide. In another aspect, the first domain of the first polynucleotide hybridizes to the target before the first domain of the second polynucleotide hybridizes to the target polynucleotide. In yet another aspect, the first domain of the second polynucleotide hybridizes to the target polynucleotide before the first domain of the first polynucleotide hybridizes to the target polynucleotide. In another aspect, the first domain of the first polynucleotide and the first domain of the second polynucleotide hybridize to the target polynucleotide concurrently.

In various embodiments, the target polynucleotide includes but is not limited to chromosomal DNA, genomic DNA, plasmid DNA, cDNA, RNA, a synthetic polynucleotide, a single stranded polynucleotide, or a double stranded polynucleotide. In one aspect, the target is a double stranded polynucleotide and the first domain of the first polynucleotide and the first domain of the second polynucleotide hybridize to the same strand of the double stranded target polynucleotide. In another aspect, the second domain of the first polynucleotide and the second domain of the second polynucleotide hybridize prior to hybridization of the first polynucleotide and the second polynucleotide to the target polynucleotide.

In an embodiment, the first polynucleotide and the second polynucleotide hybridize to the target polynucleotide concurrently and the third polynucleotide and the fourth polynucleotide hybridize to the complement of the target polynucleotide concurrently, the first polynucleotide and the second polynucleotide hybridizing to the target polynucleotide at the same time that the third polynucleotide and the fourth polynucleotide hybridize to the complement of the target polynucleotide.

In another embodiment, the first polynucleotide, the second polynucleotide, the third polynucleotide and the fourth polynucleotide do not hybridize to the target polynucleotide and the complement of the target polynucleotide at the same time.

In yet another embodiment, the second domain of the first polynucleotide and the second domain of the second polynucleotide hybridize prior to hybridizing to the target polynucleotide. In another embodiment, the second domain of the third polynucleotide and the second domain of the fourth polynucleotide hybridize prior to hybridizing to the complement of the target polynucleotide.

In an embodiment, the second domain of the first polynucleotide and the second domain of the second polynucleotide hybridize prior to hybridizing to the target polynucleotide and the second domain of the third polynucleotide and the second domain of the fourth polynucleotide hybridize prior to hybridizing to the complement of the target polynucleotide.

In another embodiment, the target polynucleotide contains a mutation in the region to which the first domain of the first polynucleotide hybridizes to the target polynucleotide. In some embodiments, the target polynucleotide is fully complementary in the region to which the first domain of the first polynucleotide hybridizes to the target polynucleotide.

In some embodiments, the non-target polynucleotide is not fully complementary in the region to which the first domain of the first polynucleotide hybridizes to the non-target polynucleotide. In another embodiment, the target polynucleotide contains a mutation in the region to which the first domain of the third polynucleotide hybridizes to the target polynucleotide. In some embodiments, the target polynucleotide is fully complementary in the region to which the third domain of the first polynucleotide hybridizes to the target polynucleotide. In some embodiments, the non-target polynucleotide is not fully complementary in the region to which the third domain of the first polynucleotide hybridizes to the non-target polynucleotide. In some aspects, the mutation is a destabilizing mutation. In related aspects, the destabilizing mutation prevents extension of the first polynucleotide, or the third polynucleotide, or both.

C. Multiplexing

In an embodiment, the extension by an enzyme that is capable of synthesizing a nucleic acid is a multiplex extension, the first domain of the first polynucleotide having the property of hybridizing to more than one region in the target polynucleotide. In a related embodiment, the extension by an enzyme that is capable of synthesizing a nucleic acid is a multiplex extension, the first domain of the third polynucleotide having the property of hybridizing to more than one locus in the target polynucleotide.

In related embodiments, multiplex PCR is performed using at least two polynucleotide primers to amplify more than one polynucleotide product. In some aspects of these embodiments, each polynucleotide primer used for multiplex PCR is a polynucleotide combination as disclosed herein. In other aspects, at least one polynucleotide primer used for multiplex PCR is a polynucleotide combination as disclosed herein.

In another embodiment, multiplex PCR is performed using multiple fixer polynucleotides and are directed against genomic repeated sequences. In another embodiment, the fixer polynucleotides are comprised of random sequences. In some of these aspects, multiple fixer polynucleotides refers to about 10 polynucleotide sequences. In other aspects, multiple fixer polynucleotides refers to about 15, about 20, about 25, about 30, about 35, about 40, about 45, about 50, about 55, about 60, about 65, about 70, about 75, about 80, about 85, about 90, about 95, about 100, about 150, about 200, about 250, about 300, about 350, about 400, about 450, about 500, about 550, about 600, about 650, about 700, about 750, about 800, about 850, about 900, about 950, about 1000 or more polynucleotide sequences. These fixer polynucleotide sequences would provide a multitude of "fixed" locations in the genome to which a multitude of primer polynucleotides could then bind, taking advantage of the unique complementary polynucleotide sequences present in both the primer and fixer polynucleotides as described herein.

D. Real-Time PCR

Primer combinations with a standard three-way junction are useful for real-time PCR. Analysis and quantification of rare transcripts, detection of pathogens, diagnostics of rare cancer cells with mutations, or low levels of aberrant gene methylation in cancer patients are the problems that can be solved by improved real-time PCR assays that combine high sensitivity and specificity of target amplification, high specificity of target detection, the ability to selectively amplify and detect a small number of cancer-specific mutant alleles or abnormally methylated promoters in the presence of thousands of copies of normal DNA, analysis and quantification of low copy number RNA transcripts, detection of fluorescence traces the ability to multiplex 4-5 different targets in one assay to maximally utilize capabilities of current real-time thermal cyclers. A fluorophore is positioned at the 5' end of the primer polynucleotide, and a quencher is positioned at the 3' end of the fixer polynucleotide. In this arrangement, no fluorescence is detected when the primer and fixer polynucleotides are hybridized (since the fluorophore is positioned adjacent to the quencher). However, following extension of the primer polynucleotide during PCR, the primer polynucleotide and fixer polynucleotide will become separated during the denaturation phase of PCR, thus creating distance between the fluorophore and the quencher and resulting in a detectable fluorescent signal.

Primer combinations with a four-way junction can also be used for real-time PCR. The primer polynucleotide is labeled with a fluorophore on its 5' end, and the staple is labeled with a quencher on its 3' end. The fixer polynucleotide is unlabeled. Since the second domain regions of both the primer and fixer polynucleotides are unique, the staple polynucleotide can be used as a "universal" polynucleotide (FIG. 10; Scheme 10).

Primer combinations with a two-way junction and a probe polynucleotide can also be used for real-time PCR. The probe polynucleotide is labeled with a fluorophore on its 5' end, a quencher on its 3' end, and in some embodiments, an additional internal quencher. When the first polynucleotide is extended by a polymerase with 5' to 3' exonuclease activity, such as Taq polymerase, the label is cleaved and is no longer quenched, resulting in increased signal from the label. In some embodiments, the probe polynucleotide is a molecular beacon probe. In short, a molecular beacon probe is comprised of a nucleotide sequence with bases on its 5' and 3' ends that are complementary and form a hairpin structure in the absence of a target polynucleotide. The molecular beacon probe also comprises a quencher at its 3' end (or 5' end) and a fluorescent label at its 5' end (or 3' end) such that there is no detectable signal from the label when the target polynucleotide is not present. The molecular beacon probe also comprises a sequence that is complementary to the target polynucleotide such that, in the presence of the target, hybridization of the probe to the target polynucleotide causes the dissociation of the hairpin structure and loss of quenching, resulting in a detectable fluorescent signal.

Primer combinations with a two-way junction and a blocker polynucleotide can also be used in combination for real-time PCR. The primer polynucleotide (i.e., "first polynucleotide") is labeled with a fluorophore on its 5' end, and the fixer polynucleotide (i.e., "second polynucleotide") is labeled with a quencher on its 3' end. The blocker polynucleotide is complementary to a target polynucleotide region located immediately 5' of the first target polynucleotide region (depicted in FIG. 4). In some embodiments, the blocker polynucleotide overlaps with the first domain of the first polynucleotide. In other words, the nucleotide(s) at the 3' end of the first polynucleotide and the nucleotide(s) at the 5' end of the blocker polynucleotide would be complementary to the same nucleotide(s) of the target polynucleotide. In related embodiments, the nucleotide(s) at the 3' end of the first polynucleotide and the nucleotide(s) at the 5' end of the blocker polynucleotide are different. In these embodiments, the nucleotide(s) at the 3' end of the first polynucleotide would hybridize to the target polynucleotide when it is complementary to the target polynucleotide at the appropriate position(s), thus allowing for extension of the first polynucleotide under the appropriate conditions (see FIG. 4*a*). Following extension of the primer polynucleotide during PCR, the primer polynucleotide and fixer polynucleotide will become separated during the denaturation phase of PCR, thus creating distance between the fluorophore and the quencher and resulting in a detectable fluorescent signal. In related embodiments, the nucleotide at the 5' end of the blocker polynucleotide would hybridize to the non-target polynucleotide when it is complementary to the non-target polynucleotide at the appropriate position, thus blocking extension of the first polynucleotide. (see FIG. 4*b*). In this arrangement, no fluorescence is detected when the primer and fixer polynucleotides are hybridized (since the fluorophore is positioned adjacent to the quencher). In various embodiments, the nucleotide at the 3' end of the blocker polynucleotide is modified to prevent extension by a polymerase. This system allows for detection of, for example, single nucleotide polymorphisms with great sensitivity and specificity.

Primer combinations with two-way junctions, blocker polynucleotides, and probe polynucleotides are also used in combination for real-time PCR. In related embodiments, the first polynucleotide used in this combination comprises a modified nucleic acid as the nucleotide at its 3' end and the blocker polynucleotide comprises a modified nucleic acid as the nucleotide at its 5' end. In some embodiments, the modified nucleic acid is a locked nucleic acid.

In some aspects, the above embodiments further comprise a reverse primer polynucleotide. The reverse primer is complementary to a region in the polynucleotide created by extension of the first polynucleotide. See FIG. 8. As is apparent, in some embodiments the reverse primer is also complementary to the complementary strand of the target polynucleotide when the target polynucleotide is one strand of a double-stranded polynucleotide. Inclusion of a reverse primer allows for amplification of the target polynucleotide. In various aspect, the reverse primer is a "simple" primer wherein the sequence of the reverse primer is designed to be sufficiently complementary over its entire length to hybridize to a target sequence over the entire length of the primer. A simple primer of this type is in one aspect, 100% complementary to a target sequence, however, it will be appreciated that a simple primer with complementarity of less than 100% is useful under certain circumstances and conditions.

In other aspect, a reverse primer is a separate polynucleotide primer combination that specifically binds to regions in a sequence produced by extension of a polynucleotide from the first domain of the first polynucleotide in a primer pair combination used in a first reaction.

In various aspects, the methods described herein provide a change in sequence detection from a sample with a non-target polynucleotide compared to sequence detection from a sample with a target polynucleotide. In some aspects, the change is an increase in detection of a target polynucleotide in a sample compared to sequence detection from a sample with a non-target polynucleotide. In some aspects, the change is a decrease in detection of a target polynucleotide in a sample compared to sequence detection from a sample with a non-target polynucleotide.

Due to the increased specificity of the polynucleotides described herein, real-time PCR can be performed in the presence of SYBR green dye to achieve a specificity that is equivalent to that achieved using TaqMan, molecular beacon probes or Scorpion primers but at a greatly reduced cost.

In one embodiment, the primer polynucleotide (i.e., "first polynucleotide") is labeled with a fluorescent molecule at its 5' end and a second quenching polynucleotide (i.e., "universal quencher polynucleotide") that is labeled at its 3' end with a quencher are both hybridized to the second domain of the fixer polynucleotide (i.e., "second polynucleotide"), which comprises a blocking group at its 3' end to prevent extension from a DNA polymerase. This complex has no fluorescence in this state but will fluoresce when the complex is displaced (denatured) following extension of the primer polynucleotide by a DNA polymerase.

In another embodiment, the primer polynucleotide (i.e., "first polynucleotide") comprising a fluorophore at its 5' end is hybridized to a fixer polynucleotide (i.e., "second polynucleotide") comprising a quencher at its 3' end. The complex has no fluorescence when hybridized, but will fluoresce when the complex is displaced (denatured) following extension of the primer polynucleotide by a DNA polymerase. In another aspect of the method, multiplex real-time PCR is performed using two sets of polynucleotide combinations, wherein one polynucleotide in each primer set is labeled with a fluorophore, and the two fluorophores are distinguishable from each other.

In another embodiment, the primer polynucleotide (i.e., "first polynucleotide") comprises a fluorophore, a quencher on its 3' end, and these two labels are separated by a stretch of RNA or RNA/DNA oligonucleotides (i.e., "probe polynucleotide") (see FIG. 9). In some aspects, the probe polynucleotide further comprises an internal Zen quencher. In some aspects, a fluorescent signal is generated upon creation and degradation of the RNA/DNA hybrid by a thermostable RNase H and release of a free fluorophore (or quencher) into solution.

Figure 9A:
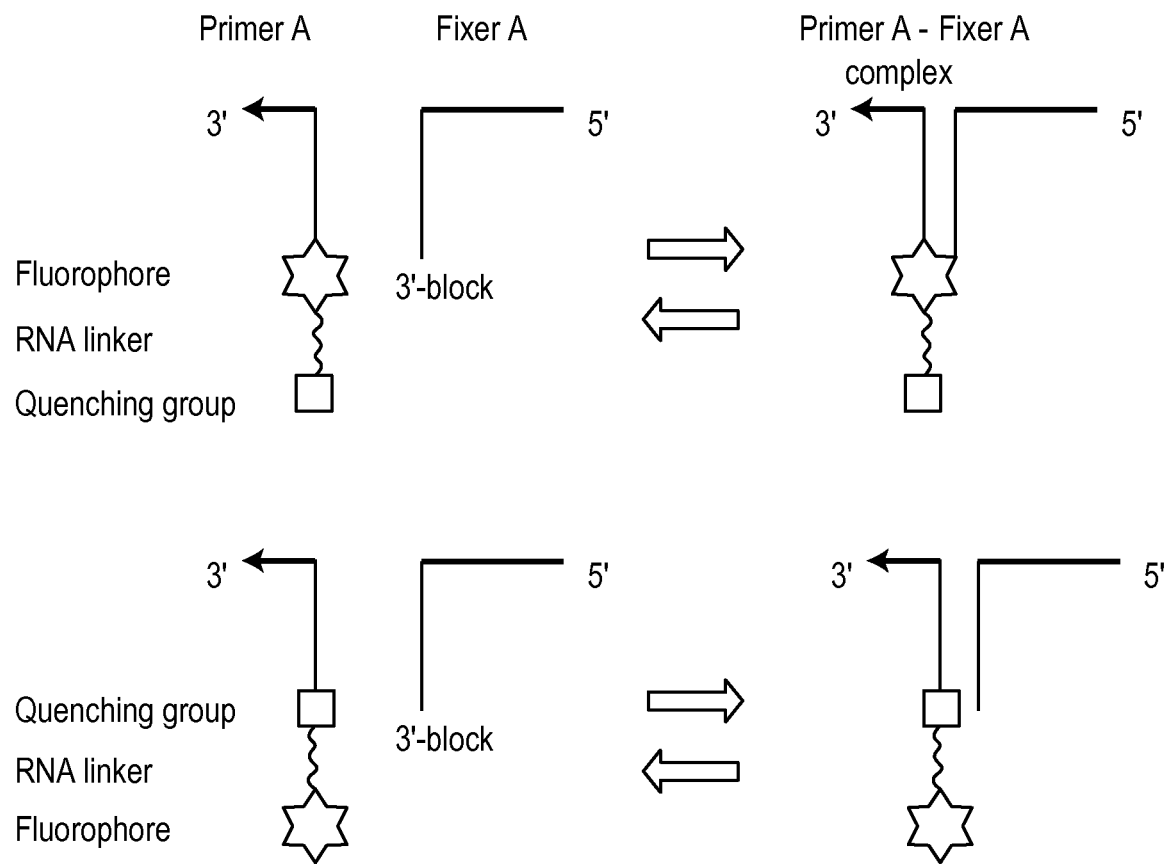
FIG. 9A depicts a fluorophore-quencher labeled first polynucleotide (Primer A) with a non-specific RNA linker and a typical second polynucleotide (Fixer A).
Figure 9B:
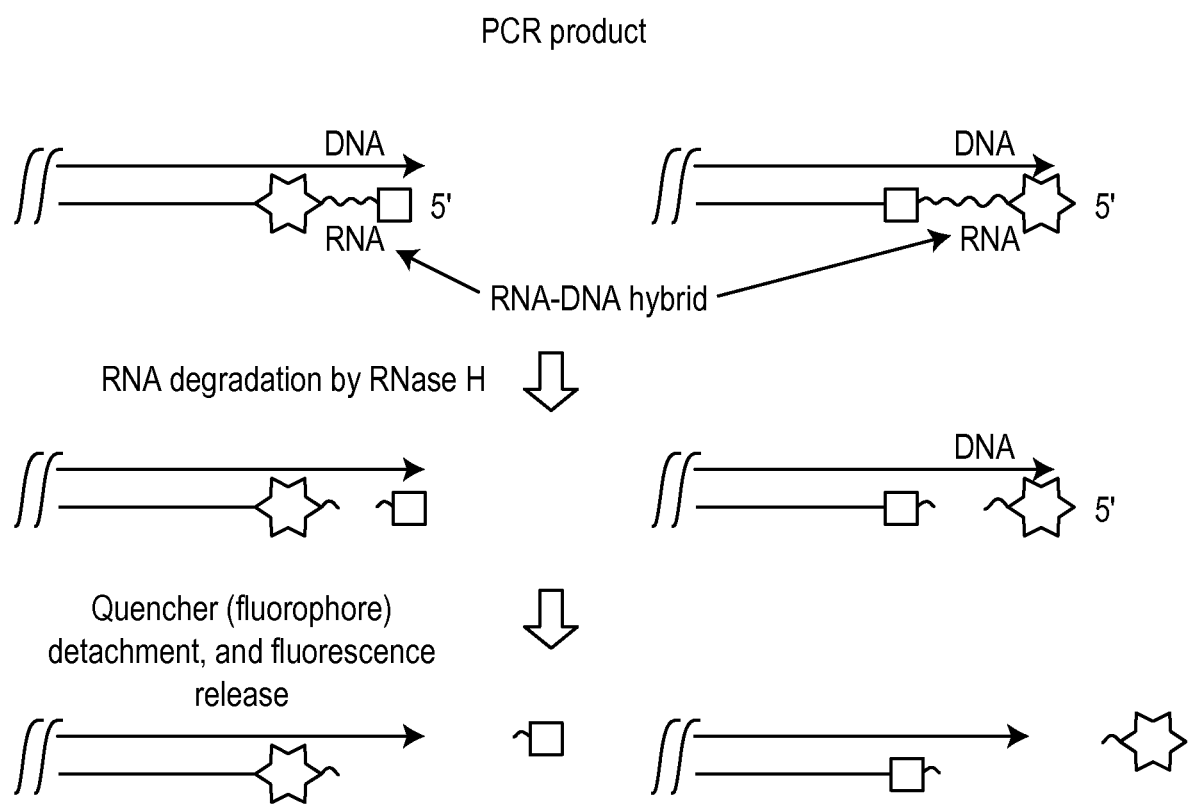
FIG. 9B illustrates the use of the combination depicted in FIG. 9A in PCR. When the strand opposite Primer A is generated, cleavage of the RNA-DNA hybrid by RNase H releases the fluorophore (or quencher) and a fluorescent signal is detected.

FIG. 9A depicts a fluorophore-quencher labeled first polynucleotide (Primer A) with a non-specific RNA linker and a typical second polynucleotide (Fixer A). In certain embodiments, the first polynucleotide (P) comprises a 5' label followed by an RNA sequence, followed by a quencher, followed by a sequence typical of first polynucleotides (P) described herein. In other embodiments, the first polynucleotide (P) comprises a 5' quencher followed by an RNA sequence, followed by a label, followed by a sequence typical of first polynucleotides (P) described herein. FIG. 9B illustrates the use of the combination depicted in FIG. 9A in PCR. When the strand opposite P is generated, cleavage of the RNA-DNA hybrid by RNase H releases the fluorophore (or quencher) and a fluorescent signal is detected.

Figure 9C:
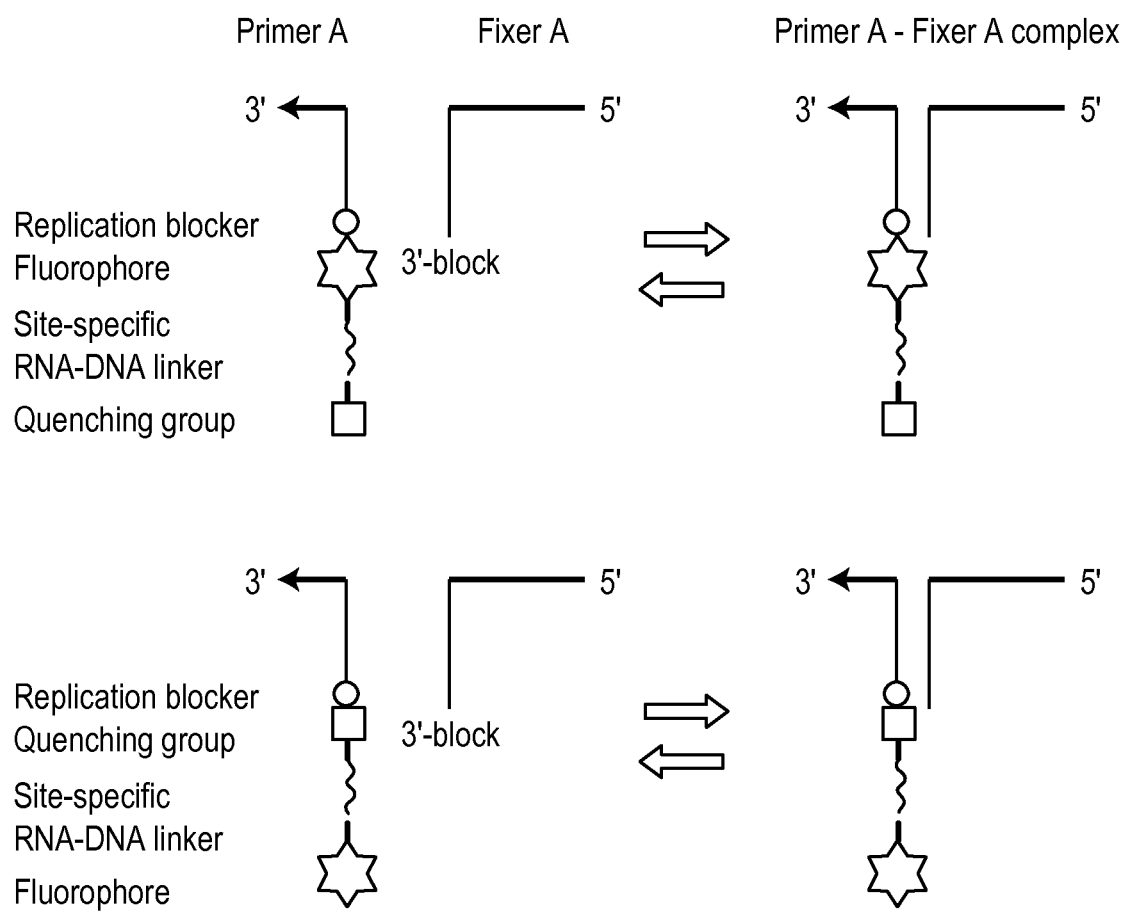
FIG. 9C depicts a fluorophore-quencher labeled first polynucleotide (Primer A) with a site-specific RNA-DNA linker and a typical second polynucleotide (Fixer A).

FIG. 9C depicts a fluorophore-quencher labeled first polynucleotide (Primer A) with a site-specific RNA-DNA linker and a typical second polynucleotide (Fixer A). In certain embodiments, the first polynucleotide (P) comprises a 5' label followed by an RNA sequence that is complementary to a sequence downstream of P, followed by a quencher, followed by a sequence typical of first polynucleotides (P) described herein. In certain embodiments, the first polynucleotide (P) comprises a 5' quencher, followed by an RNA sequence that is complementary to a sequence downstream of P, followed by a label, followed by a sequence typical of first polynucleotides (P) described herein. FIG. 9D illustrates the use of the combination depicted in FIG. 9C in PCR. When the PCR product comprising Primer A is denatured, the RNA-DNA linker hybridizes to a region downstream of Primer A, RNase H cleaves the RNA-DNA hybrid and releases the fluorophore and a fluorescent signal is detected.

In some embodiments, one fixer polynucleotide (i.e., "second polynucleotide") may be used in combination with 2, 3, 4, 5 or more primer polynucleotides (i.e., "first polynucleotides") for simultaneous multiplex detection of several mutations in one real-time PCR assay.

In another embodiment, a kit is provided comprising, e.g., a package insert, a set of four fluorescently labeled universal polynucleotide molecules, a universal polynucleotide molecule comprising a quencher at its 3' end, and a DNA ligase with appropriate buffer for assembly of the fluorescently labeled primer polynucleotide. The kit optionally further comprises a T4 polynucleotide kinase and appropriate buffer.

The kit is used to fluorescently label polynucleotides through ligation. In one embodiment, a primer polynucleotide is phosphorylated with T4 polynucleotide kinase and is subsequently hybridized to a fixer polynucleotide. A third polynucleotide (i.e., a fluorescently labeled universal polynucleotide, see above) comprising a fluorophore at its 5' end is likewise hybridized to the fixer polynucleotide. The 3' end of the third polynucleotide is then ligated to the phosphorylated 5' end of the primer polynucleotide, creating a fluorescently-labeled primer polynucleotide. Finally, a universal polynucleotide comprising a quencher at its 3' end is hybridized to the fixer polynucleotide, resulting in a polynucleotide complex that has no fluorescence and is ready for use in, e.g., a real-time PCR analysis.

E. Primer Extension

The primer compositions disclosed herein can be used in any method requiring or utilizing primer extension. For example, primer extension can be used to determine the start site of RNA transcription for a known gene. This technique requires a labeled primer polynucleotide combination as described herein (usually 20-50 nucleotides in length) which is complementary to a region near the 3' end of the gene. The polynucleotide combination is allowed to anneal to the RNA and reverse transcriptase is used to synthesize complementary (cDNA) to the RNA until it reaches the 5' end of the RNA. By analyzing the product on a polyacrylamide gel, it is possible to determine the transcriptional start site, as the length of the sequence on the gel represents the distance from the start site to the labeled primer.

The advanced polynucleotide technology described herein would overcome and resolve potential secondary structure encountered in RNA.

F. Isothermal DNA Amplification

Isothermal DNA amplification may be performed as taught in U.S. Pat. No. 7,579,153 using the advanced polynucleotide technology described herein. Briefly, isothermal DNA amplification comprises the following steps: (i) providing a double stranded DNA having a hairpin at one end, the polynucleotide at the other end, and disposed therebetween a promoter sequence oriented so that synthesis by an RNA polymerase recognizing the promoter sequence proceeds in the direction of the hairpin; (ii) transcribing the double stranded DNA with an RNA polymerase that recognizes the promoter sequence to form an RNA transcript comprising copies of the promoter sequence and the polynucleotide; (iii) generating a complementary DNA from the RNA transcript; (iv) displacing a 5' end of the RNA transcript from the complementary DNA so that the hairpin is reconstituted; and (v) extending the hairpin to generate the double stranded DNA containing a reconstituted promoter sequence, the RNA polymerase recognizing the reconstituted promoter sequence and synthesizing RNA transcripts. In a preferred embodiment, the step of generating includes forming a heteroduplex of said complementary DNA and said RNA transcript and wherein said step of displacing includes treating the heteroduplex with a helicase.

G. Fluorescence In Situ Hybridization (FISH)

The advanced polynucleotide technology described herein can also be used to practice FISH. FISH is a cytogenetic technique used to detect and localize the presence or absence of specific DNA sequences on chromosomes. FISH uses fluorescent probes that bind to only those parts of the chromosome with which they show a high degree of sequence similarity. Fluorescence microscopy can be used to find out where the fluorescent probe bound to the chromosomes. FISH is often used for finding specific features in DNA for use in genetic counseling, medicine, and species identification. FISH can also be used to detect and localize specific mRNAs within tissue samples. In this context, it can help define the spatial-temporal patterns of gene expression within cells and tissues.

H. Ligation Probes

The advanced polynucleotide technology described herein can also be used to practice multiplex PCR using ligation probes. Ligation probe methods are known to those of skill in the art. Briefly, ligation probes consist of two separate oligonucleotides, each containing a PCR primer sequence. It is only when these two hemi probes are both hybridized to their adjacent targets that they can be ligated. Only ligated probes will be amplified exponentially in a PCR. The number of probe ligation products therefore depends on the number of target sequences in the sample.

In some embodiments, two ligation probes are separated by about 1 to about 500 nucleotides, and prior to ligation the first probe is extended by a DNA thermostable polymerase lacking strand-displacement activity. A DNA thermostable polymerase lacking strand-displacement activity includes, but is not limited to, a Pfu polymerase. When the extended strand reaches the 5'-phosphate group of the second ligation probe, polymerization stops and a nick is created. This nick can be sealed by a thermostable ligase present in the reaction mixture, allowing for the entire reaction to occur in a single-reaction format.

I. Next Generation Sequencing (NGS)

The polynucleotide combinations of the present invention may also be used in NGS applications. Instead of sequencing by sequential ligation of DNA probes, the primer combinations disclosed herein can be used in sequential hybridization without ligation, as shown in FIG. 15. For a review of NGS technology, see Morozova et al., Genomics 92(5): 255-64, 2008, incorporated herein by reference in its entirety. NGS is readily understood and practiced by those of ordinary skill in the art and exemplified in one embodiment as set out below in Example 2.

X. Enzymes

In some aspects of any of the methods, the extension is performed by an enzyme that is capable of synthesizing a nucleic acid is quantitated in real-time. The enzymes useful in the practice of the invention include but are not limited to a DNA polymerase (which can include a thermostable DNA polymerase, e.g., a Taq DNA polymerase), RNA polymerase, and reverse transcriptase. Non-limiting examples of enzymes that may be used to practice the present invention include but are not limited to Deep VentR™ DNA Polymerase, LongAmp™ Taq DNA Polymerase, Phusion™ High-Fidelity DNA Polymerase, Phusion™ Hot Start High-Fidelity DNA Polymerase, VentR® DNA Polymerase, DyNAzyme™ II Hot Start DNA Polymerase, Phire™ Hot Start DNA Polymerase, Phusion™ Hot Start High-Fidelity DNA Polymerase, Crimson LongAmp™ Taq DNA Polymerase, DyNAzyme™ EXT DNA Polymerase, LongAmp™ Taq DNA Polymerase, Phusion™ High-Fidelity DNA Polymerase, Phusion™ Hot Start High-Fidelity DNA Polymerase, Taq DNA Polymerase with Standard Taq (Mg-free) Buffer, Taq DNA Polymerase with Standard Taq Buffer, Taq DNA Polymerase with ThermoPol II (Mg-free) Buffer, Taq DNA Polymerase with ThermoPol Buffer, Crimson Taq™ DNA Polymerase, Crimson Taq™ DNA Polymerase with (Mg-free) Buffer, Phire™ Hot Start DNA Polymerase, Phusion™ High-Fidelity DNA Polymerase, VentR® DNA Polymerase, VentR® (exo-) DNA Polymerase, Phire™ Hot Start DNA Polymerase, Phusion™ High-Fidelity DNA Polymerase, Phusion™ Hot Start High-Fidelity DNA Polymerase, Hemo KlenTaq™, Deep VentR™ (exo-) DNA Polymerase, Deep VentR™ DNA Polymerase, DyNAzyme™ EXT DNA Polymerase, Hemo KlenTaq™, LongAmp™ Taq DNA Polymerase, Phusion™ High-Fidelity DNA Polymerase, ProtoScript® AMV First Strand cDNA Synthesis Kit, ProtoScript® M-MuLV First Strand cDNA Synthesis Kit, Bst DNA Polymerase, Full Length, Bst DNA Polymerase, Large Fragment, Taq DNA Polymerase with ThermoPol Buffer, 9° Nm DNA Polymerase, Crimson Taq™ DNA Polymerase, Crimson Taq™ DNA Polymerase with (Mg-free) Buffer, Deep VentR™ (exo-) DNA Polymerase, Deep VentR™ DNA Polymerase, DyNAzyme™ EXT DNA Polymerase, DyNAzyme™ II Hot Start DNA Polymerase, Hemo KlenTaq™, Phusion™ High-Fidelity DNA Polymerase, Phusion™ Hot Start High-Fidelity DNA Polymerase, Sulfolobus DNA Polymerase IV, Therminator™ γ DNA Polymerase, Therminator™ DNA Polymerase, Therminator™ II DNA Polymerase, Therminator™ III DNA Polymerase, VentR® DNA Polymerase, VentR® (exo-) DNA Polymerase, Bsu DNA Polymerase, Large Fragment, DNA Polymerase I (*E. coli*), DNA Polymerase I, Large (Klenow) Fragment, Klenow Fragment (3'→5' exo-), phi29 DNA Polymerase, T4 DNA Polymerase, T7 DNA Polymerase (unmodified), Terminal Transferase, Reverse Transcriptases and RNA Polymerases, *E. coli* Poly(A) Polymerase, AMV Reverse Transcriptase, M-MuLV Reverse Transcriptase, phi6 RNA Polymerase (RdRP), Poly(U) Polymerase, SP6 RNA Polymerase, and T7 RNA Polymerase.

XI. Labels

In some aspects, the first polynucleotide comprises a label. In other aspects, any polynucleotide used in the methods described herein comprises a label. In some of these aspects the label is fluorescent. Methods of labeling oligonucleotides with fluorescent molecules and measuring fluorescence are well known in the art. Fluorescent labels useful in the practice of the invention include but are not limited to 1,8-ANS (1-Anilinonaphthalene-8-sulfonic acid), 1-Anilinonaphthalene-8-sulfonic acid (1,8-ANS), 5-(and-6)-Carboxy-2',7'-dichlorofluorescein pH 9.0, 5-FAM pH 9.0, 5-ROX (5-Carboxy-X-rhodamine, triethylammonium salt), 5-ROX pH 7.0, 5-TAMRA, 5-TAMRA pH 7.0, 5-TAMRA-MeOH, 6 JOE, 6,8-Difluoro-7-hydroxy-4-methylcoumarin pH 9.0, 6-Carboxyrhodamine 6G pH 7.0, 6-Carboxyrhodamine 6G, hydrochloride, 6-HEX, SE pH 9.0, 6-TET, SE pH 9.0, 7-Amino-4-methylcoumarin pH 7.0, 7-Hydroxy-4-methylcoumarin, 7-Hydroxy-4-methylcoumarin pH 9.0, Alexa 350, Alexa 405, Alexa 430, Alexa 488, Alexa 532, Alexa 546, Alexa 555, Alexa 568, Alexa 594, Alexa 647, Alexa 660, Alexa 680, Alexa 700, Alexa Fluor 430 antibody conjugate pH 7.2, Alexa Fluor 488 antibody conjugate pH 8.0, Alexa Fluor 488 hydrazide-water, Alexa Fluor 532 antibody conjugate pH 7.2, Alexa Fluor 555 antibody conjugate pH 7.2, Alexa Fluor 568 antibody conjugate pH 7.2, Alexa Fluor 610 R-phycoerythrin streptavidin pH 7.2, Alexa Fluor 647 antibody conjugate pH 7.2, Alexa Fluor 647 R-phycoerythrin streptavidin pH 7.2, Alexa Fluor 660 antibody conjugate pH 7.2, Alexa Fluor 680 antibody conjugate pH 7.2, Alexa Fluor 700 antibody conjugate pH 7.2, Allophycocyanin pH 7.5, AMCA conjugate, Amino Coumarin, APC (allophycocyanin), Atto 647, BCECF pH 5.5, BCECF pH 9.0, BFP (Blue Fluorescent Protein), BO-PRO-1-DNA, BO-PRO-3-DNA, BOBO-1-DNA, BOBO-3-DNA, BODIPY 650/665-X, MeOH, BODIPY FL conjugate, BODIPY FL, MeOH, Bodipy R6G SE, BODIPY R6G, MeOH, BODIPY TMR-X antibody conjugate pH 7.2, Bodipy TMR-X conjugate, BODIPY TMR-X, MeOH, BODIPY TMR-X, SE, BODIPY TR-X phallacidin pH 7.0, BODIPY TR-X, MeOH, BODIPY TR-X, SE, BOPRO-1, BOPRO-3, Calcein, Calcein pH 9.0, Calcium Crimson, Calcium Crimson Ca2+, Calcium Green, Calcium Green-1 Ca2+, Calcium Orange, Calcium Orange Ca2+, Carboxynaphthofluorescein pH 10.0, Cascade Blue, Cascade Blue BSA pH 7.0, Cascade Yellow, Cascade Yellow antibody conjugate pH 8.0, CFDA, CFP (Cyan Fluorescent Protein), CI-NERF pH 2.5, CI-NERF pH 6.0, Citrine, Coumarin, Cy 2, Cy 3, Cy 3.5, Cy 5, Cy 5.5, CyQUANT GR-DNA, Dansyl Cadaverine, Dansyl Cadaverine, MeOH, DAPI, DAPI-DNA, Dapoxyl (2-aminoethyl) sulfonamide, DDAO pH 9.0, Di-8 ANEPPS, Di-8-ANEPPS-lipid, DiI, DiO, DM-NERF pH 4.0, DM-NERF pH 7.0, DsRed, DTAF, dTomato, eCFP (Enhanced Cyan Fluorescent Protein), eGFP (Enhanced Green Fluorescent Protein), Eosin, Eosin antibody conjugate pH 8.0, Erythrosin-5-isothiocyanate pH 9.0, Ethidium Bromide, Ethidium homodimer, Ethidium homodimer-1-DNA, eYFP (Enhanced Yellow Fluorescent Protein), FDA, FITC, FITC antibody conjugate pH 8.0, FlAsH, Fluo-3, Fluo-3 Ca2+, Fluo-4, Fluor-Ruby, Fluorescein, Fluorescein 0.1 M NaOH, Fluorescein antibody conjugate pH 8.0, Fluorescein dextran pH 8.0, Fluorescein pH 9.0, Fluoro-Emerald, FM 1-43, FM 1-43 lipid, FM 4-64, FM 4-64, 2% CHAPS, Fura Red Ca2+, Fura Red, high Ca, Fura Red, low Ca, Fura-2 Ca2+, Fura-2, high Ca, Fura-2, no Ca, GFP (S65T), HcRed, Hoechst 33258, Hoechst 33258-DNA, Hoechst 33342, Indo-1 Ca2+, Indo-1, Ca free, Indo-1, Ca saturated, JC-1, JC-1 pH 8.2, Lissamine rhodamine, LOLO-1-DNA, Lucifer Yellow, CH, LysoSensor Blue, LysoSensor Blue pH 5.0, LysoSensor Green, LysoSensor Green pH 5.0, LysoSensor Yellow pH 3.0, LysoSensor Yellow pH 9.0, LysoTracker Blue, LysoTracker Green, LysoTracker Red, Magnesium Green, Magnesium Green Mg2+, Magnesium Orange, Marina Blue, mBanana, mCherry, mHoneydew, MitoTracker Green, MitoTracker Green FM, MeOH, MitoTracker Orange, MitoTracker Orange, MeOH, MitoTracker Red, MitoTracker Red, MeOH, mOrange, mPlum, mRFP, mStrawberry, mTangerine, NBD-X, NBD-X, MeOH, NeuroTrace 500/525, green fluorescent Niss1 stain-RNA, Nile Blue, EtOH, Nile Red, Nile Red-lipid, Niss1, Oregon Green 488, Oregon Green 488 antibody conjugate pH 8.0, Oregon Green 514, Oregon Green 514 antibody conjugate pH 8.0, Pacific Blue, Pacific Blue antibody conjugate pH 8.0, Phycoerythrin, PO-PRO-1, PO-PRO-1-DNA, PO-PRO-3, PO-PRO-3-DNA, POPO-1, POPO-1-DNA, POPO-3, Propidium Iodide, Propidium Iodide-DNA, R-Phycoerythrin pH 7.5, ReAsH, Resorufin, Resorufin pH 9.0, Rhod-2, Rhod-2 Ca2+, Rhodamine, Rhodamine 110, Rhodamine 110 pH 7.0, Rhodamine 123, MeOH, Rhodamine Green, Rhodamine phalloidin pH 7.0, Rhodamine Red-X antibody conjugate pH 8.0, Rhodaminen Green pH 7.0, Rhodol Green antibody conjugate pH 8.0, Sapphire, SBFI-Na+, Sodium Green Na+, Sulforhodamine 101, SYBR Green I, SYPRO Ruby, SYTO 13-DNA, SYTO 45-DNA, SYTOX Blue-DNA, Tetramethylrhodamine antibody conjugate pH 8.0, Tetramethylrhodamine dextran pH 7.0, Texas Red-X antibody conjugate pH 7.2, TO-PRO-1-DNA, TO-PRO-3-DNA, TOTO-1-DNA, TOTO-3-DNA, TRITC, X-Rhod-1 Ca2+, YO-PRO-1-DNA, YO-PRO-3-DNA, YOYO-1-DNA, and YOYO-3-DNA.

Other labels besides fluorescent molecules can be used, such as chemiluminescent molecules, which will give a detectable signal or a change in detectable signal upon hybridization, and radioactive molecules.

In some embodiments, the second polynucleotide comprises a quencher that attenuates the fluorescence signal of a label. In other embodiments, the fourth polynucleotide comprises a quencher that attenuates the fluorescence signal of a label. Quenchers contemplated for use in practice of the methods of the invention include but are not limited to Black Hole Quencher 1, Black Hole Quencher-2, Iowa Black FQ, Iowa Black RQ, Zen quencher, and Dabcyl. G-base.

XII. Modified Polynucleotide Combinations

Partially double-stranded primer combinations with modified properties can be formed: (1) By two polynucleotides such as a basic primer polynucleotide and a basic fixer polynucleotide; (2) By two polynucleotides such as a modified primer polynucleotide and a basic fixer polynucleotide; (3) By two polynucleotides such as a modified primer polynucleotide and a modified fixer polynucleotide; (4) By three polynucleotides such as a basic primer polynucleotide, a basic fixer polynucleotide and an anti-primer polynucleotide; (5) By three polynucleotides such as a modified primer polynucleotide, a basic fixer polynucleotide and an anti-primer polynucleotide.

Partially double-stranded polynucleotides can initiate hybridization to genomic DNA only by its single-stranded region that can be located within the linear portion of a polynucleotide or within the loop region.

Non-complete sequence complementarity (including a single nucleotide mismatch) within the single-stranded region of the polynucleotide significantly reduces the efficiency of hybridization by slowing down the initiation of hybridization.

Non-complete sequence complementarity within the double-stranded region of the polynucleotide should interfere with strand-displacement hybridization and binding of the polynucleotide to the template polynucleotide.

Modified polynucleotides that are more sensitive to changes in template polynucleotide sequence than the basic polynucleotides can be used for development of more specific PCR-based diagnostic assays and for more sensitive PCR detection of rare DNA mutations in, e.g., cancer tissues.

Figure 11:
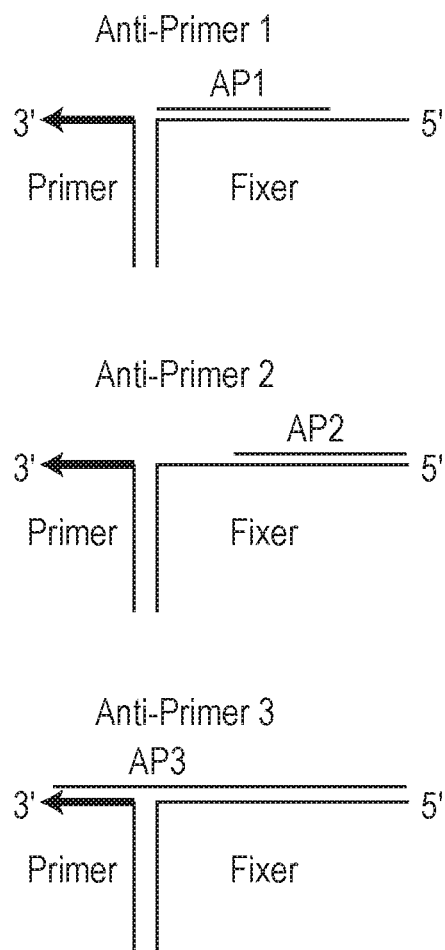
FIG. 11 depicts three examples utilizing basic primer and fixer polynucleotides with a non-covalently attached anti-primer (AP).

FIG. 11 (Scheme 11) depicts three examples utilizing basic primer and fixer polynucleotides with a non-covalently attached anti-primer (AP).

Figure 12:
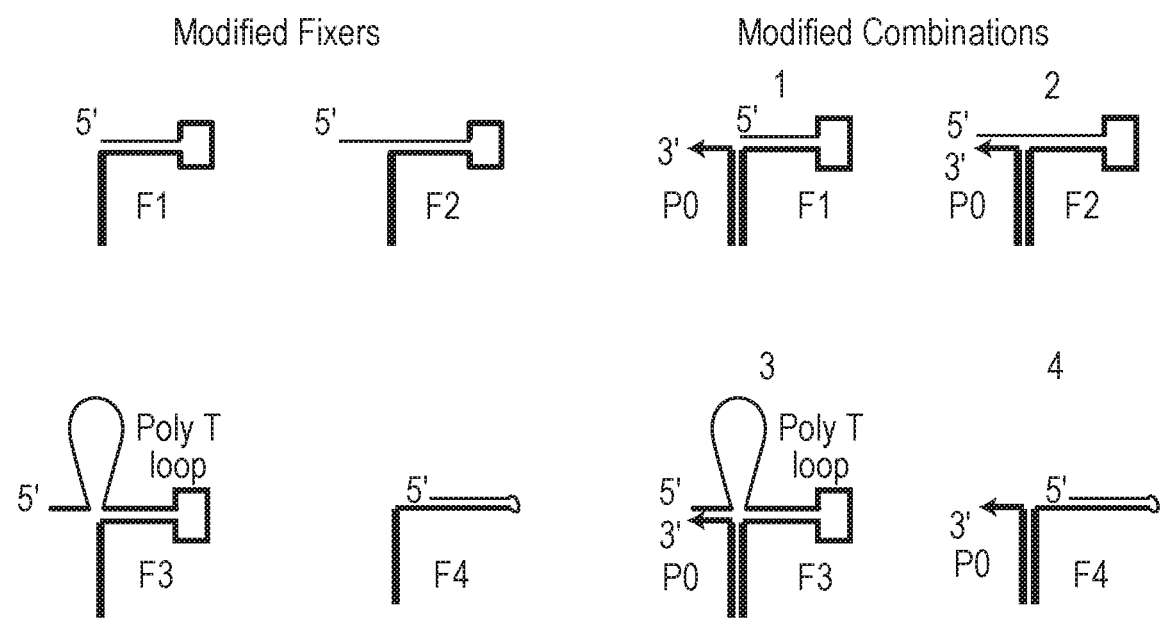
FIG. 12 depicts polynucleotides constructed with a basic primer polynucleotide ("P0") and a modified fixer polynucleotide structure ("F1 through F4"). The modified polynucleotide combinations comprising the stem loop structures (1 through 4) may be utilized to provide an increased level of specificity when binding to a template polynucleotide.

In another embodiment, polynucleotides may be constructed with a basic primer polynucleotide ("P0") and a modified fixer polynucleotide structure ("F1 through F4") (see FIG. 12; Scheme 12). The modified fixers are shown on the left, with the complete polynucleotide combinations (basic primer and modified fixer polynucleotides) shown on the right.

The modified polynucleotide combinations comprising the stem loop structures (1 through 4, Scheme 12) may be utilized to provide an increased level of specificity when binding to a template polynucleotide. In these aspects, a single-stranded region (e.g., in a loop structure) hybridizes to a template polynucleotide. This hybridization, if 100% complementary in sequence, will efficiently displace to a fully complementary stem portion of the fixer polynucleotide. In a related aspect, a primer polynucleotide can then hybridize to the fully-hybridized fixer polynucleotide. Any mutations within the single-stranded loop or the double-stranded stem regions of the modified fixer polynucleotide will reduce its hybridization efficiency and, as a result, the priming efficiency of the polynucleotide combination.

Figure 13B:
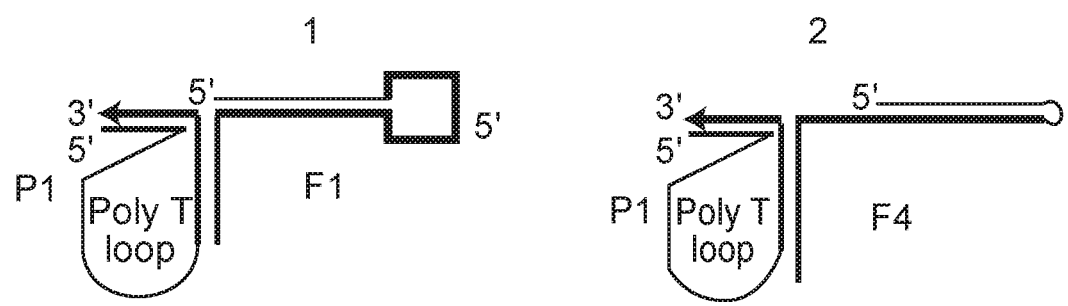
Figure 13C:
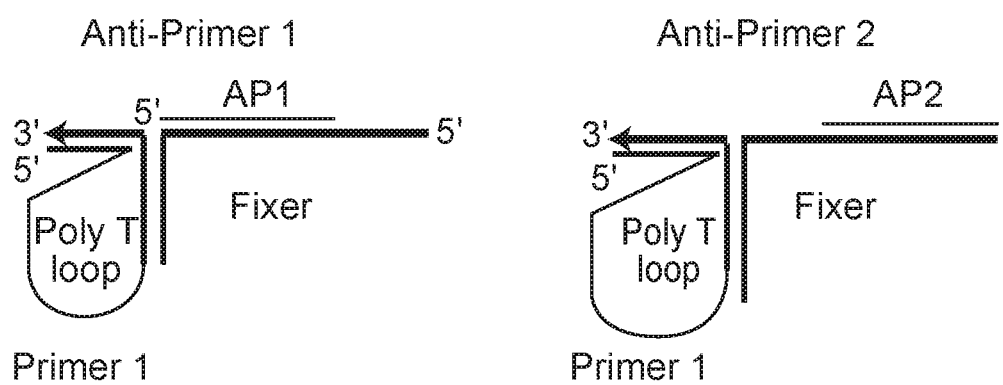

In another embodiment, polynucleotide combinations may be constructed with a modified primer polynucleotide ("P1") and a basic fixer polynucleotide ("F") (see FIG. 13a; Scheme 13). In Scheme 13, the modified primer polynucleotide is shown on the left, with the complete polynucleotide combination (modified primer polynucleotide and basic fixer polynucleotide) shown on the right. In this embodiment, the single-stranded DNA linker (comprised of, e.g., poly dT) should be long enough to allow the 5' segment of primer 1 to hybridize to its 3' segment.

In another embodiment, polynucleotide combinations may be constructed with a modified primer polynucleotide (Primer 1, P1) and a modified fixer polynucleotide (see Scheme 14). Two such examples are shown in FIG. 12b (Scheme 14), shown with modified fixer polynucleotides F1 and F4, from FIG. 12 (Scheme 12).

In another embodiment, polynucleotide combinations with a modified primer structure further comprise non-covalently attached anti-primers. In one aspect, polynucleotide combinations may be formed that comprise a modified primer polynucleotide, a basic fixer polynucleotide and an anti-primer. In various aspects, the anti-primer may be hybridized to different regions of the polynucleotide combination (see FIG. 12c; Scheme 15).

Anti-primer polynucleotides serve to further increase the specificity of binding of the first domain of the fixer polynucleotide to the template polynucleotide. Here, only 100% complementary template polynucleotide regions will efficiently hybridize to the short polynucleotide region that is not covered by the anti-primer. As the first domain of the fixer polynucleotide hybridizes to the template polynucleotide, it will displace the anti-primer if the template region is 100% complementary to the fixer polynucleotide. This provides an extra level of specificity versus the fixer polynucleotide alone.

The references cited herein throughout, to the extent that they provide exemplary procedural or other details supplementary to those set forth herein, are all specifically incorporated herein by reference.

EXAMPLES

A person of skill in the art will appreciate that when primers or primer combinations are referred to as being in "forward" or "reverse" orientations, these designations are arbitrary conventions used in describing PCR reactions and the structural relationship of the primers and the template. Thus, as is apparent to a person of skill in the art, re-orienting a PCR schematic diagram by flipping it 180° would result in "forward" primers becoming "reverse" primers and "reverse" primers becoming "forward" primers, and as such, designation of, for example, one primer combination as a forward primer or a reverse primer is not a limitation on the structure or use of that particular primer combination.

Example 1

Basic Single Base Mutation Detection PCR Using Polynucleotide Combinations of the Invention In one of its most basic forms, PCR is performed using two polynucleotide combinations. One polynucleotide combination is the "forward" complex and the other is the "reverse" complex. Each polynucleotide combination is comprised of two polynucleotides, a primer and a fixer. The primer and fixer polynucleotides are able to hybridize to each other as well as to a template DNA polynucleotide, as depicted in Scheme 2 (FIG. 2).

In the case of mutation detection, the forward and/or reverse primer polynucleotides contain a sequence that is able to discern a mutant from a wild type sequence in a target DNA polynucleotide. If the primer polynucleotide sequence is directed to a wild type sequence, then the primer polynucleotide will only bind efficiently to a wild type template, and vice versa. This result is because the mutant sequence will differ from the wild type sequence at only a single base position, and an aspect of the polynucleotide combinations described herein is that the first domain of the primer polynucleotide that hybridizes to the template polynucleotide is short (5 to 30 nucleotides). This length allows for the discrimination of mutant and wild type sequences, since if there is a mismatch the primer oligonucleotide binding will be unstable and consequently unable to prime DNA synthesis.

The first step is to assemble the reagents in a reaction vessel. The reagents comprise the forward and reverse polynucleotide combination complexes, a template DNA polynucleotide, a thermostable DNA polymerase, deoxynucleotide substrates, and a suitable buffer. The PCR is carried out according to methods well known in the art, using optimized conditions that are easily determined by those of skill in the art.

Depending on how the primer polynucleotides are designed (i.e., whether they are designed to detect a mutant or wild type allele) the resulting PCR products provides information on whether the sample contains a mutant or wild type allele (or both).

Figure 14:
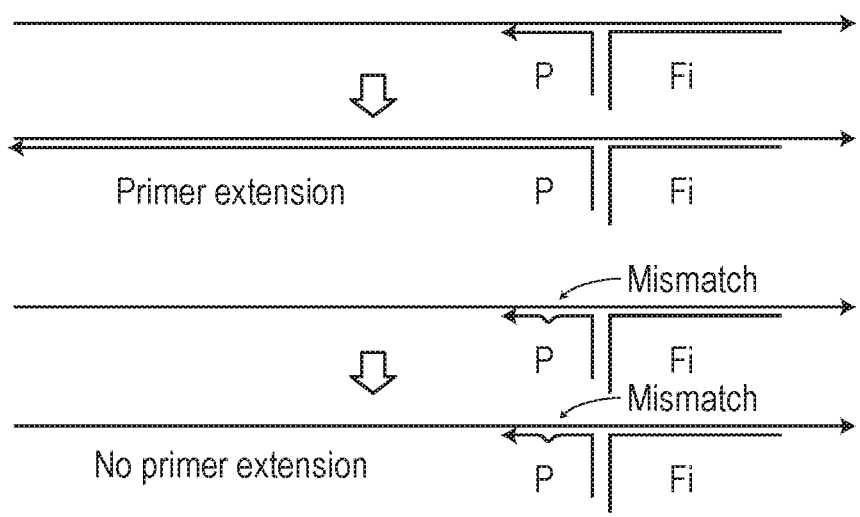
FIG. 14 depicts two scenarios for using the basic polynucleotide combination (i.e., first polynucleotide and second polynucleotide) disclosed herein to detect point mutations. In the top scenario, the first domain of a primer polynucleotide is 100% complementary to the template DNA polynucleotide and extension occurs, yielding a product. In the bottom scenario, the first domain of the primer polynucleotide contains a mismatch relative to the template DNA polynucleotide and extension is blocked due to the instability in the short first domain of the primer polynucleotide. This instability will result in a very low efficiency of PCR and will yield very little or no detectable product.

FIG. 14 (Scheme 16) depicts the two scenarios. In the top scenario, the first domain of a primer polynucleotide is 100% complementary to the template DNA polynucleotide and extension occurs, yielding a product.

In the bottom scenario, the first domain of the primer polynucleotide contains a mismatch relative to the template DNA polynucleotide and extension is blocked due to the instability in the short first domain of the primer polynucleotide. This instability will result in a very low efficiency of PCR and will yield very little or no detectable product.

Example 2

Next Generation Sequencing

Use of a polynucleotide combination to perform next generation sequencing (NGS) is performed without the use of either probe ligation or polymerase extension (FIG. 15; Scheme 17).

First, a first fixer polynucleotide and a mixture of four fluorescently labeled polynucleotides are hybridized to a polynucleotide template. The template with bound polynucleotides is then washed and the signal is read.

Next, the fluorescent label is cleaved and the mixture is washed again. Then a mixture of four fluorescently labeled polynucleotides are hybridized to the template polynucleotide, the mixture is washed and the signal is read again.

The first two steps are repeated until the end of the template is reached. Then the first fixer polynucleotide and all hybridized polynucleotides are stripped from the template polynucleotide. This step is followed by hybridization of a second fixer polynucleotide that hybridizes a single base upstream from the first fixer polynucleotide.

As before, a mixture of four fluorescently labeled polynucleotides are hybridized to the template polynucleotide, the mixture washed, and the signal read. The fluorescent label is then cleaved, the mixture washed, and the four fluorescently labeled polynucleotides are again allowed to hybridize. The mixture is then washed and the signal read.

These steps are again repeated until the end of the template polynucleotide is reached. In this way, the DNA sequence is obtained without the use of a DNA polymerase.

Example 3

Quantitative PCR in the Presence of Staining Dye SYTO 9
Materials:
Substrate: Lambda DNA New England Biolabs #N3011S
P10-35 (SEQ ID NO: 4) (i.e., "first polynucleotide")
F10-23 (SEQ ID NO: 3) (i.e., "second polynucleotide")
Forward primer 10-15 (SEQ ID NO: 1)
Reverse primer 10-17 (SEQ ID NO: 2)
Taq DNA polymerase New England Biolabs #M0320L
Taq DNA polymerase buffer: 10 mM Tris-HCl, 50 mM KCl pH 8.3 @ 25° C.
dNTPs: Invitrogen #10297018
SYTO® 9 green fluorescent nucleic acid stain Invitrogen #S34854
Methods:
Amplification was carried out in triplicate in 25 µl volume aliquots.

Normal amplification reactions consisted of 12.5 µl of 2× Taq DNA polymerase buffer, 3 mM MgCl$_2$, 200 nM of conventional forward primer 10-15 (SEQ ID NO: 1), conventional reverse primer 10-17 (SEQ ID NO: 2), 200 µM of dNTPs, 1 unit of Taq polymerase, 0.1 ng of Lambda DNA and 2 uM of SYTO® 9. Amplification was performed in BioRad CFX96 Real Time System using the following thermal cycling profile: one cycle at 94° C. for 2 min, followed by 50 cycles at 94° C. for 15 seconds and 66° C. for 1 minute 20 seconds.

Figure 16:
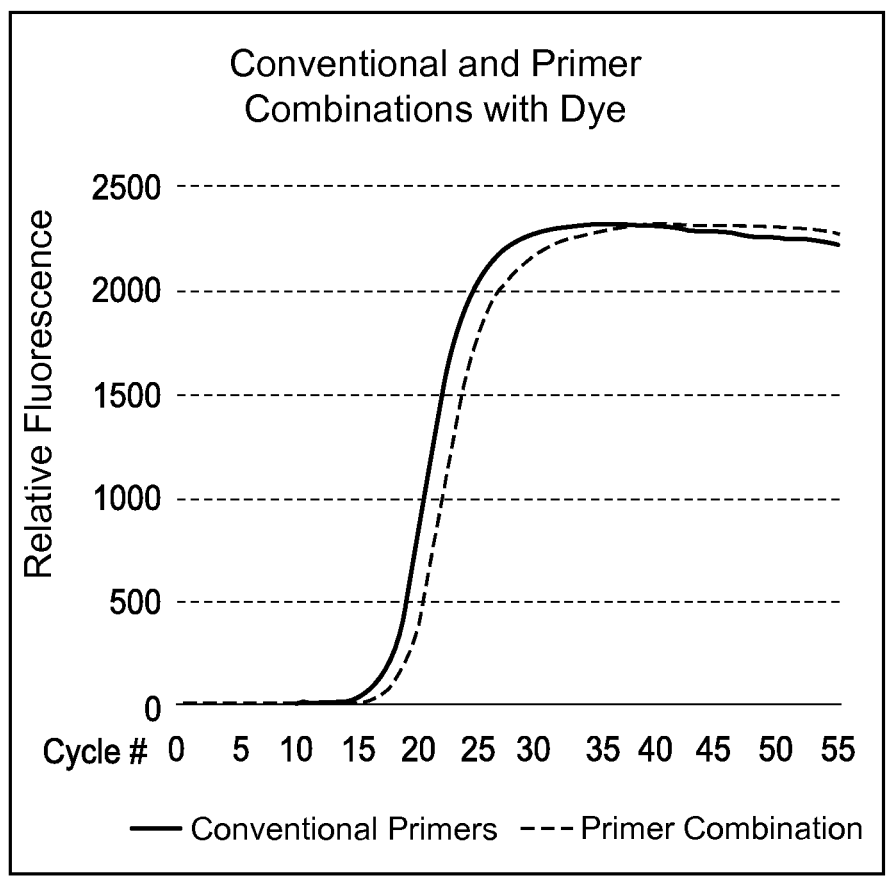
FIG. 16 illustrates the results of quantitative PCR in the presence of staining dye SYTO 9 using the basic polynucleotide combination (i.e., first polynucleotide and second polynucleotide) disclosed herein.

Primer combination P10-35 and F10-23 amplification mixes consisted of 12.5 µl of 2× Taq DNA polymerase buffer, 3 mM MgCl$_2$, 200 nM of conventional forward primer 10-15 (SEQ ID NO: 1), 200 nM of P10-35 (SEQ ID NO: 4), 400 µM of F10-23 (SEQ ID NO: 3), 200 µM of dNTPs, 1 unit of Taq polymerase, 0.1 ng of Lambda DNA and 2 uM of SYTO® 9. Amplification parameters were the same as for the normal primer amplification.
Results:
Averaged amplification curves for the reaction with two conventional primers, 10-15 (SEQ ID NO: 1) and 10-17 (SEQ ID NO: 2), and the reaction with forward conventional primer 10-15 (SEQ ID NO: 1), P10-35 (SEQ ID NO: 4), and F10-23 (SEQ ID NO: 3) are shown in FIG. 16. The results indicate that the assay containing the P10-35/F10-23 pair performs as well as the assay containing conventional primers.

Example 4

Figure 17:
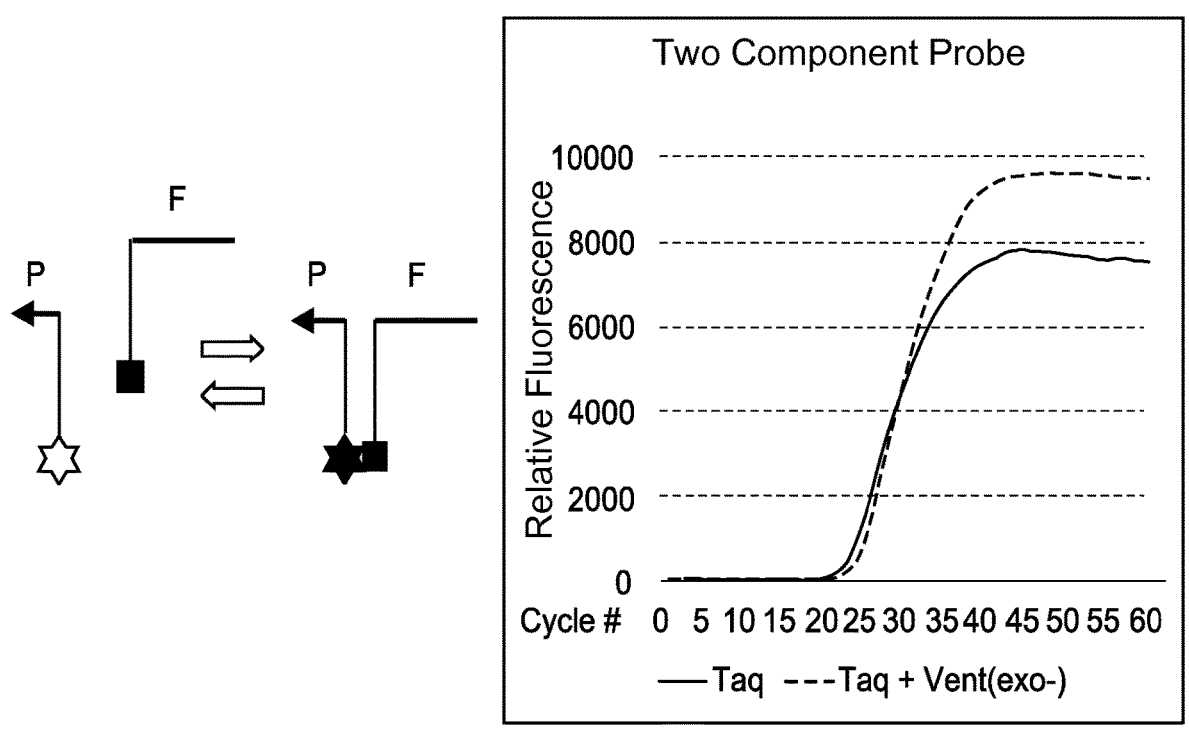
FIG. 17 illustrates the results of quantitative PCR assay with fluorophor-labeled Probe Primer (i.e., first polynucleotide) and quencher-labeled Fixer (i.e., second polynucleotide).

Quantitative PCR Assay with Fluorophor-Labeled Primer Combination and Quencher-Labeled Fixer
Materials:
Substrate: Lambda DNA New England Biolabs #N3011S
5'-Fluorescein-labeled P10-74 (SEQ ID NO: 10) (i.e., "first polynucleotide comprising a label")
3'-Iowa Black quencher-labeled F10-73 (SEQ ID NO: 9) (i.e., "second polynucleotide comprising a quencher")
Forward primer 10-15 (SEQ ID NO: 1)
Taq DNA polymerase New England Biolabs #M0320L
Taq DNA polymerase buffer: 10 mM Tris-HCl, 50 mM KCl pH 8.3 @ 25° C.
Vent (exo-) DNA polymerase New England Biolabs #M0257L
dNTPs: Invitrogen #10297018
Methods:
Amplification reaction with P10-74 contained 12.5 µl of 2× Taq DNA polymerase buffer, 3 mM MgCl$_2$, 200 nM of conventional forward primer 10-15 (SEQ ID NO: 1), 200 nM of P10-74 (SEQ ID NO: 10), and 400 nM of F10-73 (SEQ ID NO: 9), 200 µM of dNTPs, 1 unit of Taq polymerase and 0.1 ng of Lambda DNA. Amplification was performed in BioRad CFX96 Real Time System using the following thermal cycling profile: one cycle at 94° C. for 2 minutes, followed by 50 cycles at 94° C. for 15 seconds and 66° C. for 1 minute 20 seconds and "read" cycle for 10 seconds at 60° C. Some reactions were also supplied with 0.2 units of Vent (exo-) polymerase.
Results:
Amplification real-time PCR curves are shown in FIG. 17. Assay with fluorophor-labeled P10-74 generated a reasonably strong signal that was slightly improved by adding Vent (exo-) polymerase.
Conclusions:
qPCR assay with the P10-74/F10-73 pair with label and quencher, respectively, represents a novel tool for diagnostic applications.

Figure 18:
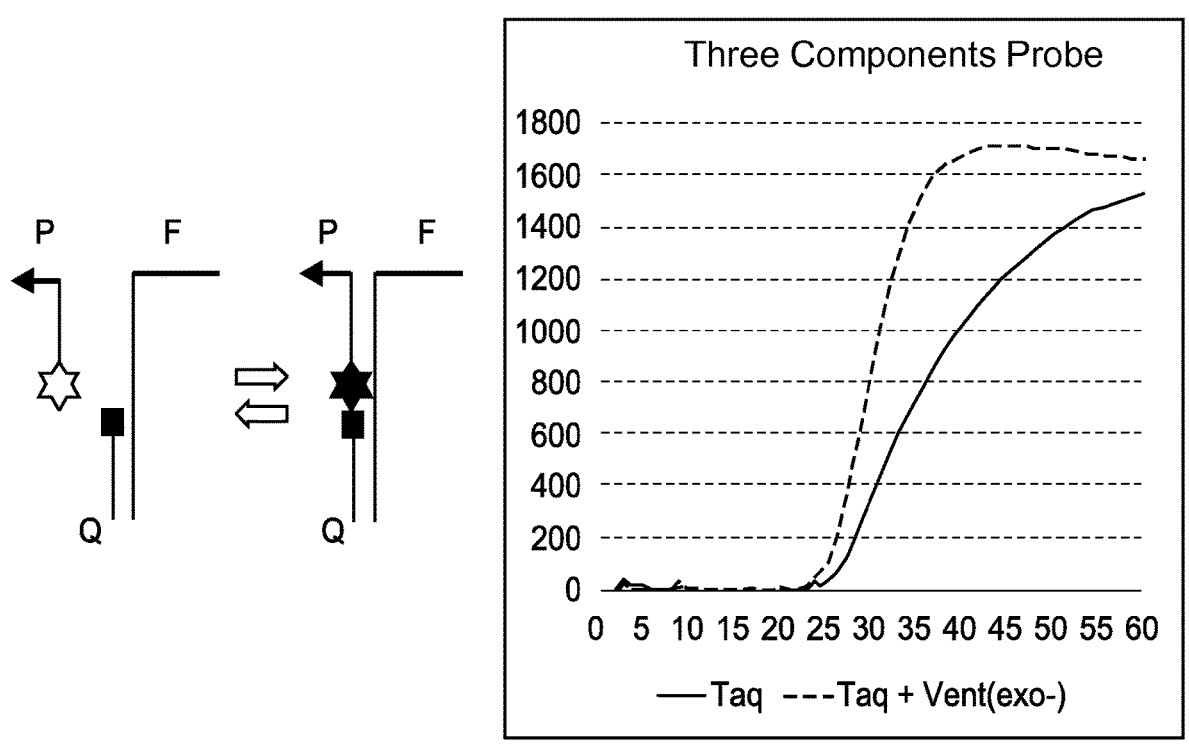
FIG. 18 illustrates the results of a qPCR assay using a fluorophor-labeled Probe Primer (i.e., first polynucleotide) and a universal quencher.

Example 5 qPCR Assay with a Fluorophor-Labeled Primer Combination and Universal Quencher
Materials:
Substrate: Lambda DNA New England Biolabs #N3011S
P10-104 with 3' fluorophore-label and protected bonds (SEQ ID NO: 13) (i.e., "first polynucleotide comprising a label"),
F10-79 (SEQ ID NO: 11) (i.e., "second polynucleotide"),
Quencher oligonucleotide 10-80 (SEQ ID NO: 12) (i.e., "universal quencher polynucleotide"),
Forward primer 10-15 (SEQ ID NO: 1),
Taq DNA polymerase New England Biolabs #M0320L
Taq DNA polymerase buffer: 10 mM Tris-HCl, 50 mM KCl pH 8.3 @ 25° C.
Vent (exo-) DNA polymerase New England Biolabs #M0257L
dNTPs: Invitrogen #10297018
Methods:
Amplification was carried out in triplicate with 25 µl volume aliquots containing 12.5 µl of 2× Taq DNA polymerase buffer, 3 mM MgCl$_2$, 200 nM of conventional forward primer 10-15 (SEQ ID NO: 1), 200 nM of P10-104 (SEQ ID NO: 13), 400 nM of F10-79 (SEQ ID NO: 11), 600 nM of Quencher 10-80 (SEQ ID NO: 12), 200 µM of dNTPs, 1 unit of Taq polymerase, and 0.1 ng of Lambda DNA. Amplification was performed in BioRad CFX96 Real Time System using the following thermal cycling profile: one cycle at 94° C. for 2 min, followed by 50 cycles at 94° C. for 15 seconds and 66° C. for 1 minute 20 seconds and "read" cycle for 10 seconds at 60° C. Some reactions were also supplied with 0.2 units of Vent (exo-) polymerase.
Results:
Averaged amplification real-time PCR curves are shown on FIG. 18. The assay with fluorophor-labeled P10-104 and universal quencher oligonucleotide 10-80 generated a strong signal that was significantly improved by adding Vent (exo-) polymerase.

Conclusions:

qPCR assay with fluorophor-labeled P10-104 and a universal quencher represent a novel qPCR tool for diagnostic applications. It is less expensive for designing multiple assays than the method described in Example 4 because of the use of a universal quencher molecule.

Example 6

Figure 19A:
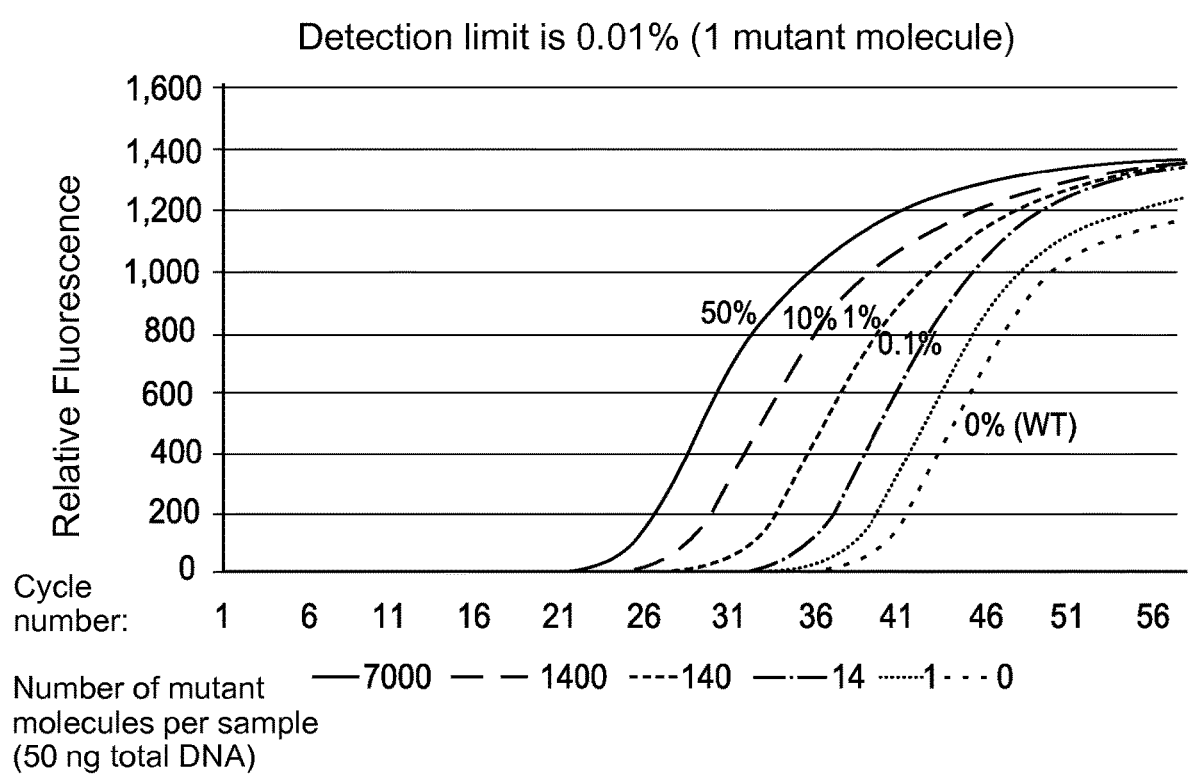
FIGS. 19A and 19B illustrate the results of a qPCR assay to detect mutant KRAS G12V in a mixture using a first polynucleotide, a Fixer (i.e., second polynucleotide) and staining with SYBR green dye.
Figure 19B:
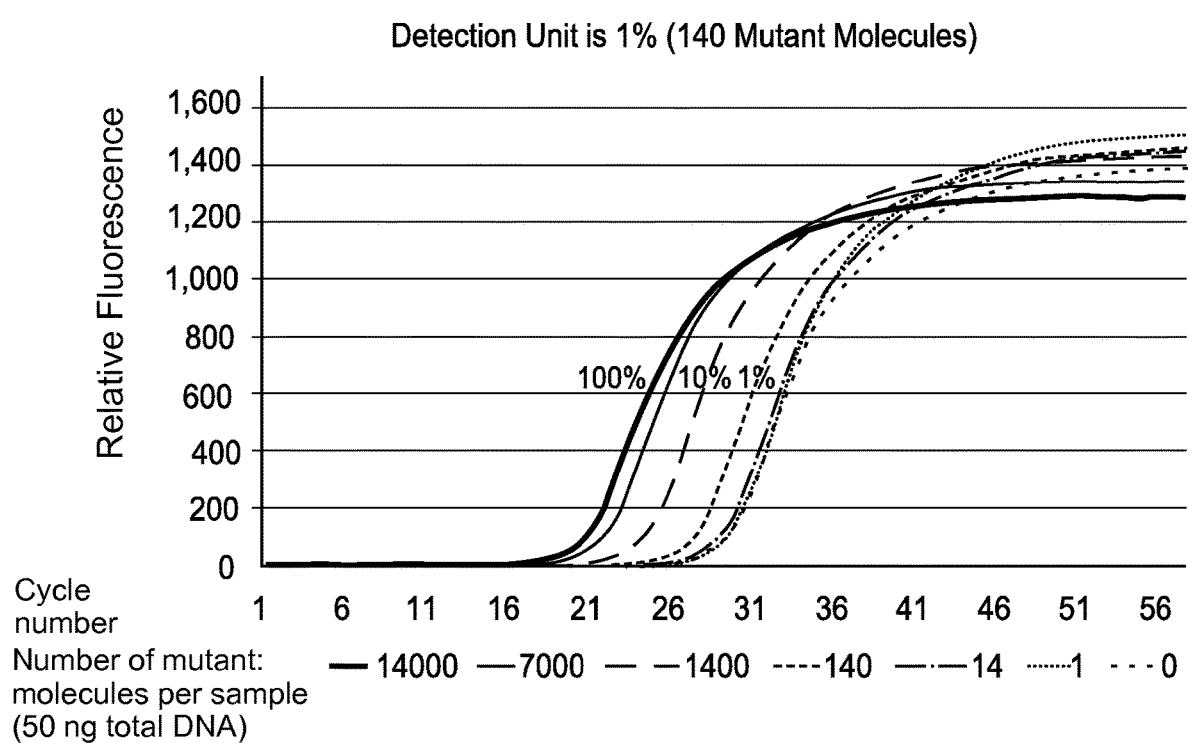

KRAS G12V Mutation Assay with SybrGreen Dye
Materials:
 0.1× TE buffer: 10 mM Tris, 0.1 mM EDTA pH=8.0
 Genomic DNA isolation kit: Qiagen DNeasy Blood & Tissue Kit #69504
 Wild Type human genomic DNA template: Promega human genomic DNA #G1471
 Mutant template: (G12V) genomic DNA isolated from freshly harvested SW480 colorectal adenocarcinoma cells (ATCC#CCL-228)
 Oligonucleotides:
  kras conventional forward primer 10-53 (SEQ ID NO: 6),
  kras G12V conventional reverse primer 10-48 (SEQ ID NO: 5),
  kras P10-56 (SEQ ID NO: 8) (i.e., "first polynucleotide"),
  kras F10-54 (SEQ ID NO: 7) (i.e., "second polynucleotide"),
 Real time SYBR Green qPCR mix: BioRad IQ SYBR Green Supermix #170-8882
Methods:
 Genomic DNA isolation: Kras G12V human genomic DNA was isolated from freshly harvested SW480 cells using Qiagen DNeasy Blood & Tissue Kit according to manufacturer protocol, resuspended in 0.1× TE buffer at a concentration of 100 ng/1.11, aliquoted and stored at −20° C. until use.
 Template preparation: To generate genomic DNA templates for real time PCR reactions, Promega WT genomic DNA was spiked with the designated amount of has G12V genomic DNA so that number of mutant has copies varied from one to 14,000 copies per 50 ng of total DNA, then template DNA was aliquoted and stored at −20° C. until use.
 Real time amplification reaction: Amplification was carried out in triplicate in 25 µl aliquots consisting of 12.5 µl of 2× BioRad IQ SYBR Green Supermix, 200 nM of forward primer 10-53 (SEQ ID NO: 6), 200 nM of conventional reverse primer 10-48 (SEQ ID NO: 5) for conventional PCR reactions or 200 nM of has P10-56 (SEQ ID NO: 8) and 400 nM of has F10-54 (SEQ ID NO: 7) for Primer combination amplification reactions and 50 ng of template DNA using BioRad CFX96 Real Time System. Amplification was performed using the following thermal cycling profile: one cycle at 94° C. for 3 minutes, followed by 60 cycles at 94° C. for 15 seconds and 66° C. for 1 minute 20 seconds.
Results:
 Averaged Primer Combination qPCR curves for normal 50 ng DNA samples containing 50% (7,000 mutant DNA copies), 10% (1,400 mutant DNA copies), 1% (140 mutant DNA copies), 0.1% (14 mutant DNA copies), 0.01% (1 mutant DNA copy), and 0% of the mutant allele G12V are shown in FIG. 19a. FIG. 19b shows analysis of the same DNA samples using conventional primers. In both cases, primers were designed to discriminate the mismatch by the base located at the 3' end of has P10-56 or conventional primer.
Conclusions:
 Primer Combination KRAS G12V mutation assay was able to detect a single copy mutant allele present in the mixture of 14,000 normal DNA sequences (0.01%), while the assay with conventional primers was limited to detection of 140 copies of mutant DNA (1%). There was a 100-fold improvement in sensitivity when Primer Combinations were used for rare mutation detection as compared to conventional primers. Signal originating from a single mutant allele can be discriminated from the background (2-3 cycle difference).

Example 7

Figure 20:
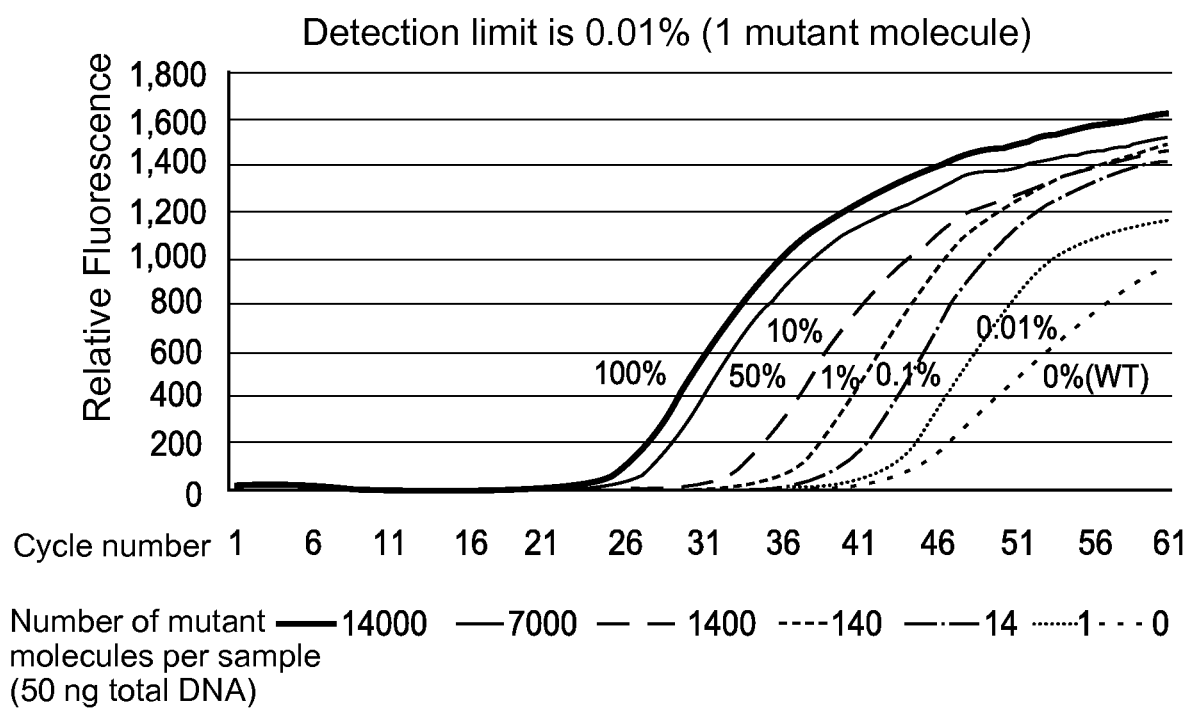
FIG. 20 illustrates the results of a qPCR assay to detect mutant KRAS G12V in formaldehyde-fixed samples using a first polynucleotide, a Fixer (i.e., second polynucleotide) and staining with SYBR green dye.

Detection of Mutations Using Primer Combinations and SybrGreen with Fixed Samples
Materials:
 WT kras HT29 colorectal adenocarcinoma cells ATCC #HTB-38
 G12V genomic DNA was isolated from freshly harvested SW480 colorectal adenocarcinoma cells (ATCC#CCL-228).
Methods:
 Cells fixation: HT29 cells (the source of kras WT DNA) or SW480 cells (source of kras G12V DNA) were trypsinized, washed 3 times in ice cold PBS, fixed in 4% formaldehyde for 10 minutes at room temperature, and washed again 4 times with PBS. After final wash, cell pellets were used to isolate DNA according to the protocol described in Example 5.
 Template preparation and DNA amplification: same as described in Example 5.
Results:
 Averaged Primer Combination qPCR curves for fixed DNA samples containing 100% (14,000 mutant DNA copies), 50% (7,000 mutant DNA copies), 10% (1,400 mutant DNA copies), 1% (140 mutant DNA copies), 0.1% (14 mutant DNA copies), 0.01% (1 mutant DNA copy), and 0% of mutant allele G12V are shown in FIG. 20. Similar to results with non-fixed samples the detection limit was 0.01% or 1 mutant DNA molecule.
Conclusions:
 Primer Combination KRAS G12V mutation qPCR assay sensitivity and selectivity was not affected by cell fixation, indicating the utility of this assay for real clinical samples. Signal originating from a single mutant allele can be discriminated from the background (3 cycle difference).

Example 8

KRAS G12V Assay with a Primer Combination and a Probe Polynucleotide
Materials:
 Template DNA:
  Wild Type human genomic DNA from Promega #G1471, mutant G12V DNA isolated from SW480 cells (see Example 6).
 Oligos:
  kras conventional forward primer 10-178 (SEQ ID NO: 16),
  kras G12V P10-171 (SEQ ID NO: 14) (i.e., "first polynucleotide"),
  kras F10-174 (SEQ ID NO: 15) (i.e., "second polynucleotide"),
  kras specific Zen double quenched probe 10-185 (SEQ ID NO: 19) (i.e., "probe polynucleotide comprising a label and a quencher").
 Real time qPCR mix: BioRad IQ Supermix #170-8862.
Methods:
 Real-time amplification reaction: Amplification was carried out in triplicate with 25 µl aliquots consisting of 12.5 µl of 2× BioRad IQ Supermix, 200 nM of forward primer 10-178 (SEQ ID NO: 16), 200 nM of has G12V P10-171 (SEQ ID NO: 14), 400 nM of has F10-174 (SEQ ID NO: 15), 250 nM of probe 10-185 (SEQ ID NO: 19) and 50 ng of template DNA using BioRad CFX96 Real Time System. Amplification was performed using the following thermal cycling profile: one cycle at 94° C. for 3 minutes, followed by 60 cycles at 94° C. for 10 seconds and 66.5° C. for 1 minute 20 seconds.

Figure 21:
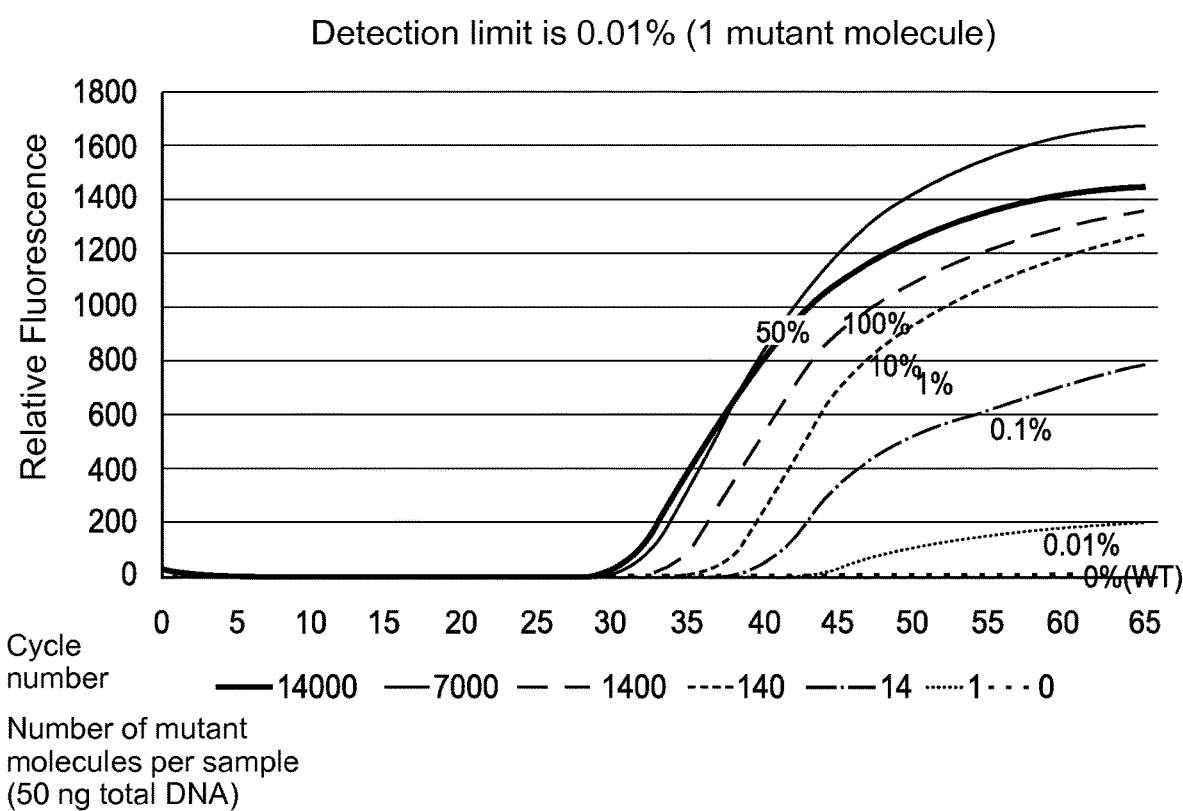
FIG. 21 illustrates the results of a qPCR assay to detect mutant KRAS G12V in a mixture using a first polynucleotide, a Fixer (i.e., second polynucleotide) and a Probe Polynucleotide (i.e., TaqMan).

Results:

Averaged Primer Combination qPCR curves for DNA samples containing 100% (14,000 mutant DNA copies), 50% (7,000 mutant DNA copies), 10% (1,400 mutant DNA copies), 1% (140 mutant DNA copies), 0.1% (14 mutant DNA copies), 0.01% (1 mutant DNA copy), and 0% of mutant allele G12V are shown in FIG. 21. Similar to results described in Examples 6 and 7 the detection limit using the probe polynucleotide was 0.01% or 1 mutant DNA molecule. Signal intensity decreased with low amounts of mutant DNA (0.1% and 0.01%).

Conclusions:

Primer combination KRAS G12V mutation qPCR assay sensitivity did not improve significantly from using the probe polynucleotide. Signal originating from a single mutant allele can be discriminated from the background (flat line up to 65 cycles), showing better selectivity in the probe polynucleotide-containing assay.

Example 9

KRAS G12V Assay with a Primer Combination, Probe Polynucleotide and Blocker Polynucleotide Materials:

Template DNA:

Wild Type human genomic DNA from Promega #G1471, mutant G12V DNA isolated from SW480 cells (see Example 6).

Oligos:

kras P10-184 (SEQ ID NO: 18) (i.e., "first polynucleotide"), kras F10-182 (SEQ ID NO: 17) (i.e., "second polynucleotide"), kras specific Zen double quenched probe 10-210 (SEQ ID NO: 21) (i.e., "probe polynucleotide"), kras conventional reverse primer 10-208 (SEQ ID NO: 20), (i.e., "reverse primer")

blocking oligo 10-213 (SEQ ID NO: 22) (i.e., "blocker polynucleotide")

Real time qPCR mix: BioRad IQ Supermix #170-8862

Methods:

Real time amplification reaction: Amplifications were carried out in triplicate in 25 µl aliquots consisting of 12.5 µl of 2× BioRad IQ Supermix, 200 nM of has P10-184 (SEQ ID NO: 18), 50 nM of has F10-182 (SEQ ID NO: 17), 200 nM of reverse primer 10-208 (SEQ ID NO: 20), 250 nM of probe polynucleotide 10-210 (SEQ ID NO: 21), 2000 nM of blocking oligo 10-213 (SEQ ID NO: 22) and 50 ng of template DNA using BioRad CFX96 Real Time System. Amplification was performed using the following thermal cycling profile: one cycle at 94° C. for 3 minutes, followed by 60 cycles at 94° C. for 10 seconds and 65° C. for 1 minute.

Figure 22:
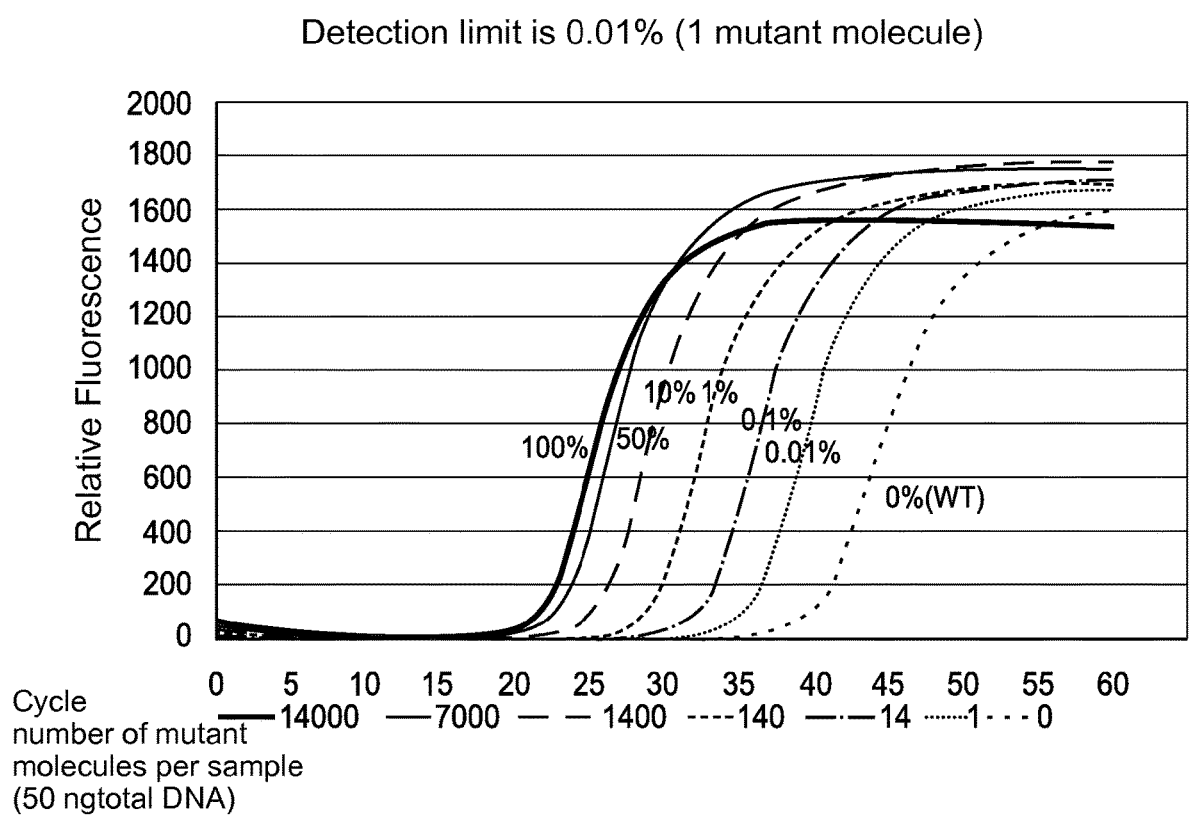
FIG. 22 illustrates the results of a qPCR assay to detect mutant KRAS G12V in a mixture using a first polynucleotide, a Fixer (i.e., second polynucleotide), a Probe Polynucleotide (i.e., TaqMan), and a blocker polynucleotide.

Results:

Averaged Primer Combination qPCR curves for DNA samples containing 100% (14,000 mutant DNA copies), 50% (7,000 mutant DNA copies), 10% (1,400 mutant DNA copies), 1% (140 mutant DNA copies), 0.1% (14 mutant DNA copies), 0.01% (1 mutant DNA copy), and 0% of mutant allele G12V are shown in FIG. 22.

Conclusions:

Addition of the blocker oligonucleotide 10-213 (SEQ ID NO: 22) (in combination with the probe polynucleotide) significantly improved the characteristics of the assay. Similar to results described in Examples 4, 5 and 6 the detection limit using TaqMan probe and the blocker was 0.01%, or 1 mutant DNA molecule, but there was ~100-1000× improvement in selectivity for detection of a single mutant allele than the assay described in Example 6 (5-7 cycles difference between single mutant copy and the background originating from 14,000 normal DNA molecules).

Example 10

Primer Combination KRAS G12V Assay with Probe Polynucleotide, Blocker Polynucleotide, and 3'-Base LNA Modification Materials:

Template DNA:

Wild Type human genomic DNA from Promega #G1471, mutant G12V DNA isolated from SW480 cells (see Example 6).

Oligos:

kras P10-236 with 3' LNA (SEQ ID NO: 23) (i.e., "first polynucleotide comprising a locked nucleic acid at the 3' end"), kras F10-182 (SEQ ID NO: 17) (i.e., "second polynucleotide"), kras specific Zen double quenched probe 10-210 (SEQ ID NO: 21) (i.e., "probe polynucleotide"), kras conventional reverse primer 10-208 (SEQ ID NO: 20) (i.e., "reverse primer"), blocking oligo 10-213 (SEQ ID NO: 22) (i.e., "blocker polynucleotide")

Real time qPCR mix: BioRad IQ Supermix #170-8862

Methods:

Real time amplification reaction: Amplifications were carried out in triplicates in 25 µl volume consisting of 12.5 µl of 2× BioRad IQ Supermix, 200 nM of kras P10-236 (SEQ ID NO: 23), 50 nM of kras F10-182 (SEQ ID NO: 17), 200 nM of reverse primer 10-208 (SEQ ID NO: 20), 250 nM of probe polynucleotide 10-210 (SEQ ID NO: 21), 2000 nM of blocking oligo 10-213 (SEQ ID NO: 22) and 50 ng of template DNA using BioRad CFX96 Real Time System. Amplification was performed using the following thermal cycling profile: one cycle at 94° C. for 3 minutes, followed by 60 cycles at 94° C. for 10 seconds and 65° C. for 1 minute.

Figure 23:
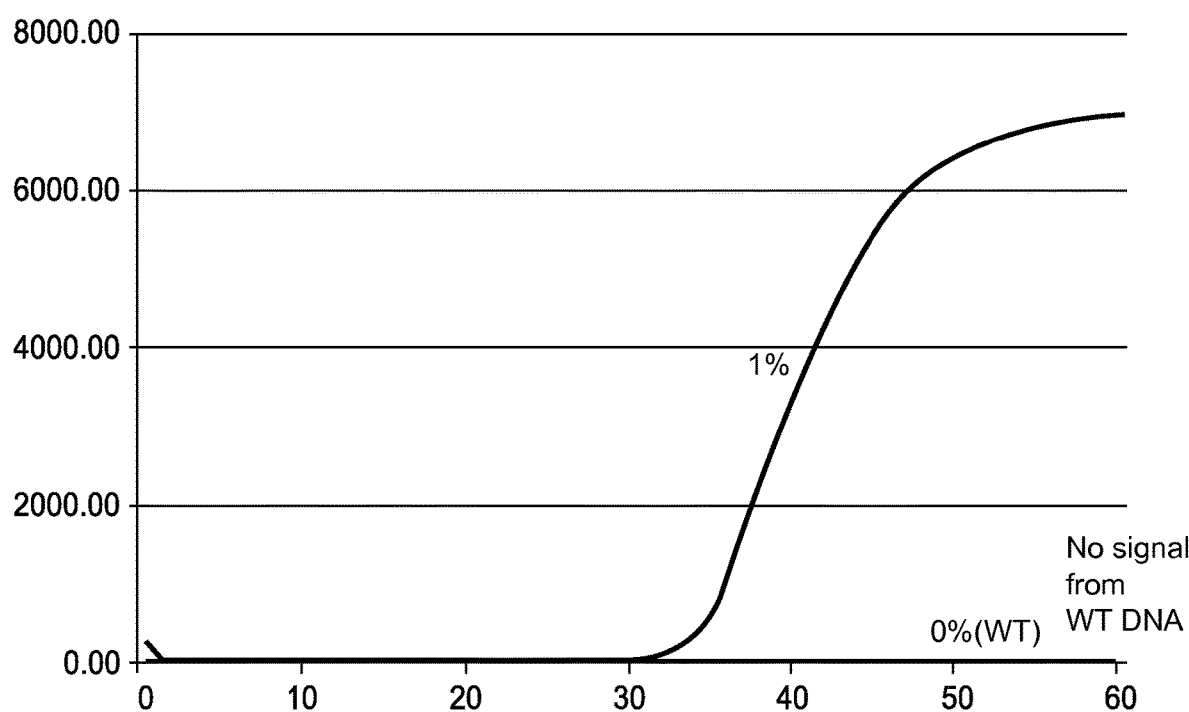
FIG. 23 illustrates the results of a qPCR assay to detect mutant KRAS G12V in a mixture using a first polynucleotide modified with LNA at its 3' end, a Fixer (i.e., second polynucleotide), a Probe Polynucleotide (i.e., TaqMan), and a blocker polynucleotide.

Results:

Averaged Primer Combination qPCR curves for DNA samples containing 1% (140 mutant DNA copies) and 0% of mutant allele G12V are shown in FIG. 23.

Conclusions:

Primer Combination KRAS g12V assay with probe polynucleotide, blocker polynucleotide and 3'-base LNA modification of P10-236 demonstrated the best sensitivity (single mutant allele) and the best selectivity (no signal from 14,000 wild type DNA molecules) as compared to the previous examples.

Example 11

Single Mutation Detection Using Improved KRAS G12V Assay at 0.5 Copy of G12V DNA Per 14,000 Copies of WT DNA: Analysis of 16 Samples Materials:
Same as Example 10.

Methods:

Template Preparation:
To generate 0.5 copy KRAS G12V DNA template, previously isolated SW480 genomic DNA was diluted in 10 ng/µl Promega Human genomic DNA to the final concentration of 1 SW480 DNA molecule per 10 µl of WT DNA.

Real time amplification reaction:
Amplifications were performed in 16 aliquots with 5 µl of 0.5 copy KRAS G12V DNA template or WT DNA using amplification mix composition and protocol described in Example 10.

Figure 24A:
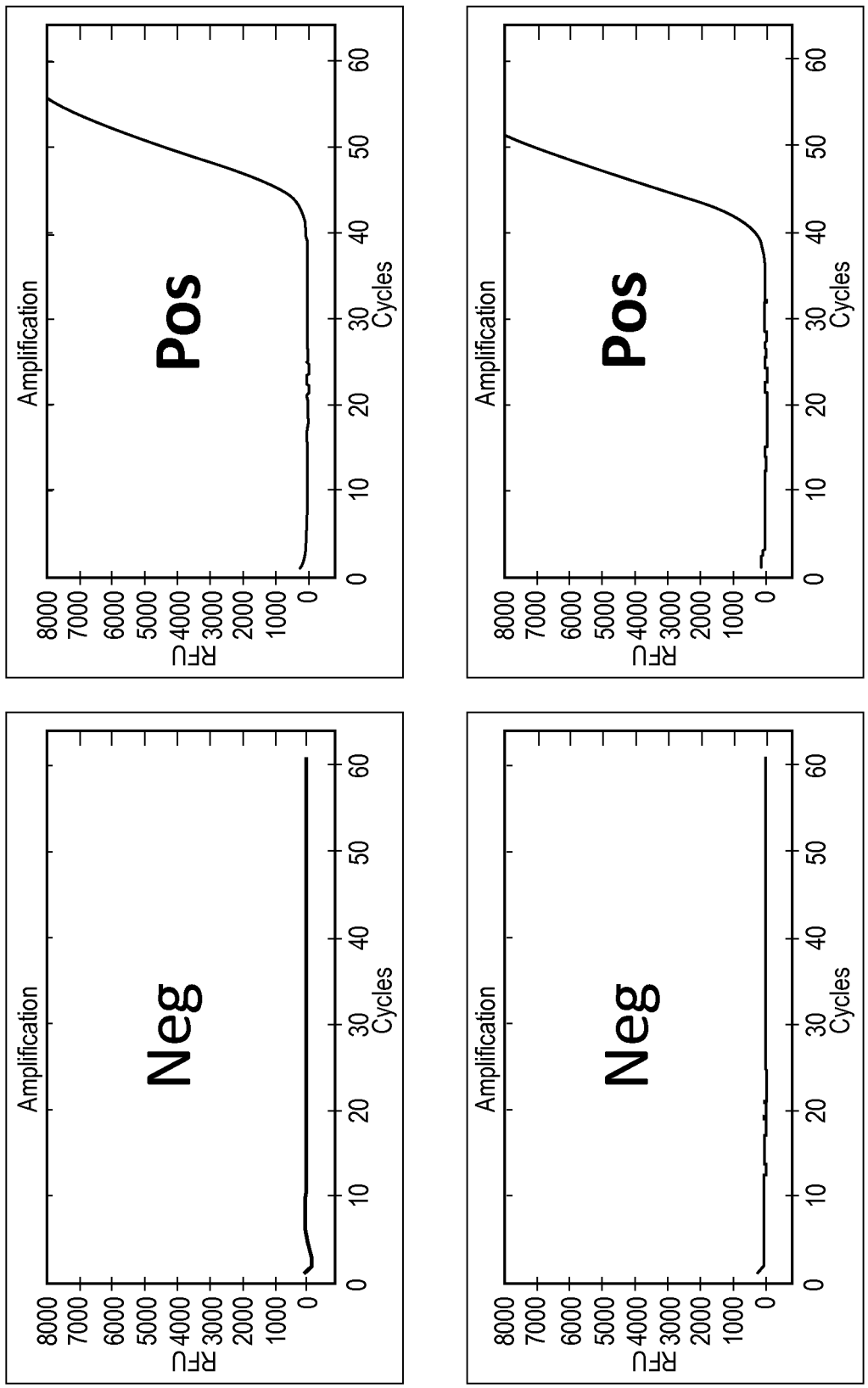
FIGS. 24A-24D illustrate the results of a qPCR assay to detect mutant KRAS G12V in a mixture with 0.5 copy/reaction of KRAS G12V DNA (determined statistically) using a first polynucleotide modified with LNA at its 3' end, a Fixer (i.e., second polynucleotide), a Probe Polynucleotide (i.e., TaqMan), and a blocker polynucleotide.

Results:
16 replicate experiments using improved KRAS G12V qPCR mutation assay from Example 10 and samples containing (statistically) 0.5 copy of G12V DNA per 14,000 copies of WT DNA are shown in FIG. 24a. 50-60% (8-10 out of 16) of spiked and diluted DNA samples indicated the presence of a single mutant DNA, and 40-50% (6-8 out of 16) of spiked and diluted DNA samples showed no signal, in agreement with the statistical expectations.

Figure 24B:
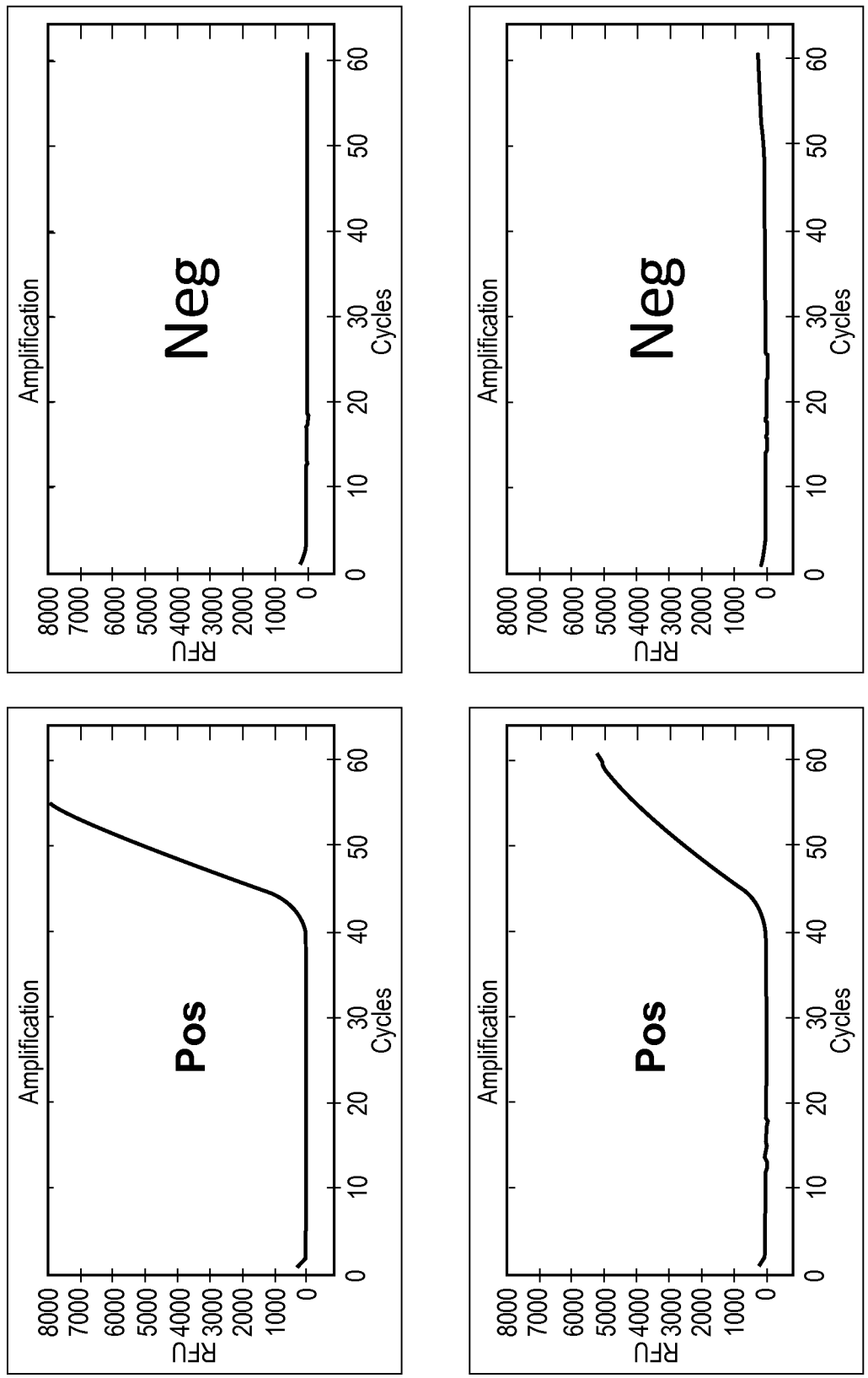
Figure 24C:
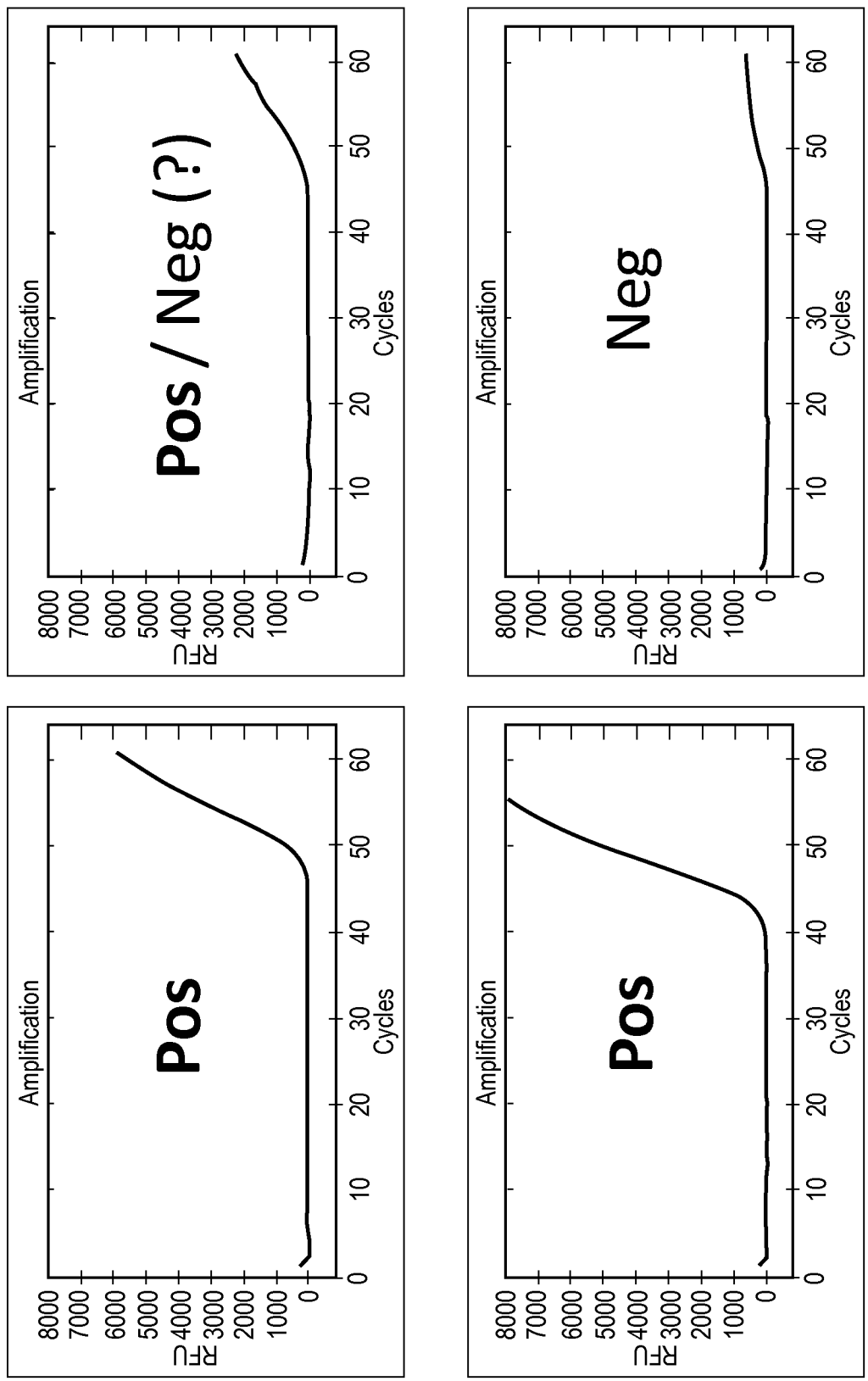
Figure 24D:
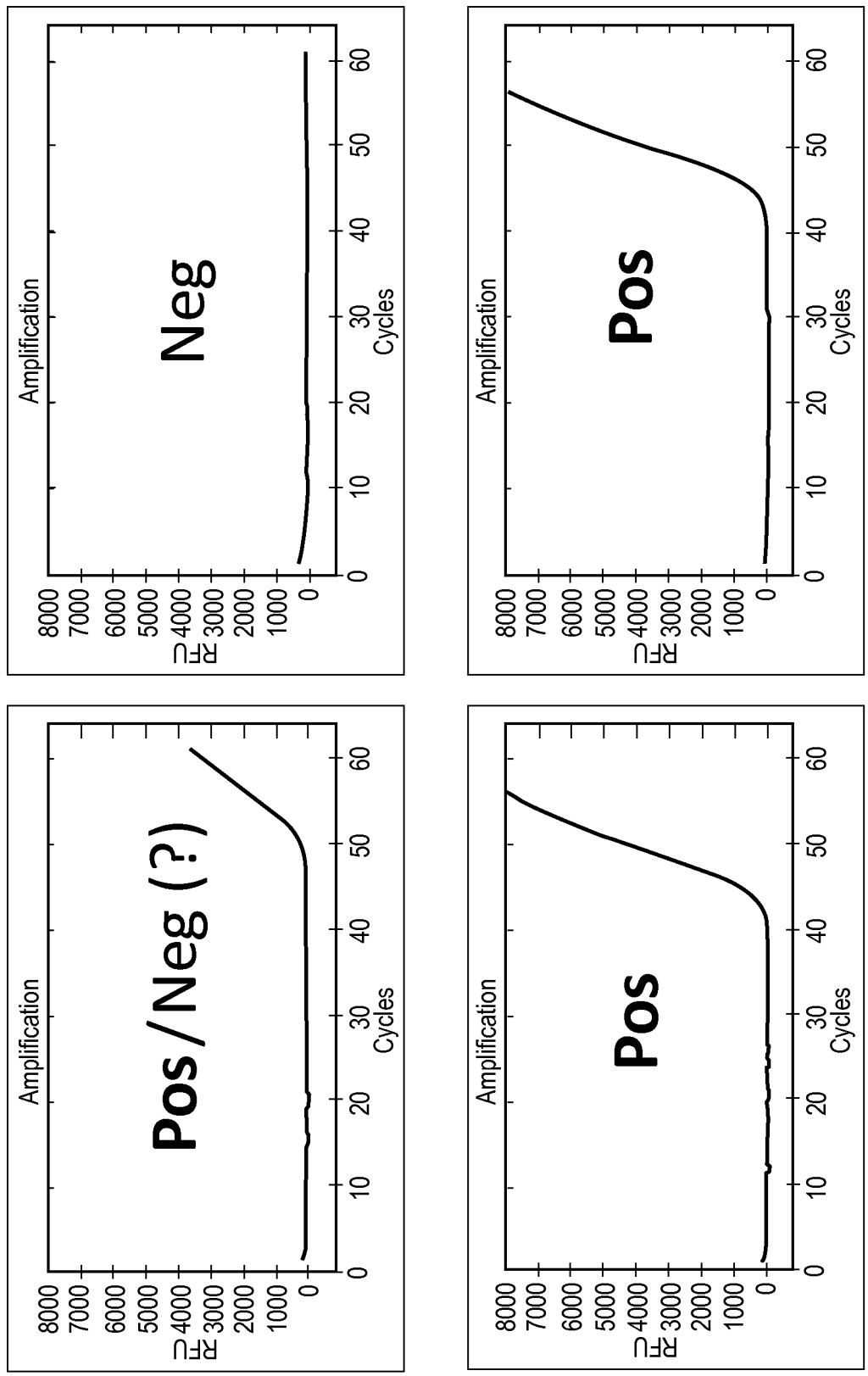

16 replicate experiments using improved KRAS G12V qPCR mutation assay from Example 10 and samples containing 14,000 copies of WT DNA (no mutant DNA added) are shown in FIG. 24b. 94% of WT DNA samples (15 out of 16) showed no signal, indicating a very high selectivity of single mutant DNA detection by the improved KRAS G12V Primer Combination qPCR mutation assay.

Conclusions:
Primer Combination G12V assay with probe polynucleotide, blocker and 3'-modified LNA base had 100% sensitivity and 94-100% selectivity for detection of a single mutant allele in excess of more than 10,000 non-mutant DNA molecules. Such parameters of the G12V assay satisfy the most demanding characteristics of a diagnostic assay. The assay is ideally suitable for detection of rare cancer cells circulating in blood for efficient and non-invasive management of CRC and NSCLC patients.

What is claimed:

1. A polynucleotide primer combination comprising a first polynucleotide and a second polynucleotide,
the first polynucleotide (P) comprising (i) a first domain (Pa) at the 3' end having a sequence that (a) does not comprise a blocking group, (b) is fully complementary to a sequence ($T_1$) in a first target polynucleotide region, (c) is not fully complementary to a sequence ($T_1^*$) in a first non-target polynucleotide region, and (d) is about 5 to about 20 nucleotides in length, and (ii) a second domain (Pc) comprising a unique polynucleotide sequence, and
the second polynucleotide (F) comprising (i) a first domain (Fb) having a sequence that is longer than Pa and that is complementary to a second target polynucleotide region ($T_2$) and (ii) a second domain (Fd) comprising a polynucleotide sequence sufficiently complementary to Pc such that Pc and Fd will hybridize when Pa is hybridized to $T_1$ and Fb is hybridized to $T_2$, wherein F further comprises a blocking group attached at its 3' end which blocks extension from a DNA polymerase,
wherein the sequence in the first region ($T_1$) in the target polynucleotide differs at a base from the sequence in the first region ($T_1^*$) in the non-target polynucleotide.

2. A polynucleotide primer combination comprising a first polynucleotide and a second polynucleotide,
the first polynucleotide (P) comprising (i) a first domain (Pa) at the 3' end having a sequence that (a) does not comprise a blocking group, (b) is fully complementary to a sequence ($T_1$) in a first target polynucleotide region, (c) is not fully complementary to a sequence ($T_1^*$) in a first non-target polynucleotide region, and (d) is about 5 to about 20 nucleotides in length, and (ii) a second domain (Pc) comprising a unique polynucleotide sequence, and
the second polynucleotide (F) comprising (i) a first domain (Fb) having a sequence that is longer than Pa and that is complementary to a second target polynucleotide region ($T_2$) and (ii) a second domain (Fd) comprising a polynucleotide sequence sufficiently complementary to Pc such that Pc and Fd will hybridize when Pa is hybridized to T1 and Fb is hybridized to $T_2$, wherein F further comprises a blocking group attached at its 3' end which blocks extension from a DNA polymerase,
wherein P and/or F further comprise a modified nucleic acid, and
wherein the sequence in the first region ($T_1$) in the target polynucleotide differs at a base from the sequence in the first region ($T_1^*$) in the non-target polynucleotide.

3. A method of detecting the presence of a target polynucleotide in a sample with the primer combination of claim 1,
the method comprising the steps of:
contacting the sample with the primer combination and a polymerase under conditions that allow extension of a sequence from Pa which is complementary to the target polynucleotide when the target polynucleotide is present in the sample and
detecting the sequence extended from Pa indicating the presence of the target polynucleotide in the sample.

4. A method of initiating polymerase extension on a target polynucleotide in a sample using the primer combination of claim 1,
wherein the sample comprises a mixture of (i) a target polynucleotide that has a sequence ($T_1$) in a first region that is fully complementary to the sequence in Pa and (ii) a non-target polynucleotide that has a sequence ($T_1^*$) in a first region that is not fully complementary to Pa,
the method comprising the step of contacting the sample with the primer combination and a polymerase under conditions that allow extension of a sequence from Pa and complementary to the target polynucleotide strand when Pa contacts $T_1$.

5. A method of amplifying a target polynucleotide in a sample using the polynucleotide primer combination of claim 1,
wherein the sample comprises a mixture of (i) a target polynucleotide that has a sequence in a first region ($T_1$) that is fully complementary to the sequence in Pa and (ii) one or more non-target polynucleotides that are not fully complementary to Pa;
the method comprising the steps of:
(a) contacting the sample with the primer combination and a polymerase under conditions that allow extension of a sequence from Pa which is complementary to the target polynucleotide when the target polynucleotide is present in the sample,
(b) denaturing the sequence extended from Pa from the target polynucleotide, and
(c) repeating step (a) in the presence of a reverse primer having a sequence complementary to a region in the sequence extended from Pa in step (b) to amplify the target polynucleotide,
wherein extension and amplification of the target polynucleotide occurs when Pa is fully complementary to the sequence in the Pa but is less efficient or does not occur when the first region in the target polynucleotide is not fully complementary to the sequence in Pa.

6. The method of claim 5 wherein the reverse primer is a primer combination comprising a first polynucleotide and a second polynucleotide,
the first polynucleotide (PP) comprising a first domain (PPa) having a sequence that is fully complementary to a first region ($TT_1$) in the sequence extended from Pa in step (a) and a second domain (PPc) comprising a unique polynucleotide sequence, and
the second polynucleotide (FF) comprising a first domain (FFb) that is complementary to a second region ($TT_2$) in the sequence extended from Pa in step (a) and a second domain (FFd) comprising a polynucleotide sequence sufficiently complementary to PPc such that PPc and FFd will hybridize under appropriate conditions.

7. The polynucleotide primer combination of claim 1 further comprising a blocker polynucleotide, the blocker polynucleotide comprising a nucleotide sequence that is complementary to a third target polynucleotide region ($T_3$), wherein $T_3$ is located 5' of $T_1$ and $T_2$.

8. The polynucleotide primer combination of claim 7 wherein a nucleotide at the 3' end of P and a nucleotide at the 5' end of the blocker polynucleotide overlap.

9. The polynucleotide primer combination of claim 8 wherein the blocker polynucleotide has a sequence that overlaps Pa over the whole length of Pa.

10. The polynucleotide primer combination of claim 8 wherein the nucleotide at the 3' end of P and the nucleotide at the 5' end of the blocker polynucleotide are different.

11. The polynucleotide primer combination of claim 7, wherein the 5' base of the blocker polynucleotide is complementary to a non-target polynucleotide and is not complementary to the target polynucleotide.

12. The polynucleotide primer combination of claim 7, further comprising a blocking group attached to the blocker at its 3' end which blocks extension from a DNA polymerase.

13. The polynucleotide primer combination of claim 1 further comprising a reverse primer, wherein the reverse primer comprises a polynucleotide sequence complementary to a polynucleotide strand comprising a sequence that hybridizes to $T_1$.

14. The polynucleotide primer combination of claim 1, wherein P is DNA, modified DNA, RNA, modified RNA, peptide nucleic acid (PNA), or combinations thereof.

15. The polynucleotide primer combination of claim 2, wherein P is DNA, modified DNA, RNA, modified RNA, peptide nucleic acid (PNA), or combinations thereof.

16. The polynucleotide primer combination of claim 1, wherein F is DNA, modified DNA, RNA, modified RNA, peptide nucleic acid (PNA), or combinations thereof.

17. The polynucleotide primer combination of claim 2, wherein F is DNA, modified DNA, RNA, modified RNA, peptide nucleic acid (PNA), or combinations thereof.

18. The polynucleotide primer combination of claim 1, wherein Pc is from about 5 bases in length to about 200 bases in length, about 5 bases in length to about 150 bases in length, about 5 bases in length to about 100 bases in length, about 5 bases in length to about 50 bases in length, about 5 bases in length to about 45 bases in length, about 5 bases in length to about 40 bases in length, about 5 bases in length to about 35 bases in length, about 5 bases in length to about 30 bases in length, about 5 bases in length to about 25 bases in length, about 5 bases in length to about 20 bases in length, about 5 bases in length to about 15 bases in length, about 10 to about 50 bases in length, about 10 bases in length to about 45 bases in length, about 10 bases in length to about 40 bases in length, about 10 bases in length to about 35 bases in length, about 10 bases in length to about 30 bases in length, about 10 bases in length to about 25 bases in length, about 10 bases in length to about 20 bases in length, or about 10 bases in length to about 15 bases in length.

19. The polynucleotide primer combination of claim 1, wherein Fb is from about 10 bases in length to about 5000 bases in length, about 10 bases in length to about 4000 bases in length, about 10 bases in length to about 3000 bases in length, about 10 bases in length to about 2000 bases in length, about 10 bases in length to about 1000 bases in length, about 10 bases in length to about 500 bases in length, about 10 bases in length to about 250 bases in length, about 10 bases in length to about 200 bases in length, about 10 bases in length to about 150 bases in length, about 10 bases in length to about 100 bases in length, about 10 bases in length to about 95 bases in length, about 10 bases in length to about 90 bases in length, about 10 bases in length to about 85 bases in length, about 10 bases in length to about 80 bases in length, about 10 bases in length to about 75 bases in length, about 10 bases in length to about 70 bases in length, about 10 bases in length to about 65 bases in length, about 10 bases in length to about 60 bases in length, about 10 bases in length to about 55 bases in length, about 10 bases in length to about 50 bases in length, about 10 bases in length to about 45 bases in length, about 10 bases in length to about 40 bases in length, about 10 bases in length to about 35 bases in length, about 10 bases in length to about 30 bases in length, or about 10 bases in length to about 100 bases in length.

20. The polynucleotide primer combination of claim 1, wherein Fd is from about 5 bases in length to about 200 bases in length, about 5 bases in length to about 150 bases in length, about 5 bases in length to about 100 bases in length, about 5 bases in length to about 50 bases in length, about 5 bases in length to about 45 bases in length, about 5 bases in length to about 40 bases in length, about 5 bases in length to about 35 bases in length, about 5 bases in length to about 30 bases in length, about 5 bases in length to about 25 bases in length, about 5 bases in length to about 20 bases in length, about 5 bases in length to about 15 bases in length, about 10 to about 50 bases in length, about 10 bases in length to about 45 bases in length, about 10 bases in length to about 40 bases in length, about 10 bases in length to about 35 bases in length, about 10 bases in length to about 30 bases in length, about 10 bases in length to about 25 bases in length, about 10 bases in length to about 20 bases in length, or about 10 bases in length to about 15 bases in length.

21. The polynucleotide primer combination of claim 2, wherein Pc is from about 5 bases in length to about 200 bases in length, about 5 bases in length to about 150 bases in length, about 5 bases in length to about 100 bases in length, about 5 bases in length to about 50 bases in length, about 5 bases in length to about 45 bases in length, about 5 bases in length to about 40 bases in length, about 5 bases in length to about 35 bases in length, about 5 bases in length to about 30 bases in length, about 5 bases in length to about 25 bases in length, about 5 bases in length to about 20 bases in length, about 5 bases in length to about 15 bases in length, about 10 to about 50 bases in length, about 10 bases in length to about 45 bases in length, about 10 bases in length to about 40 bases in length, about 10 bases in length to about 35 bases in length, about 10 bases in length to about 30 bases in length, about 10 bases in length to about 25 bases in length, about 10 bases in length to about 20 bases in length, or about 10 bases in length to about 15 bases in length.

22. The polynucleotide primer combination of claim 2, wherein Fb is from about 10 bases in length to about 5000 bases in length, about 10 bases in length to about 4000 bases in length, about 10 bases in length to about 3000 bases in length, about 10 bases in length to about 2000 bases in length, about 10 bases in length to about 1000 bases in length, about 10 bases in length to about 500 bases in length, about 10 bases in length to about 250 bases in length, about 10 bases in length to about 200 bases in length, about 10 bases in length to about 150 bases in length, about 10 bases in length to about 100 bases in length, about 10 bases in length to about 95 bases in length, about 10 bases in length to about 90 bases in length, about 10 bases in length to about 85 bases in length, about 10 bases in length to about 80 bases in length, about 10 bases in length to about 75 bases in length, about 10 bases in length to about 70 bases in length, about 10 bases in length to about 65 bases in length, about 10 bases in length to about 60 bases in length, about 10 bases in length to about 55 bases in length, about 10 bases in length to about 50 bases in length, about 10 bases in length to about 45 bases in length, about 10 bases in length to about 40 bases in length, about 10 bases in length to about 35 bases in length, about 10 bases in length to about 30 bases in length, or about 10 bases in length to about 100 bases in length.

23. The polynucleotide primer combination of claim 2, wherein Fd is from about 5 bases in length to about 200 bases in length, about 5 bases in length to about 150 bases in length, about 5 bases in length to about 100 bases in length, about 5 bases in length to about 50 bases in length, about 5 bases in length to about 45 bases in length, about 5 bases in length to about 40 bases in length, about 5 bases in length to about 35 bases in length, about 5 bases in length to about 30 bases in length, about 5 bases in length to about 25 bases in length, about 5 bases in length to about 20 bases in length, about 5 bases in length to about 15 bases in length, about 10 to about 50 bases in length, about 10 bases in length to about 45 bases in length, about 10 bases in length to about 40 bases in length, about 10 bases in length to about 35 bases in length, about 10 bases in length to about 30 bases in length, about 10 bases in length to about 25 bases in length, about 10 bases in length to about 20 bases in length, or about 10 bases in length to about 15 bases in length.

24. The method of claim 3, wherein P and/or F further comprise a modified nucleic acid.

25. The method of claim 4, wherein P and/or F further comprise a modified nucleic acid.

26. The method of claim 5, wherein P and/or F further comprise a modified nucleic acid.

* * * * *